US012642672B2

(12) United States Patent
Alva et al.

(10) Patent No.: US 12,642,672 B2
(45) Date of Patent: Jun. 2, 2026

(54) INTRA-OPERATIVE GAP DETECTION

(71) Applicant: Orthosensor Inc., Dania, FL (US)

(72) Inventors: Carlos O. Alva, Boynton Beach, FL (US); Ezra S. Johnson, Reeds Spring, MT (US); Matthias Verstraete, Chaam (NL)

(73) Assignee: Howmedica Osteonics Corp., Mahwah, NJ (US)

( * ) Notice: Subject to any disclaimer, the term of this patent is extended or adjusted under 35 U.S.C. 154(b) by 659 days.

(21) Appl. No.: 18/133,654

(22) Filed: Apr. 12, 2023

(65) Prior Publication Data

US 2023/0255797 A1 Aug. 17, 2023

Related U.S. Application Data

(63) Continuation of application No. 18/108,954, filed on Feb. 13, 2023.

(Continued)

(51) Int. Cl.
| | |
|---|---|
| *A61F 2/46* | (2006.01) |
| *A61B 5/00* | (2006.01) |
| *A61B 5/06* | (2006.01) |

(52) U.S. Cl.
CPC ............ *A61F 2/4657* (2013.01); *A61B 5/062* (2013.01); *A61B 5/4528* (2013.01); *A61B 5/6878* (2013.01); *A61F 2002/4666* (2013.01)

(58) Field of Classification Search
CPC ........ A61F 2/38; A61F 2/3859; A61F 2/4657; A61B 5/062; A61B 5/4528; A61B 5/6878; A61B 5/4851; A61B 5/6812
See application file for complete search history.

(56) References Cited

U.S. PATENT DOCUMENTS

| | | |
|---|---|---|
| 6,245,109 B1 | 6/2001 | Mendes et al. |
| 6,447,448 B1 | 9/2002 | Ishikawa et al. |
| (Continued) | | |

FOREIGN PATENT DOCUMENTS

| | | |
|---|---|---|
| DE | 202015009423 U1 | 7/2017 |
| IT | UB20156086 | 6/2017 |
| (Continued) | | |

OTHER PUBLICATIONS

International Search Report and Written Opinion issued in Appln. No. PCT/US2023/013019 mailed May 24, 2023 (22 pages).

(Continued)

*Primary Examiner* — Brian A Dukert
(74) *Attorney, Agent, or Firm* — Lerner David LLP

(57) ABSTRACT

Disclosed herein are joint implants and methods for intra-operatively detecting joint implant gap. A method for detecting a joint implant gap may include coupling a first implant to a first bone of a joint, coupling a second implant to a second bone of the joint, measuring an amplitude of a magnetic flux density using a magnetic sensor to determine a gap between the first and second implants. The first implant may include at least one magnetic marker. The second implant may be configured to contact the first implant. The second implant may include at least one magnetic sensor to detect the magnetic flux density of the magnetic marker. The gap between the first and second implant may be intra-operatively determined using the measured amplitude of the magnetic flux density.

21 Claims, 48 Drawing Sheets

Related U.S. Application Data

(60) Provisional application No. 63/444,056, filed on Feb. 8, 2023, provisional application No. 63/444,045, filed on Feb. 8, 2023, provisional application No. 63/483,045, filed on Feb. 3, 2023, provisional application No. 63/443,146, filed on Feb. 3, 2023, provisional application No. 63/482,656, filed on Feb. 1, 2023, provisional application No. 63/482,659, filed on Feb. 1, 2023, provisional application No. 63/482,097, filed on Jan. 30, 2023, provisional application No. 63/482,109, filed on Jan. 30, 2023, provisional application No. 63/481,660, filed on Jan. 26, 2023, provisional application No. 63/481,053, filed on Jan. 23, 2023, provisional application No. 63/431,094, filed on Dec. 8, 2022, provisional application No. 63/423,932, filed on Nov. 9, 2022, provisional application No. 63/419,781, filed on Oct. 27, 2022, provisional application No. 63/419,522, filed on Oct. 26, 2022, provisional application No. 63/419,455, filed on Oct. 26, 2022, provisional application No. 63/359,384, filed on Jul. 8, 2022, provisional application No. 63/309,809, filed on Feb. 14, 2022.

(56)            References Cited

U.S. PATENT DOCUMENTS

| | | | |
|---|---|---|---|
| 6,573,706 | B2 | 6/2003 | Mendes et al. |
| 6,583,630 | B2 | 6/2003 | Mendes et al. |
| 6,610,096 | B2 | 8/2003 | MacDonald |
| 6,821,299 | B2 | 11/2004 | Kirking et al. |
| 6,926,670 | B2 | 8/2005 | Rich et al. |
| 6,968,743 | B2 | 11/2005 | Rich et al. |
| 7,190,273 | B2 | 3/2007 | Liao et al. |
| 7,195,645 | B2 | 3/2007 | Disilvestro et al. |
| 7,218,232 | B2 | 5/2007 | DiSilvestro et al. |
| 7,328,131 | B2 | 2/2008 | Donofrio et al. |
| 7,347,874 | B2 | 3/2008 | Disilvestro |
| 7,384,403 | B2 | 6/2008 | Sherman |
| 7,470,288 | B2 | 12/2008 | Dietz et al. |
| 7,704,282 | B2 | 4/2010 | Disilvestro et al. |
| 7,766,862 | B2 | 8/2010 | Gerber et al. |
| 7,776,686 | B2 | 8/2010 | Makabe et al. |
| 7,900,518 | B2 | 3/2011 | Tai et al. |
| 7,976,534 | B2 | 7/2011 | Gerber et al. |
| 8,083,741 | B2 | 12/2011 | Morgan et al. |
| 8,121,678 | B2 | 2/2012 | Linder et al. |
| 8,241,296 | B2 | 8/2012 | Wasielewski |
| 8,388,553 | B2 | 3/2013 | James et al. |
| 8,419,801 | B2 | 4/2013 | DiSilvestro et al. |
| 8,506,514 | B2 | 8/2013 | Pedersen et al. |
| 8,509,888 | B2 | 8/2013 | Linder et al. |
| 8,551,092 | B2 | 10/2013 | Morgan et al. |
| 8,707,782 | B2 | 4/2014 | Stein et al. |
| 8,744,580 | B2 | 6/2014 | Doron et al. |
| 8,814,877 | B2 | 8/2014 | Wasielewski |
| 8,911,448 | B2 | 12/2014 | Stein |
| 8,956,418 | B2 | 2/2015 | Wasielewski et al. |
| 9,005,263 | B2 * | 4/2015 | Boyden ................ A61L 2/0011 607/96 |
| 9,380,980 | B2 | 7/2016 | Revie et al. |
| 9,439,797 | B2 | 9/2016 | Baym et al. |
| 9,459,087 | B2 | 10/2016 | Dunbar et al. |
| 9,532,730 | B2 | 1/2017 | Wasielewski |
| 9,622,701 | B2 | 4/2017 | Stein et al. |
| 9,687,670 | B2 | 6/2017 | Dacey, Jr. et al. |
| RE46,582 | E | 10/2017 | Morgan et al. |
| 9,839,374 | B2 | 12/2017 | Roche et al. |
| 10,034,779 | B2 | 7/2018 | Chen et al. |
| 10,080,509 | B2 | 9/2018 | Wasielewski |
| 10,188,464 | B2 | 1/2019 | Britton et al. |
| 10,219,696 | B2 | 3/2019 | Araci et al. |
| 10,234,934 | B2 | 3/2019 | Connor |
| 10,492,686 | B2 | 12/2019 | Hunter et al. |
| 10,531,826 | B2 | 1/2020 | Wasielewski et al. |
| 10,582,896 | B2 | 3/2020 | Revie et al. |
| 10,660,760 | B2 | 5/2020 | Johannaber et al. |
| 10,667,745 | B2 | 6/2020 | Anker et al. |
| 10,792,162 | B2 | 10/2020 | Johannaber et al. |
| 10,842,636 | B2 | 11/2020 | Johannaber et al. |
| 10,898,106 | B2 | 1/2021 | Bodewes et al. |
| 10,966,788 | B2 | 4/2021 | Britton et al. |
| 11,027,140 | B2 | 6/2021 | Wang et al. |
| 11,071,456 | B2 | 7/2021 | Hunter et al. |
| 11,134,870 | B2 | 10/2021 | Lieb et al. |
| 11,234,825 | B2 | 2/2022 | Johannaber et al. |
| 11,234,852 | B2 | 2/2022 | Koo |
| 11,389,111 | B2 | 7/2022 | Bae |
| 2004/0158294 | A1 | 8/2004 | Thompson |
| 2004/0243148 | A1 | 12/2004 | Wasielewski |
| 2005/0010301 | A1 | 1/2005 | Disilvestro et al. |
| 2006/0047283 | A1 | 3/2006 | Evans et al. |
| 2006/0271199 | A1 | 11/2006 | Johnson |
| 2007/0005141 | A1 | 1/2007 | Sherman |
| 2007/0089518 | A1 | 4/2007 | Ericson et al. |
| 2007/0239165 | A1 | 10/2007 | Amirouche |
| 2008/0033527 | A1 | 2/2008 | Nunez et al. |
| 2008/0065225 | A1 | 3/2008 | Wasielewski et al. |
| 2008/0077016 | A1 | 3/2008 | Sparks et al. |
| 2010/0171394 | A1 | 7/2010 | Glenn et al. |
| 2010/0204551 | A1 | 8/2010 | Roche |
| 2010/0204802 | A1 | 8/2010 | Wilson et al. |
| 2010/0249576 | A1 | 9/2010 | Askarinya et al. |
| 2014/0303739 | A1 | 10/2014 | Mentink et al. |
| 2016/0015319 | A1 | 1/2016 | Billi et al. |
| 2016/0029952 | A1 | 2/2016 | Hunter |
| 2016/0089079 | A1 | 3/2016 | Stein |
| 2016/0192878 | A1 | 7/2016 | Hunter |
| 2016/0242646 | A1 | 8/2016 | Obma |
| 2016/0302721 | A1 | 10/2016 | Wiedenhoefer et al. |
| 2016/0338644 | A1 | 11/2016 | Connor |
| 2017/0065436 | A1 | 3/2017 | Singh et al. |
| 2017/0196508 | A1 | 7/2017 | Hunter |
| 2017/0231559 | A1 | 8/2017 | Cuevas et al. |
| 2017/0296118 | A1 | 10/2017 | Swanson et al. |
| 2017/0319141 | A1 | 11/2017 | Revie et al. |
| 2017/0340243 | A1 | 11/2017 | Jain et al. |
| 2018/0116805 | A1 | 5/2018 | Johannaber et al. |
| 2018/0160966 | A1 | 6/2018 | Inan et al. |
| 2018/0235514 | A1 | 8/2018 | DiSilvestro et al. |
| 2019/0167447 | A1 | 6/2019 | Angibaud |
| 2019/0167988 | A1 | 6/2019 | Shahriari et al. |
| 2019/0283247 | A1 | 9/2019 | Chang et al. |
| 2019/0298998 | A1 | 10/2019 | Coleman et al. |
| 2019/0336049 | A1 | 11/2019 | Shah et al. |
| 2019/0350523 | A1 | 11/2019 | Bailey et al. |
| 2020/0000400 | A1 | 1/2020 | McKinnon et al. |
| 2020/0178898 | A1 | 6/2020 | Revie et al. |
| 2020/0383796 | A1 | 12/2020 | Johannaber et al. |
| 2021/0022874 | A1 | 1/2021 | Johannaber et al. |
| 2021/0059554 | A1 | 3/2021 | Armbruster |
| 2021/0141034 | A1 | 5/2021 | Sharma et al. |
| 2021/0153947 | A1 | 5/2021 | Britton et al. |
| 2021/0186454 | A1 | 6/2021 | Behzadi et al. |
| 2021/0228160 | A1 | 7/2021 | Braganza et al. |
| 2021/0290063 | A1 | 9/2021 | Roche |
| 2021/0366610 | A1 | 11/2021 | Gross et al. |
| 2021/0369471 | A1 | 12/2021 | Gross et al. |
| 2021/0378841 | A1 | 12/2021 | Mokete |
| 2021/0386292 | A1 | 12/2021 | Hunter et al. |
| 2022/0000422 | A1 | 1/2022 | Gross et al. |
| 2022/0015672 | A1 | 1/2022 | Lieb et al. |
| 2022/0047162 | A1 | 2/2022 | Hunter et al. |

FOREIGN PATENT DOCUMENTS

| | | |
|---|---|---|
| WO | 2017096138 A1 | 6/2017 |
| WO | 2021154885 A2 | 8/2021 |

OTHER PUBLICATIONS

(56)  References Cited

OTHER PUBLICATIONS

Arami, A. et al., "Accurate Measurement of Concurrent Flexion-Extension and Internal-External Rotations in Smart Knee Prostheses," IEEE Transactions on Biomedical Engineering, Sep. 2013, 8 pgs.

Brahim A, Jain M, et al., "A Smart Knee Implant Using Triboelectric Energy Harvesters". Smart Mater Struct. Feb. 2019;28(2):025040. doi: 10.1088/1361-665X/aaf3f1. Epub Jan. 25, 2019. 39 pgs.

Bhatnagar, Vikrant & Owende, Philip, "Energy Harvesting for Assistive and Mobile Applications". Energy Science & Engineering. 3. 10.1002/ese3.63. (Feb. 2015). 21 pgs.

Schaufler, Anna, et al. "Sensor-based measurement for advanced monitoring and early detection of PE wear in total knee arthroplasties" Current Directions in Biomedical Engineering, vol. 7, No. 2, Oct. 2021, pp. 283-286. <https://doi.org/10.1515/cdbme-2021-2072>.

* cited by examiner

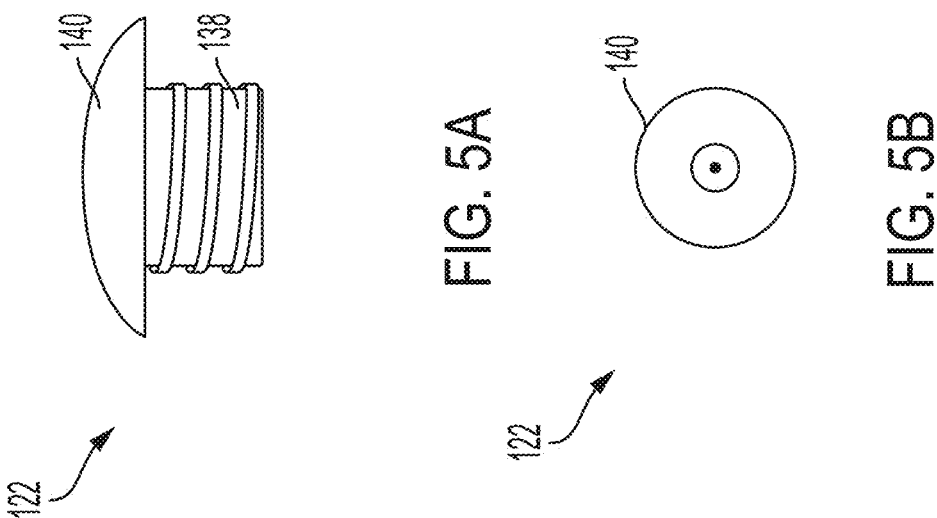
FIG. 5A
FIG. 5B
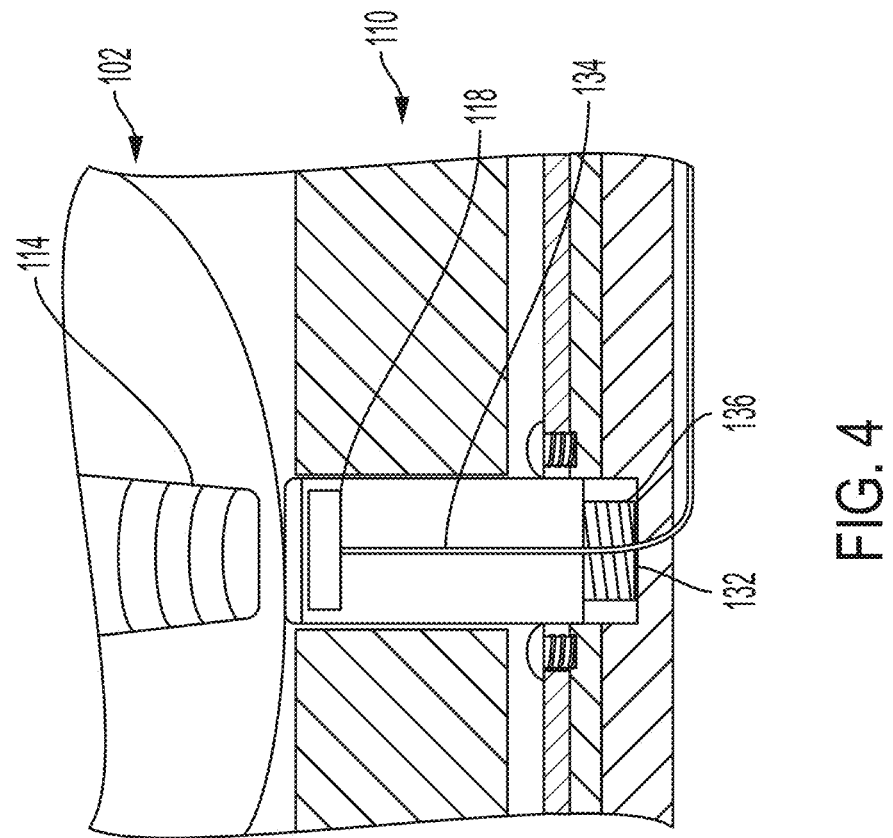
FIG. 4

1210

PRESSURE

IMU

1276

1204

1210

PE

TI

1212

INTRA-OPERATIVE GAP DETECTION

CROSS-REFERENCE TO RELATED APPLICATION

This application is a continuation of U.S. patent application Ser. No. 18/108,954 filed on Feb. 13, 2023, which claims the benefit of the filing date of U.S. Provisional Patent Application No. 63/444,056 filed Feb. 8, 2023, and which claims the benefit of the filing date of U.S. Provisional Patent Application No. 63/444,045, filed Feb. 8, 2023, and which claims the benefit of the filing date of U.S. Provisional Patent Application No. 63/443,146 filed Feb. 3, 2023, and which claims the benefit of the filing date of U.S. Provisional Patent Application No. 63/483,045, filed Feb. 3, 2023, and which claims the benefit of the filing date of U.S. Provisional Patent Application No. 63/482,659, filed Feb. 1, 2023, and which claims the benefit of the filing date of U.S. Provisional Patent Application No. 63/482,656 filed Feb. 1, 2023, and which claims the benefit of the filing date of U.S. Provisional Patent Application No. 63/482,097 filed Jan. 30, 2023, and which claims the benefit of the filing date of U.S. Provisional Patent Application No. 63/482,109 filed Jan. 30, 2023, and which claims the benefit of the filing date of U.S. Provisional Patent Application No. 63/481,660 filed Jan. 26, 2023, and which claims the benefit of the filing date of U.S. Provisional Patent Application No. 63/481,053 filed Jan. 23, 2023, and which claims the benefit of the filing date of U.S. Provisional Patent Application No. 63/431,094 filed Dec. 8, 2022, and which claims the benefit of the filing date of U.S. Provisional Patent Application No. 63/423,932 filed Nov. 9, 2022, and which claims the benefit of the filing date of U.S. Provisional Patent Application No. 63/419,781 filed Oct. 27, 2022, and which claims the benefit of the filing date of U.S. Provisional Patent Application No. 63/419,522 filed Oct. 26, 2022, and which claims the benefit of the filing date of United States Provisional Patent Application No. 63,419,455 filed Oct. 26, 2022, and which claims the benefit of the filing date of U.S. Provisional Patent Application No. 63/359,384 filed Jul. 8, 2022, and which claims the benefit of the filing date of U.S. Provisional Patent Application No. 63/309,809 filed Feb. 14, 2022, the disclosures of all of which are hereby incorporated herein by reference in their entirety.

FIELD OF INVENTION

The present disclosure relates to implants and methods for implant gap detection, and particularly to joint implants and methods for intra-operative implant gap detection.

BACKGROUND OF THE INVENTION

Monitoring patient recovery after joint replacement surgery is critical for proper patient rehabilitation. A key component of monitoring a patient's recovery is evaluating the performance of the implant to detect implant dislocation, implant wear, implant malfunction, implant breakage, etc. For example, a tibial insert made of polyethylene ("PE") implanted in a total knee arthroscopy ("TKA") is susceptible to macroscopic premature failure due to excessive loading and mechanical loosening. Early identification of improper implant functioning and/or infection and inflammation at the implantation site can lead to corrective treatment solutions prior to implant failure. Data relating to postoperative range of motion and load balancing of the new TKA implants can be critical for managing recovery and identification of a proper replacement solution if necessary.

However, diagnostic techniques to evaluate implant performance are generally limited to patient feedback and imaging modalities such as X-ray fluoroscopy or magnetic resonance imaging ("MRI"). Patient feedback can be misleading in some instances. For example, gradual implant wear or dislocation, onset of infection, etc., may be imperceptible to a patient. Further, imaging modalities offer only limited insight into implant performance. For example, X-ray images will not reveal information related to the patient's range of motion or the amount of stress on the knee joint of a patient recovering from a TKA. Furthermore, the imaging modalities may provide only an instantaneous snapshot of the implant performance, and therefore fail to provide continuous real time information related to implant performance.

Therefore, there exists a need for implants and related methods for tracking implant performance.

BRIEF SUMMARY OF THE INVENTION

Disclosed herein are joint implants and methods for tracking joint implant performance.

In accordance with an aspect of the present disclosure a joint implant is provided. A joint implant according to this aspect, may include a first implant coupled to a first bone of a joint and a second implant coupled to a second bone of the joint. The first implant may include at least one marker. The second implant may contact the first implant. The second implant may include at least one marker reader to detect a position of the marker to identify positional data of the first implant with respect to the second implant. The second implant may include at least one load sensor to measure load data between the first and second implants. A processor may be operatively coupled to the marker reader and the load sensor. The processor may simultaneously output the positional data and the load data to an external source.

Continuing in accordance with this aspect, the marker may be a magnet and the marker reader may be a magnetic sensor. The magnetic sensor may be a Hall sensor assembly including at least one Hall sensor. The magnet may be a magnetic track disposed along a surface of the first implant. The first implant may include a first magnetic track extending along a medial side of the first implant and a second magnetic track extending along a lateral side of the first implant.

Continuing in accordance with this aspect, the second implant may include a first Hall sensor assembly on a medial side of the second implant and a second Hall sensor assembly on a lateral side of the second implant. The first Hall sensor assembly may be configured to read a magnetic flux density of the first magnetic track and the second Hall sensor assembly configured to read a magnetic flux density of the second magnetic track.

Continuing in accordance with this aspect, a central portion of the first magnetic track may be narrower than an anterior end and a posterior end of the first magnetic track. The first magnetic track may include curved magnetic lines extending across the first magnetic track.

Continuing in accordance with this aspect, the magnetic sensor may be coupled to the load sensor by a connecting element. The connecting element may be a rod configured to transmit loads from the magnetic sensor to the load sensor. The load sensor may be a strain gauge.

Continuing in accordance with this aspect, the joint may be a knee joint. The first implant may be a femoral implant and the second implant may be a tibial implant. The tibial implant may include a tibial insert and a tibial stem. The marker reader and the processor may be disposed within the tibial insert.

Continuing in accordance with this aspect, the positional data may include any of a knee flexion angle, knee varus-valgus rotation, knee internal-external rotation, knee medial-lateral translation, superior-inferior translation, anterior-posterior translation, and time derivatives thereof. The load data may include any of a medial load magnitude, lateral load magnitude, medial load center and lateral load center. The tibial insert may include any of a pH sensor, a temperature sensor and a pressure sensor operatively coupled to the processor. The tibial insert may include a spectroscopy sensor. The tibial insert may be made of polyethylene.

Continuing in accordance with this aspect, the joint implant may include an antenna to transmit the positional data and the load data to an external source. The external source may be any of a tablet, computer, smart phone, and remote workstation.

In accordance with another aspect of the present disclosure, a joint implant is provided. A joint implant according to this aspect, may include a first implant coupled to a first bone of a joint and a second implant coupled to a second bone of the joint. The first implant may include a plurality of medial markers located on a medial side of the first implant, and a plurality of lateral markers located on a lateral side of the first implant. The second implant may contact the first implant. The second implant may include at least one medial marker reader to identify a position of the medial markers and at least one lateral marker reader to identify a position of the lateral markers. The position of the medial markers and the position of the lateral markers may provide positional data of the first implant with respect to the second implant. The second implant may include a medial load sensor to measure medial load data between the first and second implants on a medial side of the joint implant, a lateral load sensor to measure lateral load data between the first and second implants on a lateral side of the joint implant. A processor may be operatively coupled to the medial marker reader, the lateral marker reader, the medial load sensor, and the lateral load sensor. The processor may simultaneously output the positional data, the medial load data, and the lateral load data to an external source.

Continuing in accordance with this aspect, a number of medial markers may be different from a number of lateral markers. The medial markers and the lateral markers may include magnets located at discrete locations on the first implant. The medial marker reader and the lateral marker reader may include a Hall sensor assembly with at least one Hall sensor. The medial load sensor and the lateral load sensor may include piezo stacks.

Continuing in accordance with this aspect, the joint implant may include a battery disposed within the second implant. The joint implant may include a charging circuit disposed within the second implant to charge the battery using power generated by the piezo stacks during loading between the first and second implants.

Continuing in accordance with this aspect, the joint may be a knee joint. The first implant may be a femoral implant and the second implant may be a tibial implant. The tibial implant may include a tibial insert and a tibial stem. The marker reader and the processor may be disposed within the tibial insert. The positional data may include any of a knee flexion angle, knee varus-valgus rotation, knee internal-external rotation, knee medial-lateral translation, anterior-posterior translation, superior-inferior translation, and time derivatives thereof.

Continuing in accordance with this aspect, the medial load data may include a medial load magnitude and a medial load center. The tibial insert may include any of a pH sensor, a temperature sensor, accelerometer, gyroscope, inertial measure unit and a pressure sensor operatively coupled to the processor. The tibial insert may include a spectroscopy sensor.

In accordance with another aspect of the present disclosure, a joint implant system is provided. A joint implant system according to this aspect, may include a first implant coupled to a first bone of a joint, a second implant coupled to a second bone of the joint, and an external sleeve configured to be removably attached to the joint. The first implant may include at least one marker. The second implant may contact the first implant. The second implant may include at least one marker reader to detect a position of the marker to identify positional data of the first implant with respect to the second implant. The second implant may include at least one load sensor to measure load data between the first and second implants. A processor may be operatively coupled to the marker reader and the load sensor. The processor may be configured to simultaneously output the positional data and the load data to an external source.

Continuing in accordance with this aspect, the joint implant system may include a battery to power the marker reader and the processor. The battery may be disposed within the second implant and including a joint implant charging coil. The external sleeve may include an external charging coil to charge the battery. The battery may be configured to be charged by ultrasonic wireless charging or optical charging.

In another aspect of the present disclosure, a method for monitoring a joint implant performance is provided. A method according to this aspect, may include the steps of providing a first implant couplable to a first bone of a joint, providing a second implant couplable to a second bone of the joint, tracking magnetic flux density magnitudes over time using a magnetic sensor, and initiating a warning when a tracked magnetic flux density magnitude is different from a predetermined value. The first implant may include at least one magnetic marker. The second implant may be configured to contact the first implant. The second implant may include at least one magnetic sensor to detect the magnetic flux density of the magnetic marker. The magnetic flux density value may be proportional to a thickness of the second implant.

In accordance with another aspect of the present disclosure, a method for monitoring a joint implant performance is provided. A method according to this aspect, may include the steps of providing a first implant couplable to a first bone of a joint, providing a second implant couplable to a second bone of the joint, tracking a rate of change of a magnetic flux density over time using a magnetic sensor, and initiating a warning when a tracked rate of change of the magnetic flux density exceeds a predetermined value. The first implant may include at least one magnetic marker. The second implant may be configured to contact the first implant. The second implant may include at least one magnetic sensor to detect the magnetic flux density of the magnetic marker. The rate of change of the magnetic flux density may be proportional to a wear rate of the second implant.

In accordance with another aspect of the present disclosure, a method of monitoring implant performance is provided. A method according to this aspect, may include the steps of providing an implant with a first sensor to detect implant temperature, a second sensor to detect a fluid pressure, and a third sensor to detect implant alkalinity, tracking and outputting implant temperature, implant pressure and implant alkalinity over time to an external source using a processor disposed within the implant, and initiating a notification when any of the implant temperature, implant pressure and implant alkalinity, or any combination thereof, exceeds a predetermined value. The implant temperature, implant pressure and implant alkalinity may be related to any of an implant failure and an implant infection. The fluid pressure may be a synovial fluid pressure.

In accordance with an aspect of the present disclosure a method for monitoring a joint implant performance is provided. A method according to this aspect, may include the steps of coupling a first implant to a first bone of a joint, the first implant may include at least one magnetic marker, coupling a second implant to a second bone of the joint, the second implant may include at least one magnetic sensor to detect a position of the magnetic marker, performing a first joint stress test to measure a baseline joint stability value, the baseline joint stability value may be generated by the at least one magnetic sensor, performing a second joint stress test to measure a second joint stability value, the second joint stability value may be generated by the at least one magnetic sensor, and determining joint stability of the joint by comparing the baseline joint stability value to the second joint stability value.

Continuing in accordance with this aspect, the joint may be any of a knee joint, shoulder joint, and hip joint.

Continuing in accordance with this aspect, the joint may be a knee joint. The first implant may be a femoral implant and the second implant may be a tibial insert. The first bone may be a femur and the second bone may be a tibia. The first joint stress test and second joint stress test may be any of a varus-valgus stress test, anterior-posterior drawer stress test and flexion-extension stress test. The first joint stress test may be performed intra-operatively. The second joint stress test may be performed post-operatively on the implanted joint implant. The baseline joint stability value and the second joint stability value are tibiofemoral gaps between the femoral implant and the tibial insert measured by the at least one magnetic sensor. A difference between the baseline joint stability value and the second joint stability value below a predetermined threshold may indicate a stable joint. A difference between the baseline joint stability value and the second joint stability value exceeding the predetermined threshold may indicate an unstable joint.

In accordance with another aspect of the present disclosure, a method for monitoring a joint implant performance is provided. A method according to this aspect, may include the steps of coupling a first implant to a first bone of a joint, coupling a second implant to a second bone of the joint, the second implant may include a plurality of load sensors to detect a load and contact points between the first and second implants, performing a first joint stress test to measure a baseline joint stability value, the baseline joint stability value may be generated by the load sensors, performing a second joint stress test to measure a second joint stability value, the second joint stability value may be generated by the load sensors, and determining joint stability of the joint by comparing the baseline joint stability value to the second joint stability value.

Continuing in accordance with this aspect, the joint may be any of a knee joint, shoulder joint, and hip joint.

Continuing in accordance with this aspect, the joint may be a knee joint. The first implant may be a femoral implant and the second implant may be a tibial insert. The first bone may be a femur and the second bone may be a tibia.

Continuing in accordance with this aspect, the first joint stress test and second joint stress test may be any of an internal-external rotational torque test, anterior-posterior shear force test and flexion-extension stress test. The first joint stress test may be performed intra-operatively. The second joint stress test may be performed post-operatively on the implanted joint implant. The baseline joint stability value and the second joint stability value may be load contact points between a medial and lateral condyle of the femoral implant and the tibial insert measured by the load sensors.

Continuing in accordance with this aspect, a difference between the baseline joint stability value and the second joint stability value under a predetermined threshold may indicate a stable joint.

Continuing in accordance with this aspect, a difference between the baseline joint stability and the second joint stability exceeding the predetermined threshold may indicate an unstable joint.

In accordance with another aspect of the present disclosure, a method for monitoring a joint implant performance is provided. A method according to this aspect, may include the steps of coupling a first implant to a first bone of a joint, coupling a second implant to a second bone of the joint, the second implant may include a plurality of load sensors to detect a load and contact points between the first and second implants, establishing a baseline joint stability value, performing a post-operative joint stress test to measure a second joint stability value, the second joint stability value may be generated by the load sensors, and determining joint stability of the joint by comparing the baseline joint stability value to the second joint stability value.

Disclosed herein are joint implants and methods for intra-operatively detecting joint implant gaps.

In accordance with an aspect of the present disclosure, a method for detecting joint implant gap is provided. A method according to this aspect, may include the steps of coupling a first implant to a first bone of a joint, the first implant may include at least one magnetic marker, coupling a second implant to a second bone of the joint, the second implant may be configured to contact the first implant, the second implant may include at least one magnetic sensor to detect a magnetic flux density of the magnetic marker, measuring an amplitude of the magnetic flux density using the magnetic sensor, and determining a gap between the first implant and the second implant from the measured amplitude of the magnetic flux density.

Continuing in accordance with this aspect, the steps of measuring the amplitude of the magnetic flux density and determining the gap between the first implant and the second implant may be performed intra-operatively. The step of determining the gap between the first implant and the second implant may be performed by comparing the measured amplitude of the magnetic flux density to a predetermined value. The predetermined value may be stored in a database. The database may include a library of magnetic flux density amplitude and corresponding gap distances.

Continuing in accordance with this aspect, the method may further include a step of initiating a warning when the measured amplitude of magnetic flux does not match the predetermined value. The joint implant may be any of a knee joint implant, shoulder implant, hip implant and spine implant.

Continuing in accordance with this aspect, the joint implant may be a knee joint implant. The first implant may be a femoral implant and the second implant may be a tibial implant.

Continuing in accordance with this aspect, the method may further comprise a step of performing a varus-valgus movement to determine femoral and tibial implant lift off.

Continuing in accordance with this aspect, the first implant may include a medial magnetic marker and a lateral magnetic marker and the second implant may include a medial magnetic sensor and a lateral magnetic sensor.

Continuing in accordance with this aspect, the step of measuring the amplitude may include measuring an amplitude of the medial magnetic flux of the medial magnetic marker by the medial magnetic sensor and an amplitude of the lateral magnetic flux of the lateral magnetic marker by the lateral magnetic sensor. The step of determining the gap may include determining a medial gap between a medial portion of the first implant and the second implant from the measured amplitude of the medial magnetic flux density and determining a lateral medial gap between a lateral portion of the first implant and the second implant from the measured amplitude of the lateral magnetic flux density.

Continuing in accordance with this aspect, the steps of measuring the amplitude of the magnetic flux density and determining the gap between the first implant and the second implant may be performed post-operatively.

In accordance with another aspect of the present disclosure, a method for detecting joint gap is provided. A method according to this aspect, may include the steps of coupling a first implant to a first bone of a joint, the first implant may include a light source, coupling a second implant to a second bone of the joint, the second implant may be configured to contact the first implant, the second implant may include a pattern, transmitting light from the light source through the pattern, reading the light passing through the pattern from a reader disposed on the first implant, and determining a gap between the first implant and the second implant from the light passing through the pattern.

Continuing in accordance with this aspect, the steps of transmitting the light, reading the light passing through the pattern and determining the gap between the first implant and the second implant may be performed intra-operatively. The step of determining the gap between the first implant and the second implant may be performed by comparing a formed pattern generated by the light passing through the pattern to a predetermined pattern. The predetermined pattern may be stored in a database. The database may include a library of predetermined patterns and corresponding gap distances.

Continuing in accordance with this aspect, the method may further include a step of initiating a warning when the formed pattern does not match the predetermined pattern. The joint implant may be any of a knee joint implant, shoulder implant, hip implant and spine implant.

Continuing in accordance with this aspect, the joint implant may be a knee joint implant. The first implant may be a femoral implant and the second implant may be a tibial implant.

In accordance with another aspect of the present disclosure, a method for detecting joint implant gap is provided. A method according to this aspect, may include the steps of measuring an amplitude of a magnetic flux density using a magnetic sensor associated with a second implant on a second bone of a joint, and determining a gap between the first implant and the second implant from the measured amplitude of the magnetic flux density. The magnetic sensor may detect a magnetic flux density of a magnetic marker associated with a first implant on a first bone of the joint.

Continuing in accordance with this aspect, a position of the first implant with respect to the second implant may be determined by the gap between the first implant and the second implant.

BRIEF DESCRIPTION OF THE DRAWINGS

A more complete appreciation of the subject matter of the present disclosure and the various advantages thereof can be realized by reference to the following detailed description, in which reference is made to the following accompanying drawings:

FIG. 4 is a partial view of an encoder read head and a load sensor of a tibial implant of the knee joint implant of FIG. 1;

FIG. 5A is a front view of an antenna of the knee joint implant of FIG. 1;

FIG. 5B is a top view of the antenna of FIG. 5A;

DETAILED DESCRIPTION

Reference will now be made in detail to the various embodiments of the present disclosure illustrated in the accompanying drawings. Wherever possible, the same or like reference numbers will be used throughout the drawings to refer to the same or like features within a different series of numbers (e.g., 100-series, 200-series, etc.). It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described.

As used herein, the terms "load" and "force" will be used interchangeably and as such, unless otherwise stated, the explicit use of either term is inclusive of the other term. Similarly, the terms "magnetic markers" and "markers" will be used interchangeably and as such, unless otherwise stated, the explicit use of either term is inclusive of the other term.

As used herein, the terms "power" and "energy" will be used interchangeably and as such, unless otherwise stated, the explicit use of either term is inclusive of the other term. Similarly, the terms "implant" and "prosthesis" will be used interchangeably and as such, unless otherwise stated, the explicit use of either term is inclusive of the other term. The term "joint implant" means a joint implant system comprising two or more implants. Similarly, the terms "energy generator" and "energy harvester" will be used interchangeably and as such, unless otherwise stated, the explicit use of either term is inclusive of the other term.

In describing preferred embodiments of the disclosure, reference will be made to directional nomenclature used in describing the human body. It is noted that this nomenclature is used only for convenience and that it is not intended to be limiting with respect to the scope of the present disclosure. As used herein, when referring to bones or other parts of the body, the term "anterior" means toward the front part of the body or the face, and the term "posterior" means toward the back of the body. The term "medial" means toward the midline of the body, and the term "lateral" means away from the midline of the body. The term "superior" means closer to the head, and the term "inferior" means more distant from the head.

Figure 1:
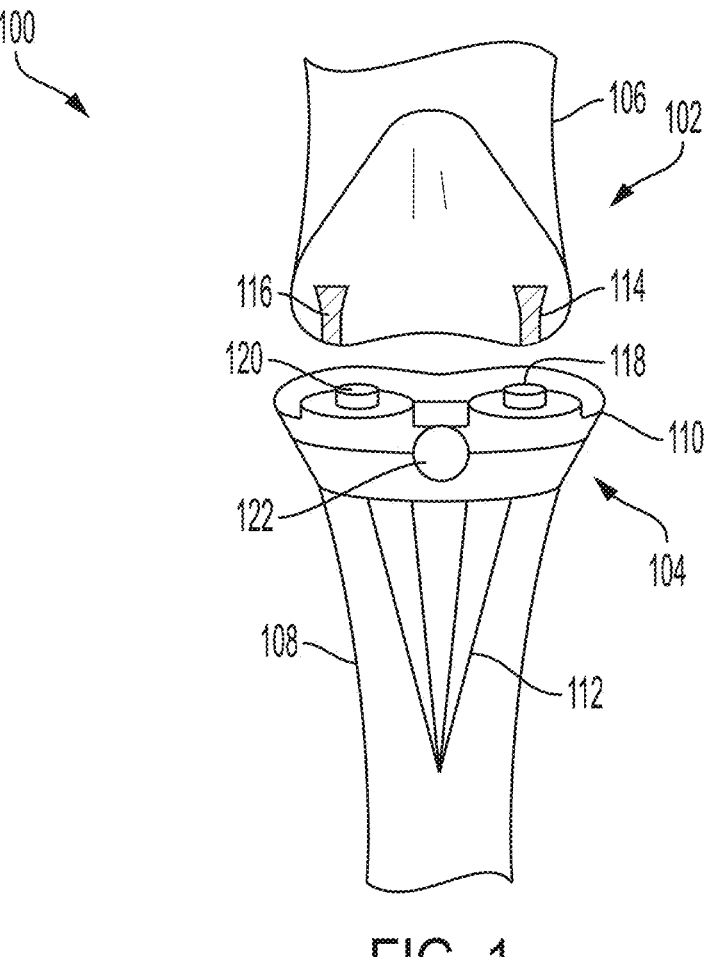
FIG. 1 is a front view of a knee joint implant according to an embodiment of the present disclosure.

FIG. 1 is a front view of a knee joint implant 100 according to an embodiment of the present disclosure. Knee joint implant 100 includes a femoral implant 102 located on a femur 106 and a tibial implant 104 located on a tibia 108. Tibial implant 104 has a tibial insert 110 configured to contact femoral implant 102, and a tibial baseplate or tibial stem 112 extending distally into tibia 108. Femoral implant 102 includes a medial encoder track 114 located on a medial side and a lateral encoder track 116 on a lateral side of the femoral implant. While the encoder tracks are shown along a surface of femoral implant 102 in FIG. 1, these tracks can be located within or partially within a femoral implant on the medial and lateral sides thereof in other embodiments. The encoder tracks can be made of various structures, including magnetic tape of varying lengths and magnetic markers positioned at discrete locations. The resolution of the encoder track can be adjusted depending on the required precision of the measured parameters such as joint displacement, joint rotation, joint slip, etc. Tibial insert 110 includes a medial read head 118 and lateral read head 120 to read a magnetic flux density from medial encoder track 114 and lateral encoder track 116, respectively. Medial read head 118 and lateral read head 120 can be any suitable magnetometer configured to detect and measure magnetic flux density, such as a Hall effect sensor. As tibia 108 rotates with reference to femur 106 during knee flexion and extension, medial encoder track 114 and lateral encoder track 116 move along medial read head 118 and lateral read head 120, respectively. This movement causes a change in magnetic flux density which is detected by read heads 118, 120, and can be utilized to measure knee joint implant 100 movement, rotation, speed and range of articulation, motion/activity, joint slip, and other motion related information. The magnetic-mechanic coupling of the read heads with the encoder tracks allows for direct, instantaneous, and continuous measurements of these knee joint implant parameters. A data transmitter such as an antenna 122 located on tibial insert 110 transmits the knee joint implant parameters measured by the read heads via Bluetooth or other similar wireless means to an external source such as a smart phone, tablet, monitor, network, etc. to allow for real time review of the knee joint implant performance.

Figure 2:
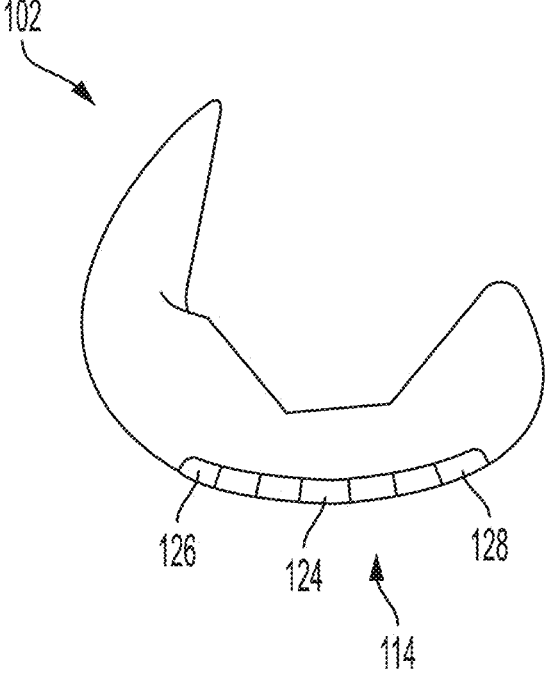
FIG. 2 is a side view of a femoral implant of the knee joint implant of FIG. 1.
Figure 3B:
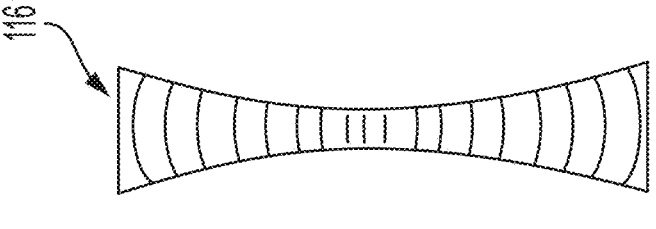
FIG. 3B is schematic view of encoder tracks of the femoral implant of FIG. 2.
Figure 3B:
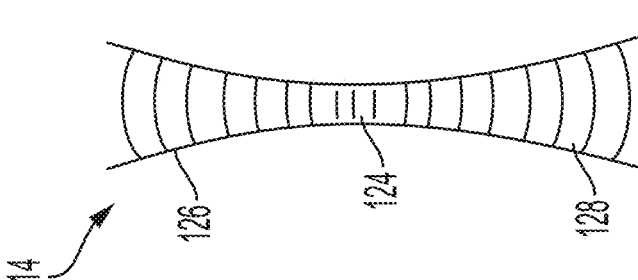
Figure 3A:
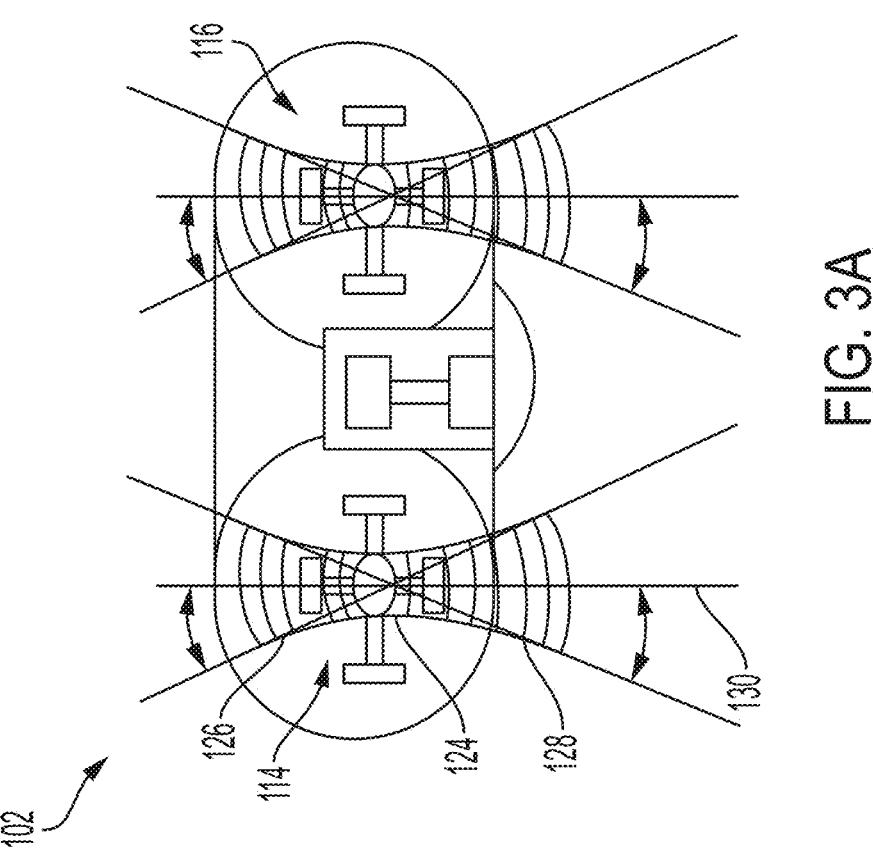
FIG. 3A is a bottom view of the femoral implant of FIG. 2.

FIGS. 2-3B illustrate additional details of femoral implant 102, medial encoder track 114 and lateral encoder track 116. As shown in FIG. 2, medial encoder track 114 extends from an anterior portion 126 of femoral implant 102 to a posterior portion 128 of the femoral implant along a track axis 130. Medial encoder track 114 includes a central portion 124 which is narrower than anterior and posterior portions 126, 128 as shown in FIG. 3A. As shown in FIG. 3B, medial encoder track 114 includes arched or curved magnetic lines to compensate for joint rotations in order to maintain uniform readings during a full range of motion of the knee joint. Similarly, lateral encoder track 116 extends from an anterior portion to a posterior portion of the femoral implant and includes a narrow central portion relative to the anterior and posterior portions with arched or curved magnetic lines. The conical profile and curved magnetic lines of the encoder tracks are configured to compensate for joint rotational motion and maintain alignment and coupling between the read heads and the tracks. This maximizes measurement collection and measurement accuracy during a full range of motion of the knee joint. The shape, size and location of the encoder tracks can vary depending on the implant.

FIG. 4 shows details of a medial side of tibial insert 110. Tibial insert 110 includes a medial load sensor 132 in connection with medial read head 118 via a medial connector 134. Medial load sensor 132 is a load measuring sensor such as a strain gauge or piezoelectric sensor configured to measure loads or forces transmitted from medial read head 118 via medial connector 134. Medial connector 134 can be a rigid member such as a connecting rod to transmit loads from medial read head 118 to medial load sensor 132. As shown in FIG. 4, a portion of the medial side of femoral implant 102 directly contacts medial read head 118 to transmit loads (medial side loads), which is then measured by medial load sensor 132. Medial read head 118 is spring-loaded by a medial load spring 136 located below medial load sensor 132 to ensure contact between medial read head 118 and femoral implant 102. Similarly, a lateral side of tibial insert 110 includes a lateral load sensor, a lateral connector, and a lateral load spring. The lateral load sensor is configured to measure lateral loads between femoral implant 102 and tibial implant 104. Measured medial and lateral loads are transmitted via antenna 122 to an external source. Thus, knee joint implant 100 can simultaneously provide knee motion information (rotation, speed, flexion angle, etc.) and knee load (medial load, medial load center, lateral load, lateral load center, etc.) in real time to an external source.

Details of antenna 122 are shown in FIGS. 5A and 5B. Antenna 122 includes screw threads configured to be attached to tibial insert 110. Antenna 122 can include a coax interface to shield knee joint and improve transmission between knee joint implant 100 and the external source. A battery is located adjacent antenna 122 (not shown) to power knee joint implant 100. Antenna 122 can serve as a charging port via radio frequency (RF) or inductive coupling if a rechargeable battery is used. The location of battery and antenna 122 in tibial insert 110 allow for convenient access to remove and replace these components if necessary. Various other sensors such as a temperature sensor, pressure sensor, accelerometer, gyroscope, magnetometer, pH sensor, etc., can be included in knee joint implant 100 as more fully described below.

Figure 6:
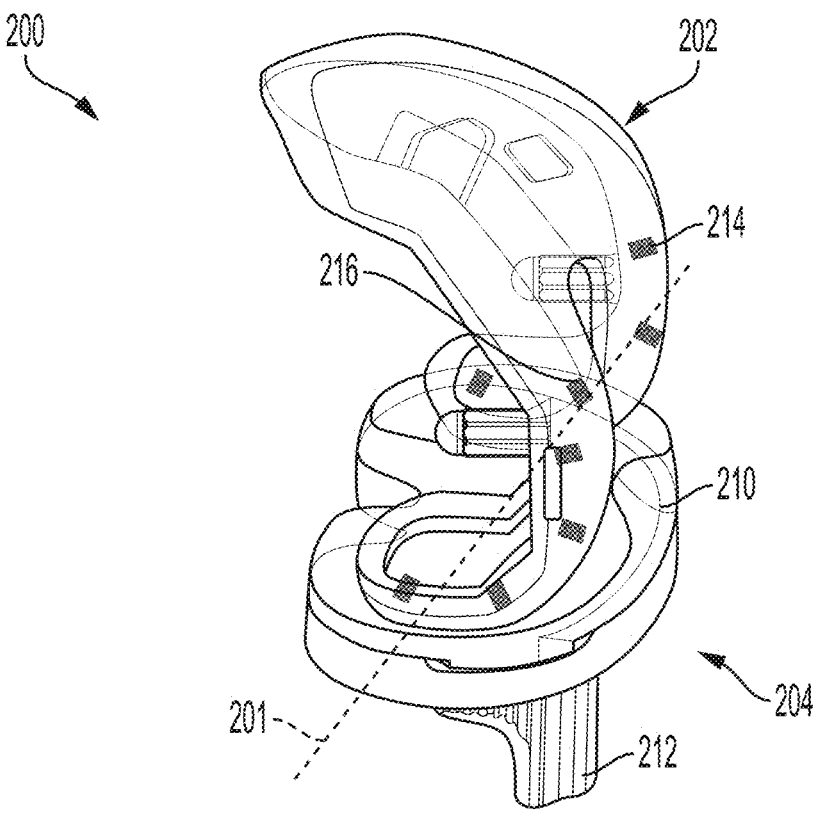
FIG. 6 is a perspective side view of a knee joint implant according to another embodiment of the present disclosure.
Figure 7:
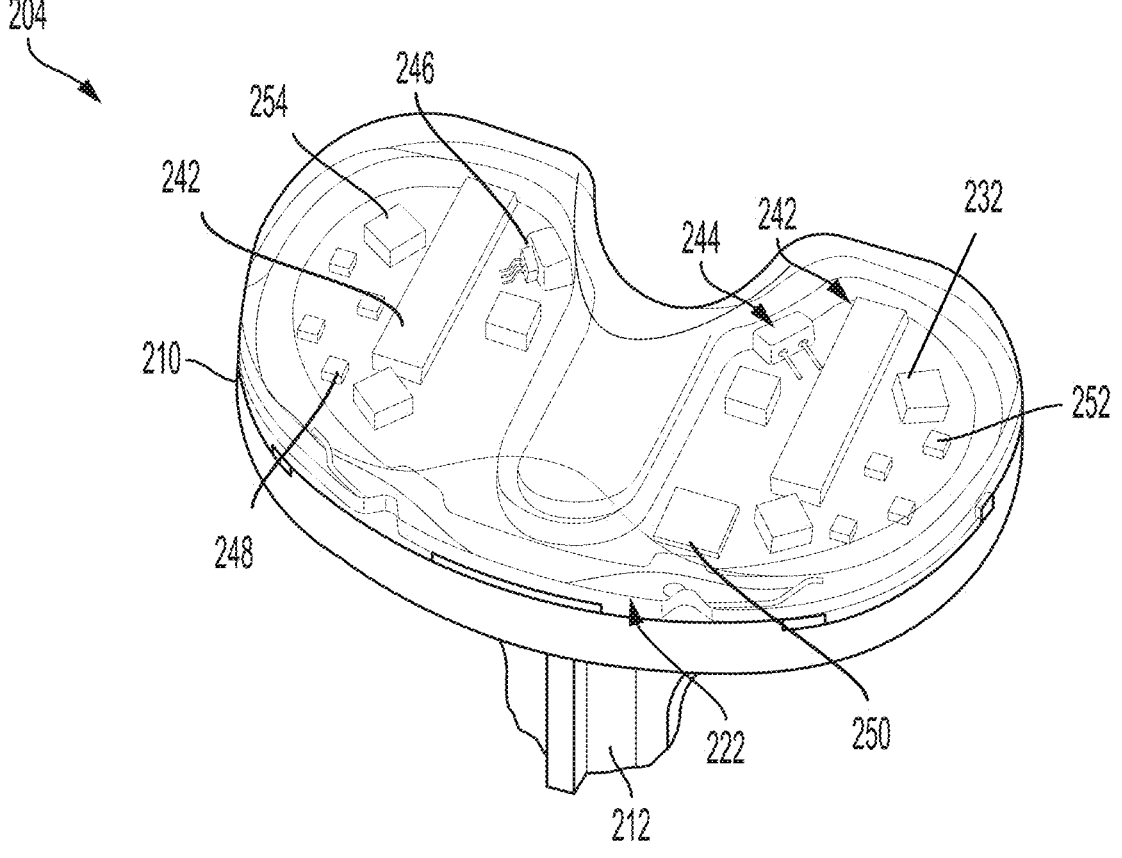
FIG. 7 is a perspective front view of a tibial implant of the knee joint implant of FIG. 6.
Figure 8:
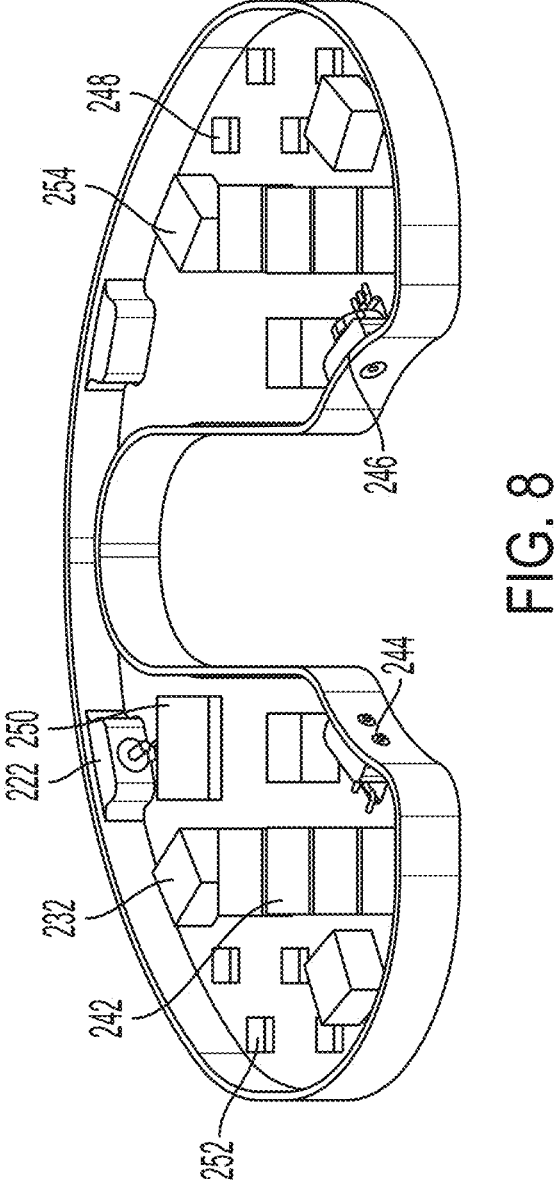
FIG. 8 is a partial perspective view of an insert of the tibial implant of FIG. 6.

FIG. 6 is a perspective side view of a knee joint implant 200 according to another embodiment of the present disclosure. Knee joint implant 200 is similar to knee joint implant 100, and therefore like elements are referred to with similar numerals within the 200-series of numbers. For example, knee joint implant 200 includes a femoral implant 202, a tibial implant 204 with a tibial insert 210 and a tibial stem 212. However, knee joint implant 200 includes magnetic medial markers 214 and magnetic lateral markers 216 located at discrete locations along the medial and lateral sides of femoral implant 202, respectively.

Figure 9:
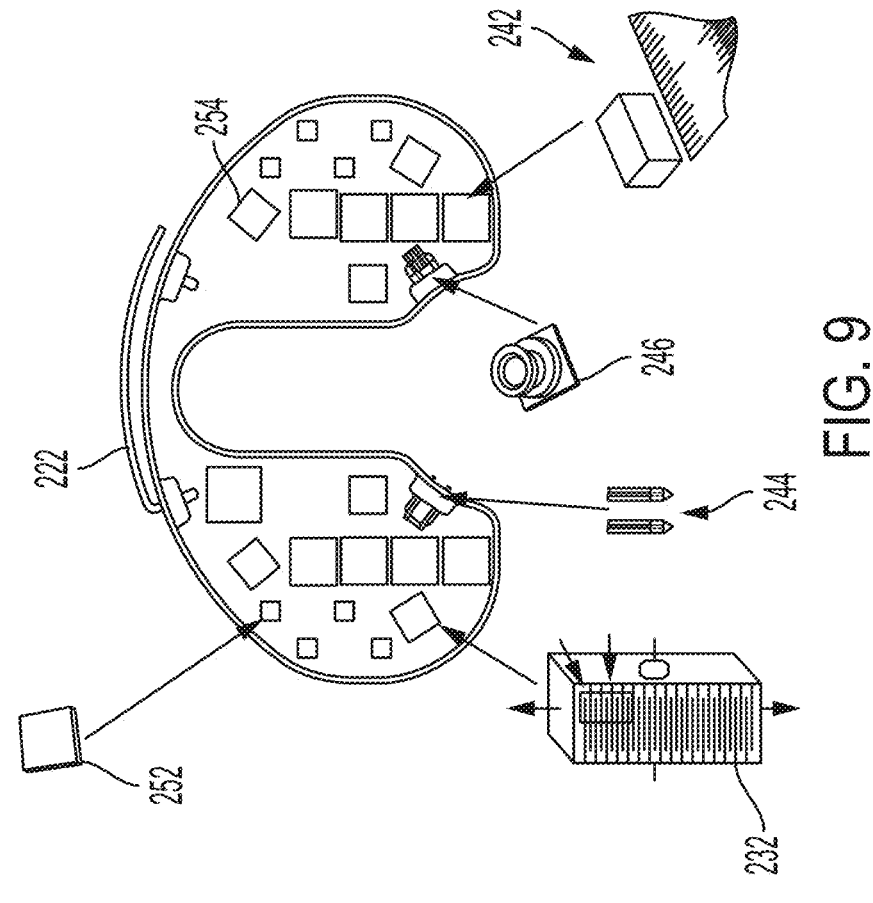
FIG. 9 is a partial top view of the insert of FIG. 8 showing details of various insert components.
Figure 9:

Details of tibial insert 210 are shown in FIGS. 7-11. Tibial insert 210 includes batteries 242 on both medial and lateral sides. Batteries 242 can be solid state batteries, lithium ion batteries, lithium carbon monofluoride batteries, lithium thionyl chloride batteries, lithium ion polymer batteries, etc. As best shown in FIG. 9, Hall sensor assemblies, with each assembly including at least one Hall sensor, are used as a medial marker reader 252 and a lateral marker reader 248 to read medial markers 214 and lateral markers 216, respectively. Each Hall sensor assembly can include multiple Hall sensors arranged in various configurations and orientations. For example, the Hall sensor assembly can include Hall sensors oriented in Cartesian coordinates. As the tibia rotates with reference to the femur during knee flexion and extension, medial markers 214 and lateral markers 216 move along medial marker reader 252 and lateral marker reader 248, respectively. This movement causes a change in magnetic flux density, which is detected by marker readers 252, 248, to measure knee joint implant 200 movement, rotation, speed and range of articulation, motion/activity, joint slip, and other motion related information. The magnetic-mechanic coupling of the marker readers with the markers allows for direct, instantaneous, and continuous measurements of these knee joint implant parameters without the need to process this information via an algorithm or other means. While eight Hall sensor assemblies (four on each side) are shown in this embodiment, other embodiments can have more than eight or less than eight Hall sensor assemblies positioned at various locations. The arrangement of marker readers and markers provide absolute positions of knee joint implant 200 supporting wake-up-and-read kernels. Thus, no inference of movement by data synchronization techniques is required to obtain absolute position data of knee joint implant 200. The number of medial markers 214 can be different from the number of lateral markers 216 to account for variation in signal fidelity between these sides. For example, seven magnetic markers can be provided on the medial side and only four magnet markers can be provided on the lateral side to improve signal fidelity and motion detection precision on the medial side.

As best shown in FIG. 9, three piezo stacks on the medial side serve as medial load sensors 232, and three piezo stacks on the lateral side serve as lateral load sensors 254. The staggered or non-linear arrangement of the three piezo stacks on the medial and lateral sides allow for net load measurements and identification of resultant load centers at the medial and lateral sides. Thus, knee joint implant 200 can simultaneously provide knee motion information (joint rotation, joint speed, joint flexion angle, joint slippage, etc.) and knee load (medial load, medial load center, lateral load, lateral load center, etc.) in real time to an external source. The piezo stacks are configured to generate power from the patient's motion by converting pressure on the piezo stacks to charge batteries 242 as more fully described below. Thus, knee joint implant 200 does not require external charging devices or replacement batteries for the active life of the implant.

Tibial insert 210 includes an infection or injury detection sensor 244. For example, the infection or injury detection can be a pH sensor configured to measured bacterial infection by measuring the alkalinity of synovial fluid to provide early detection of knee joint implant 200 related infection. A temperature and pressure sensor 246 is provided in tibial insert 210 to monitor knee joint implant 200 performance. For example, any increase in temperature and/or pressure may indicate implant-associated infection. Pressure sensor 246 is used to measure synovial fluid pressure in this embodiment. Temperature and/or pressure sensor 246 readings can provide early detection of knee joint implant 200 related infection. Thus, injury detection sensors 244 and 236 provide extended diagnostics with heuristics for first level assessment of infections or injury related to knee joint implant 200. An onboard processor 250 such as a micro-controller unit ("MCU") is used to read sensors 244 and 236 and process results for transmission to an external source. This data can be retrieved, processed, and transferred by the MCU via antenna 222 continuously, at predefined intervals, or when certain alkalinity, pressure, and/or temperature thresholds, or any combinations thereof, are detected.

Figures 10, 11:
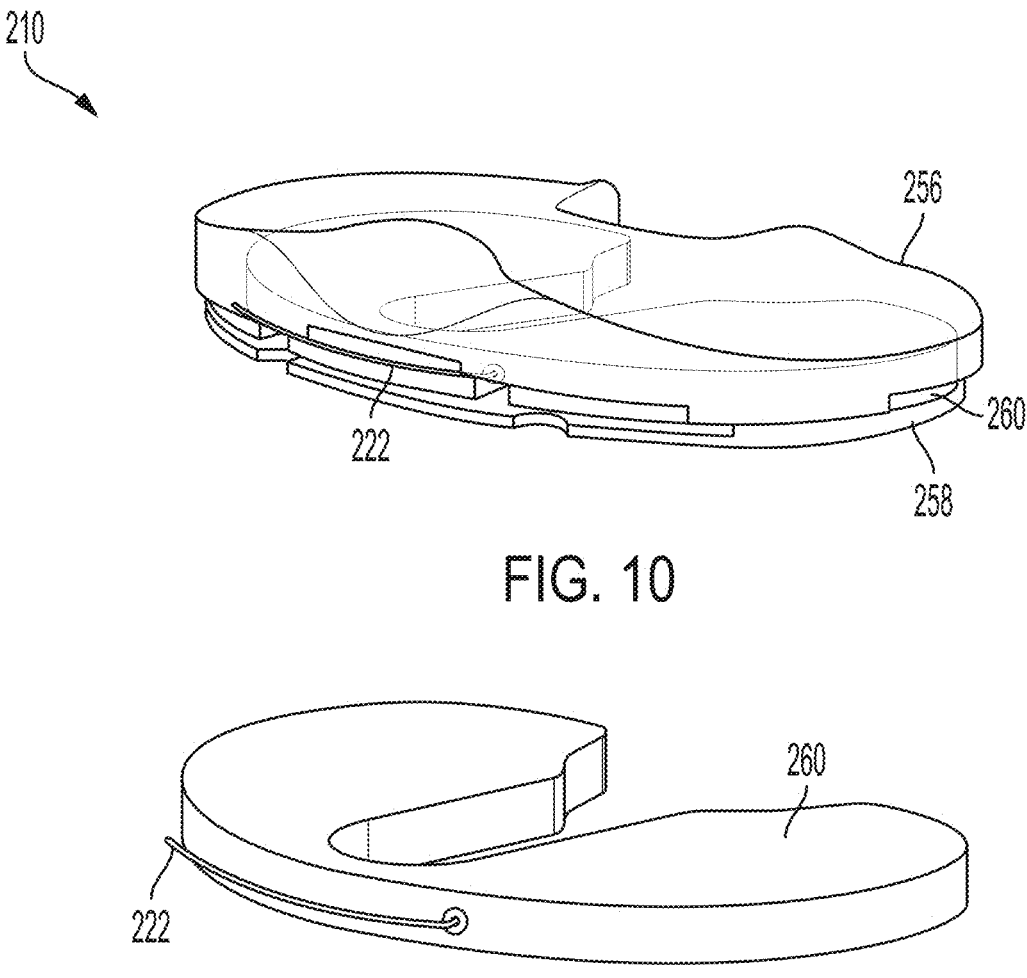
FIG. 10 is a perspective side view of the insert of the tibial implant of FIG. 7.
FIG. 11 is a perspective side view of a cover of the insert of FIG. 10.

The various sensors and electronic components of tibial insert 210 are contained within an upper cover 256 and a lower cover 258 as shown in FIG. 10. The upper and lower covers can be made from a polymer. Antenna 222 is located on an anterior portion of knee joint implant 200 to provide better line of site for transmitting data with less interference. The antenna is fixed inside the polymer covers to provide predictable inductance and capacitance. A cover 260 encloses the sensors and electronic components of tibial insert 210 as shown in FIG. 11. Cover 260 can be a hermetic cover to hermetically seal tibial insert 210. Cover 260 is preferably made of metal and provides radio frequency ("RF") shielding to the knee joint.

The modular design of knee joint implant 200 provides for convenient maintenance of its components. For example, an in-office or outpatient procedure will allow a surgeon to access the tibia below the patella (an area of minimal tissue allowing for fast recovery) to access component of knee joint implant 200. The electronic components and sensors of knee joint are modular and connector-less allowing for convenient replacement of tibial insert 210 or upgrades to same without impacting the femoral implant or the tibial stem.

Figure 12:
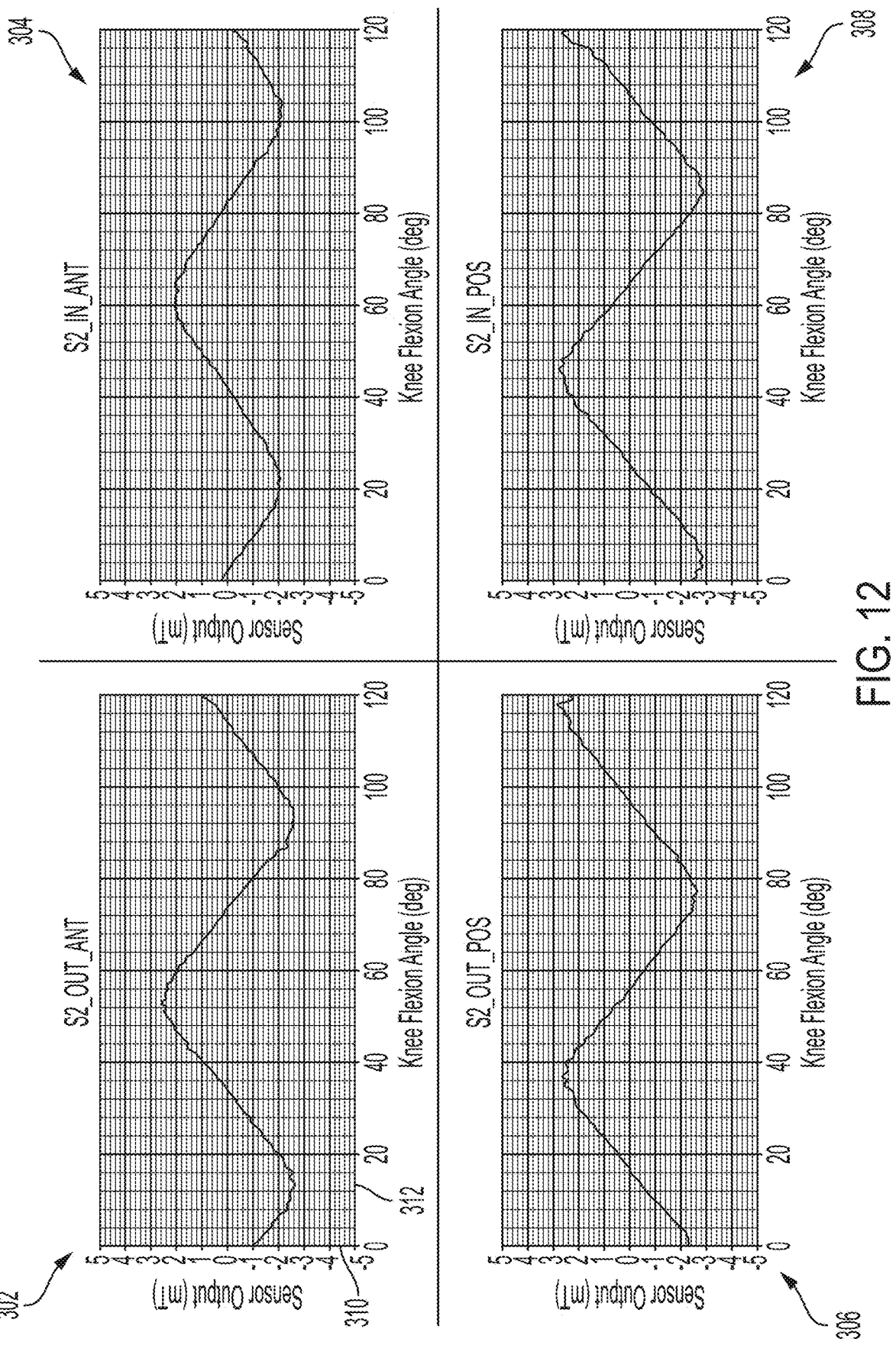
FIG. 12 are graphs showing magnetic flux density measurements of the implant sensors and knee flexion angles.

Graphs plotting magnetic flux density measurements 310 and knee flexion angles 312 are shown in FIG. 12. Magnetic flux density measurements 310 are generated from the magnetic-mechanic coupling of marker readers 248, 252 with the markers 214, 216 as more fully described above. Graphs 302 and 304 show magnetic flux density (mT) measurements from two Hall sensor assemblies (medial marker reader 252 or lateral marker reader 248) for a first range of motion of the knee joint. Similarly, graphs 306 and 308 show magnetic flux density (mT) measurements from two Hall sensors (medial marker reader 252 or lateral marker reader 248) for a second range of motion of the knee joint. The placement of magnetic markers 214, 216 on the femoral component create a sinusoidal magnetic flux density around femoral implant 202. As the femoral implant 202 rotates around an axis of rotation 201 shown in FIG. 6, the marker readers read sine and cosine waveforms. The magnitude of the sine and cosine waves are interpolated to a near linear knee flexion angle. Placing the individual magnetic markers of medial markers 214 and lateral markers 216 at different separation angles on each condyle of femoral implant 202 creates a phase shift in the measurements from one condyle to the next as the knee rotates. This phase shift can then be used to correct for any rollovers in the interpolated waveform. Thus, marker readers 248, 252 and markers 214, 216 serve as an absolute rotation sensor measuring knee flexion through a full range of motion of knee joint implant 200. In addition to the two Hall sensor assemblies on the lateral and medial side of tibial insert 210, the remaining Hall sensor assemblies of marker readers 248, 252 allow for 6-degrees of freedom movement measurements of knee joint implant 200 as more fully explained below. While an absolute magnetic encoder is disclosed in this embodiment, other embodiments can include a knee joint implant with an incremental magnetic encoder.

Figure 13:
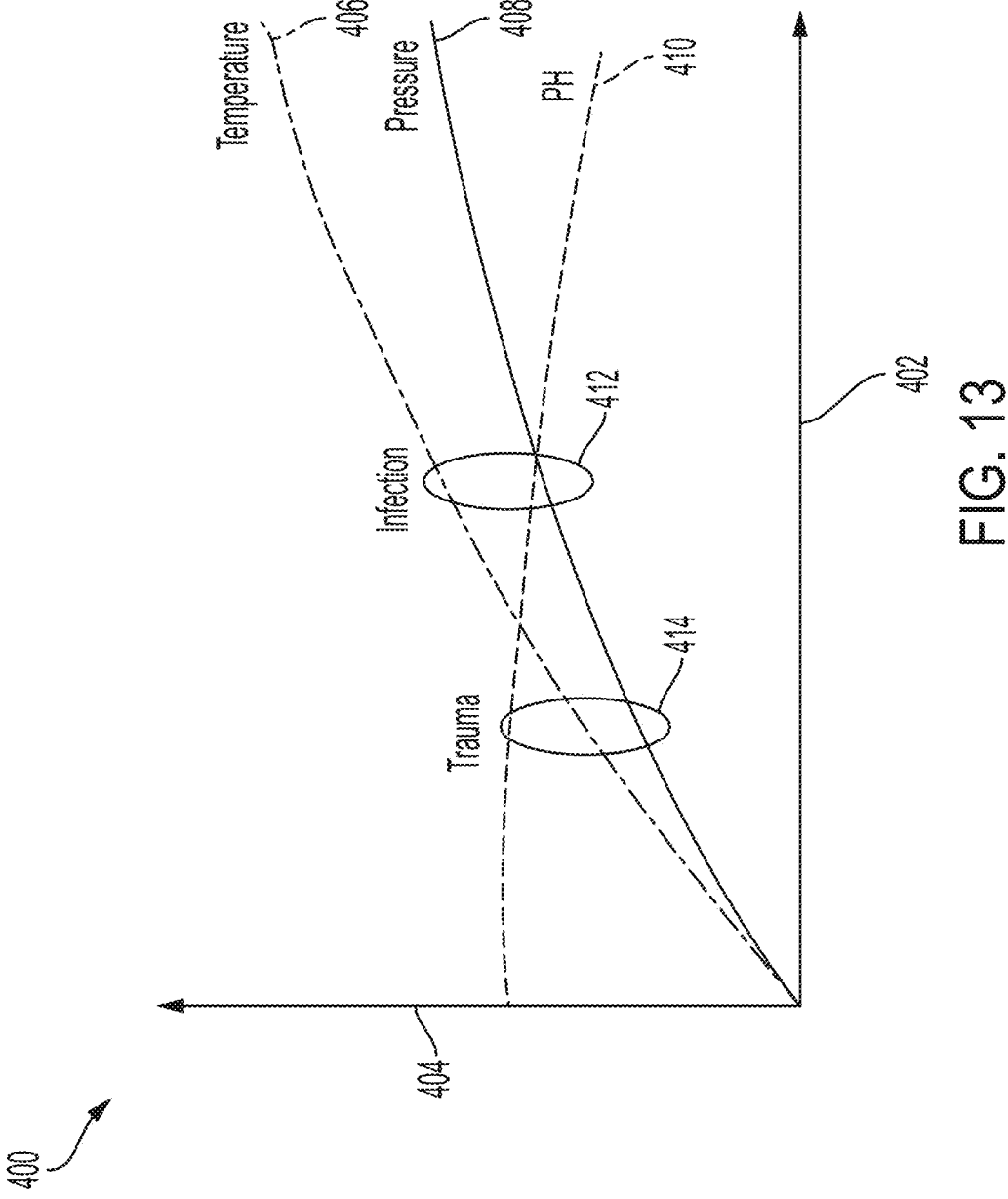
FIG. 13 is a graph showing various implant sensor readings of the knee joint implant of FIG. 6.
Figure 14:
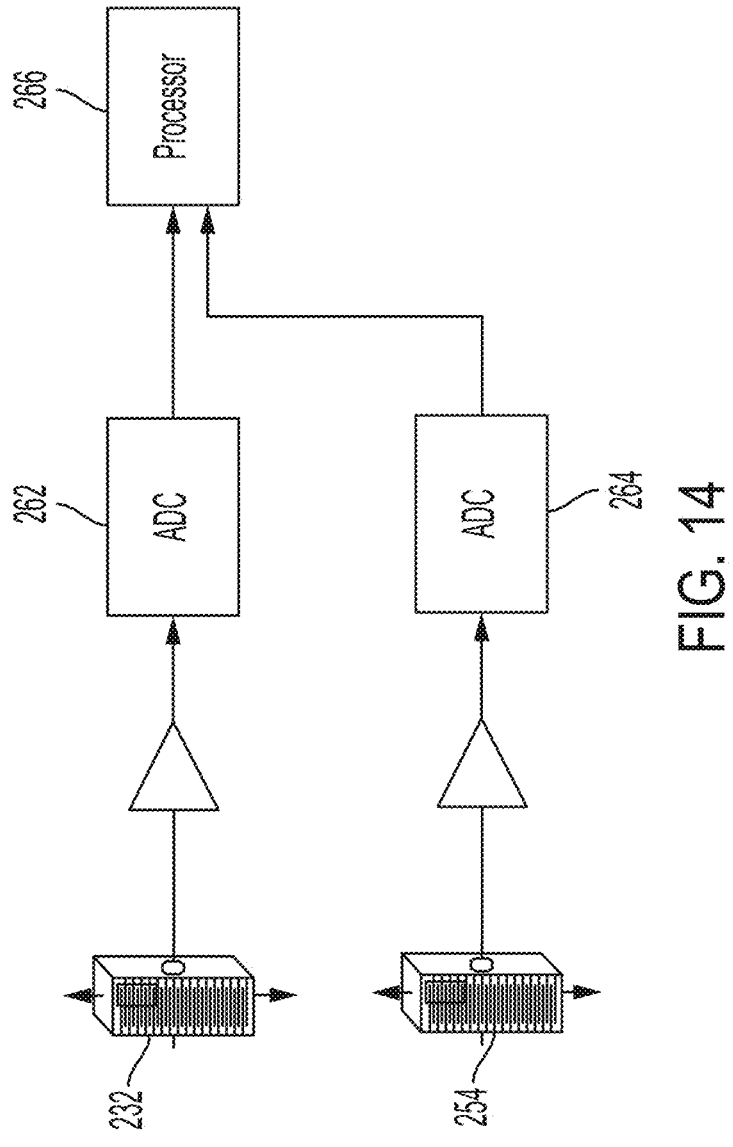
FIG. 14 is a schematic view of implant sensors of the knee joint implant of FIG. 6 in communication with a processor.

FIG. 13 is a graph showing various implant injury detection sensor readings 404 of knee joint implant 200 for early detection of knee joint implant related infection and/or failure. Pressure 408 and temperature 406 are measured using temperature and pressure sensor 246, and alkalinity 410 is measured using pH sensor 244 over time 402. As more fully explained above, alkalinity 410 measurements of joint synovial fluid can indicate bacterial infection to provide early detection of knee joint implant 200 related infection. Increase in pressure 408 and temperature 406 readings may indicate implant-associated infection. Variation or change in synovial fluid pressure 408 may indicate implant malfunction. In addition to predetermined absolute thresholds of the temperature, pressure and alkalinity readings indicating impending infection or implant failure, collective analysis of these readings can offer early detection warning ahead of the failure/infection thresholds. As shown in FIG. 14, a combination of temperature, pressure and alkalinity may indicate early detection of trauma 414 or infection 412. Thus, injury detection sensor readings provide extended diagnostics with heuristics for first level assessment of infections or injury related to knee joint implant 200.

Figure 15:
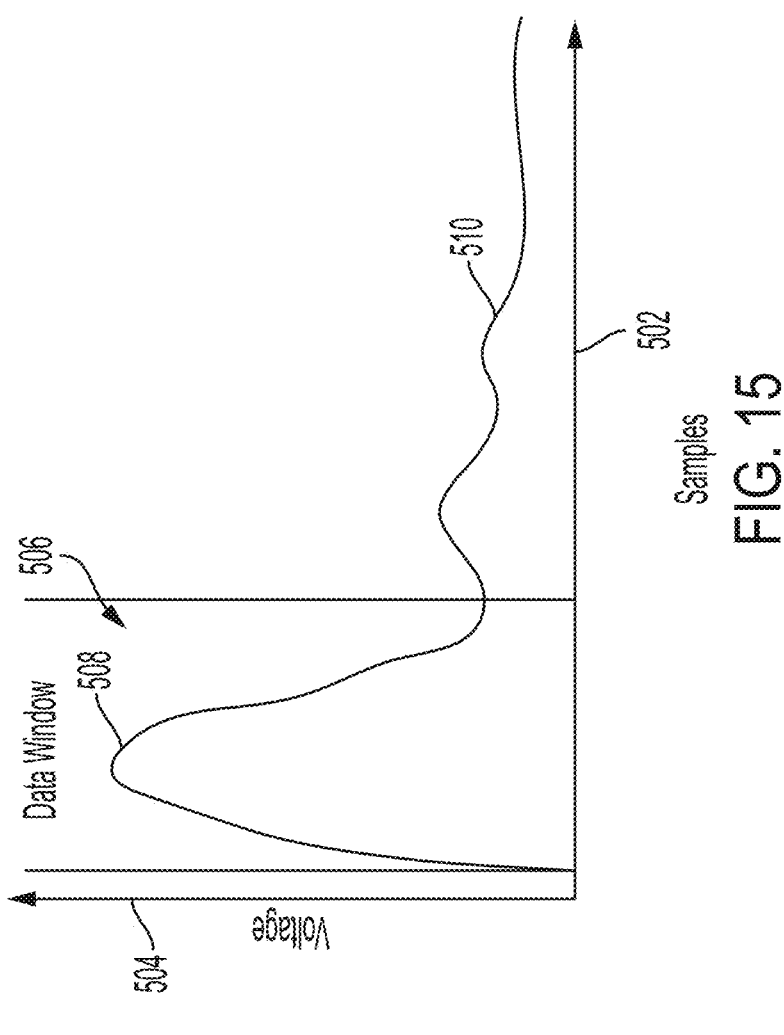
FIG. 15 is a graph showing voltage measurements of the implant sensors.

FIG. 14 is a schematic view of piezo stacks of medial load sensors 232 and lateral load sensor 254 in communication with a processor 266. Analog impulses generated by the piezo stacks when subjected to loading are converted to continuous digital signals via analog-to-digital converters 262 and 264 as shown in FIG. 14. The continuous digital signals (voltage) 508 can be serially loaded into a shift register and measured as shown in a graph 500 of FIG. 15. A sampling window 506 is selected to identify a peak reading 508 to detect knee joint motion. For continuous loading case, such as when a patient is standing, additional sensors such as an inertial measurement unit ("IMU") located in the tibial insert or other locations on knee joint implant 200 can be used to detect or confirm knee joint position. Load data from piezo stacks and IMU measurements can be used to create load and motion profiles for patient-specific or patient-independent analyses.

Figure 16:
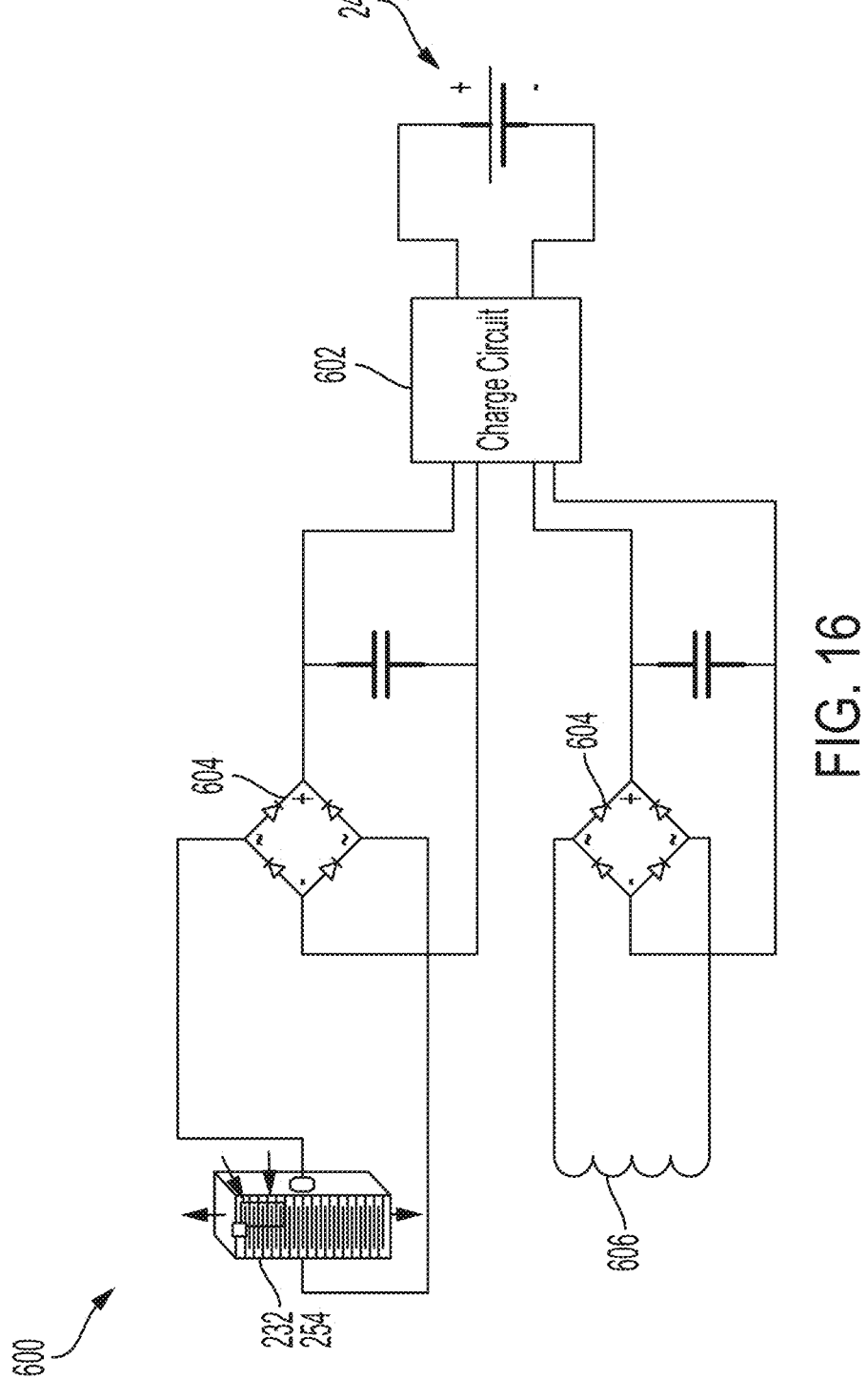
FIG. 16 is a schematic view of a charging circuit for the knee joint implant of FIG. 6.
Figures 17A, 17B:
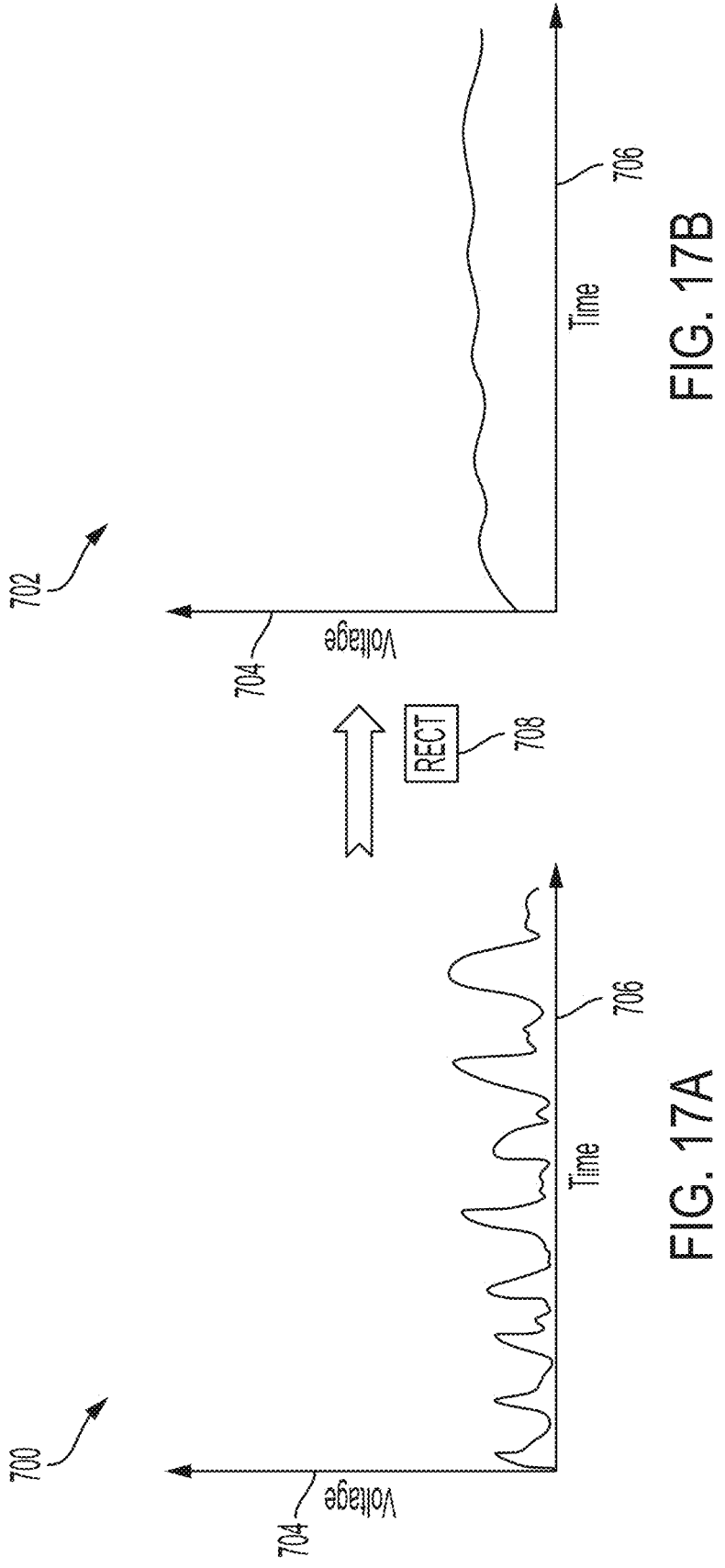
FIG. 17A is a graph showing measured voltage of the implant sensors.
FIG. 17B is a graph showing rectified voltage of the implant sensors.

FIG. 16 is a schematic view of a charging circuit 600 for charging battery 242 of knee joint implant 200. The charging circuit includes a charge circuit 602 connected to a charging coil 606 and piezo stacks of medial load sensors 232 and lateral load sensors 254 via bridge rectifier 604. Charging circuit is configured to direct charge to battery 242 utilizing inputs from one or more piezo stacks from the medial or lateral load sensors. This allows for singular or combined charging using individual or multiple piezo stacks. A minimum voltage output threshold of the piezo stacks can be predetermined to initiate battery charging. For example, when a patient is asleep, low piezo stack pulses will not be used to charge battery 242. Raw piezo stack pulses (voltage 704) as shown in a graph 700 of FIG. 17 over time 706 are rectified by a voltage rectifier 708 to produce a rectified and smoothed voltage output (voltage 704) shown in a graph 702 of FIG. 17B. The rectified and smoothed voltage output from the piezo stacks is used to charge battery 242. Thus, power harvesting from motion of knee joint implant 200 is achieved by using the pulses generated by the piezo stacks.

Figure 18:
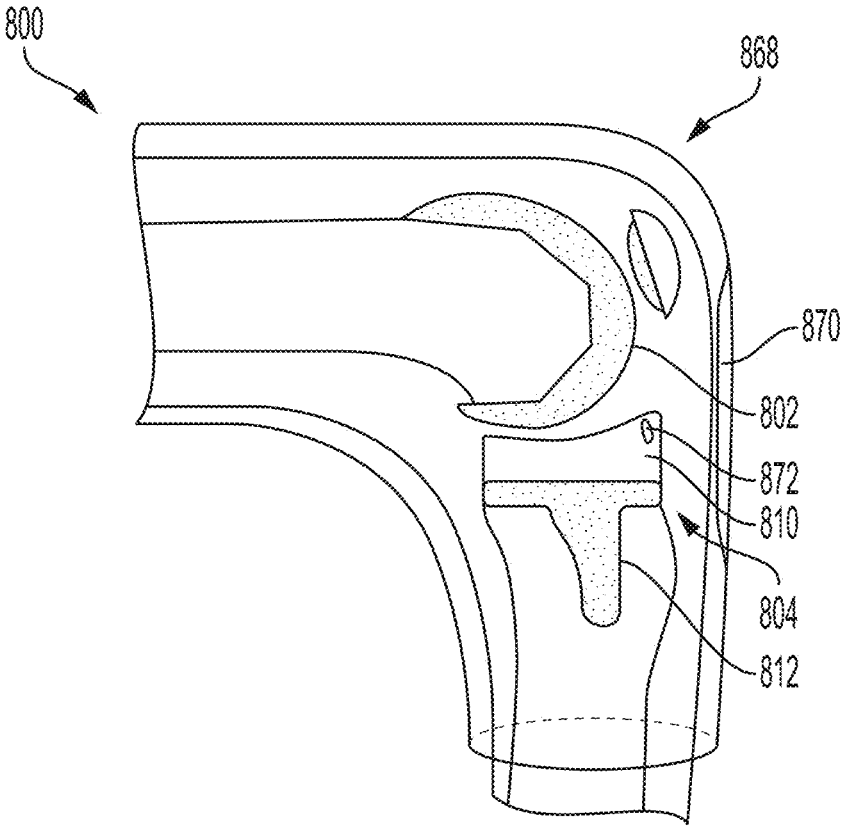
FIG. 18 is a schematic view of a knee joint implant with a charging sleeve according to an embodiment of the present disclosure.

FIG. 18 is a schematic view of a knee joint implant 800 according to another embodiment of the present disclosure. Knee joint implant 800 is similar to knee joint implant 200, and therefore like elements are referred to with similar numerals within the 800-series of numbers. For example, knee joint implant 800 includes a femoral implant 802, a tibial implant 804 with a tibial stem 812 and a tibial insert 810. However, knee joint implant 800 includes a chargeable implant coil 872 located in tibial insert 810 which can be charged by an external coil 870 contained in an external sleeve 868 as shown in FIG. 18.

Figure 19:
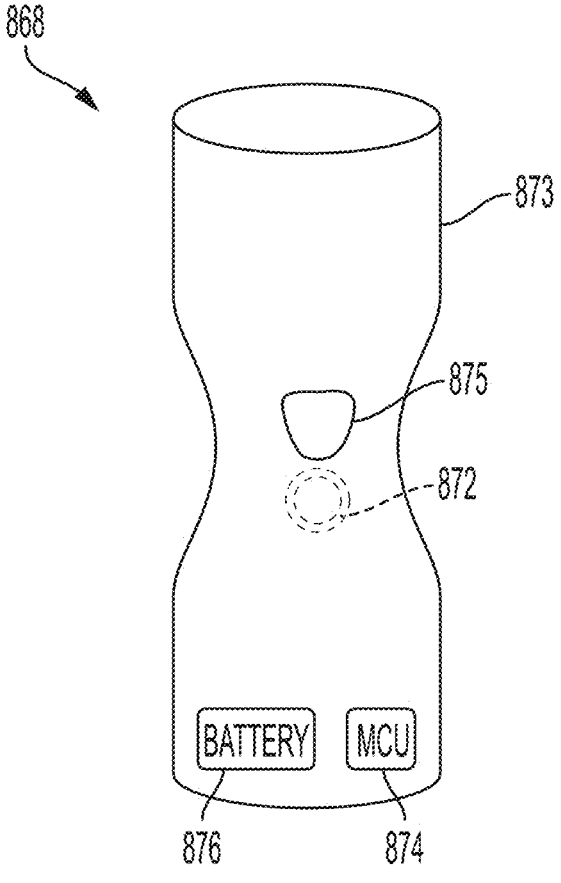
FIG. 19 is a front view of the charging sleeve of the knee joint implant of FIG. 17.

External sleeve 868 shown in FIG. 19 includes an outer body 873 made of stretchable fabric or other material. Outer body 873 is configured to be a ready-to-wear pull-on knee sleeve which a patiently can conveniently put on and remove. A kneecap indicator 875 allows the patient to conveniently align sleeve 868 with knee joint implant 800 for proper placement of external coil 870 with reference to implant coil 872 for charging. As shown in FIG. 18, when a patient aligns external sleeve 868 using kneecap indicator 875 and assumes a flexion position, external coil 870 is adjacent to implant coil 872 for proper charging. External sleeve 868 includes a battery 876 and a microcontroller 874 as shown in FIG. 19. Battery 876, which can be conveniently replaced, provides power to external coil 870. In another embodiment, external coil 870 may be charged by an external source not located on sleeve 868.

Figure 21:
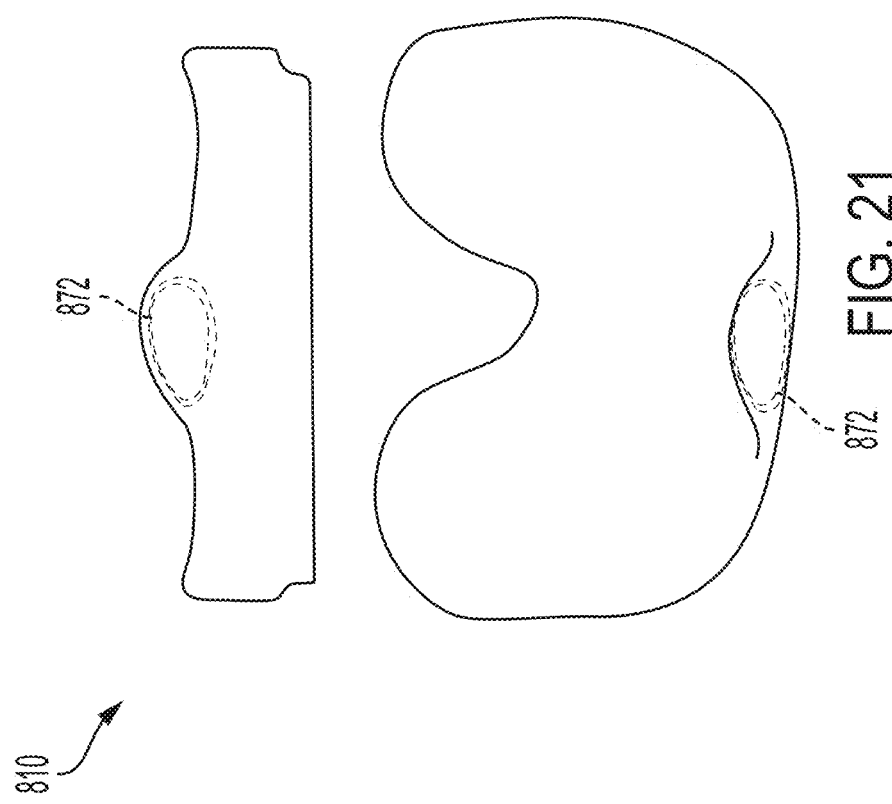
FIG. 21 shows top and front views of the insert of FIG. 19.
Figure 20:
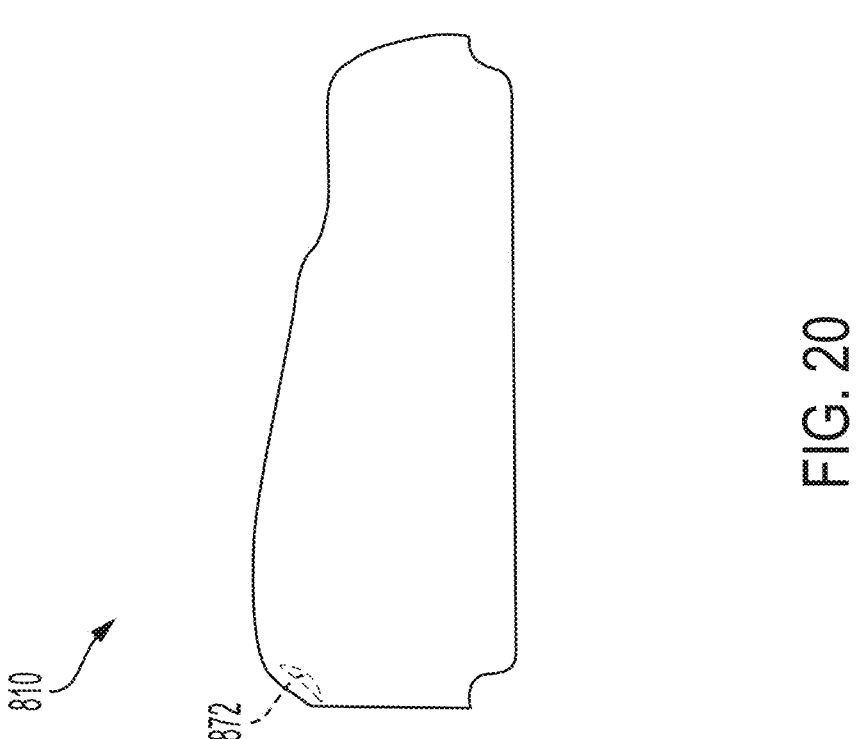
FIG. 20 is a side view of an insert of the knee joint implant of FIG. 17.

FIG. 20 shows a side view of tibial insert 810 of knee joint implant 800. Tibial insert 810 is made of a polymer or other suitable to facilitate charging of implant coil 872. Implant coil 872 is located within tibial insert 810 at an indent or depression at a proximal-anterior corner of the tibial insert as show in FIG. 20 and FIG. 21 (top and front views of tibial implant 810). The proximal-anterior location of implant coil 872 maximizes access to external coil 870 for efficient and convenient charging.

Figure 22B:
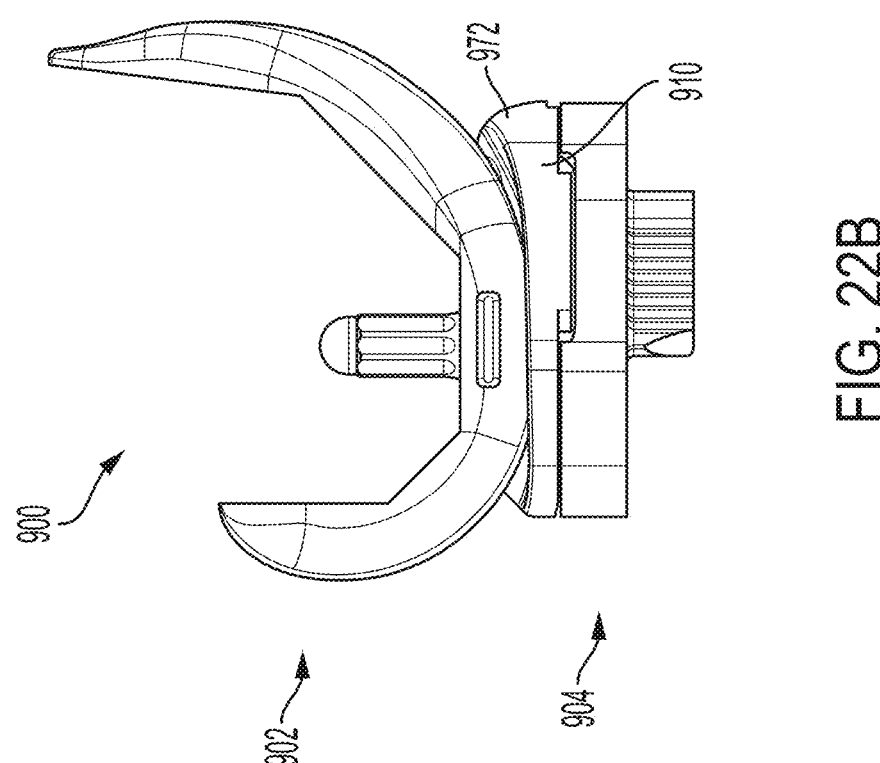
FIG. 22B is a side view of the knee joint implant of FIG. 22A.
Figure 22A:
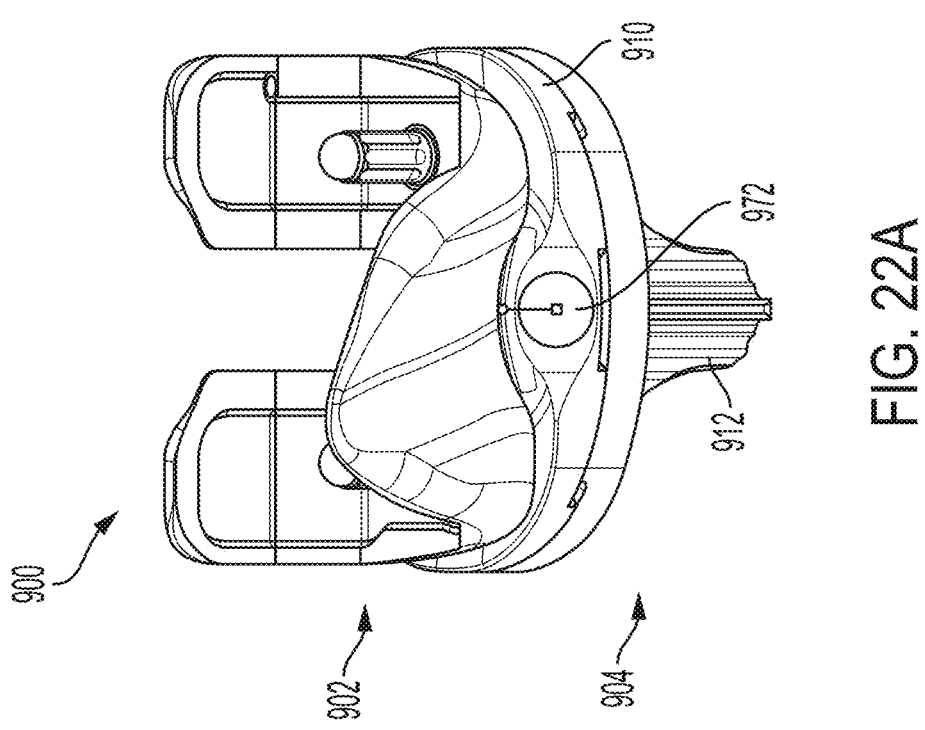
FIG. 22A is front view of a knee joint implant according to another embodiment of the present disclosure.

FIGS. 22A and 22B show a knee joint implant 900 according to another embodiment of the present disclosure. Knee joint implant 900 is similar to knee joint implant 800, and therefore like elements are referred to with similar numerals within the 900-series of numbers. For example, knee joint implant 900 includes a femoral implant 902, a tibial implant 904 with a tibial stem 912 and a tibial insert 910. However, knee joint implant 900 includes a chargeable implant coil 972 located at anterior end of tibial insert 910 which can be charged by an external coil 970 (not shown). An external sleeve as described with reference knee joint implant 900, or another charging mechanism can be used to conveniently charge implant coil 972.

Figure 23B:
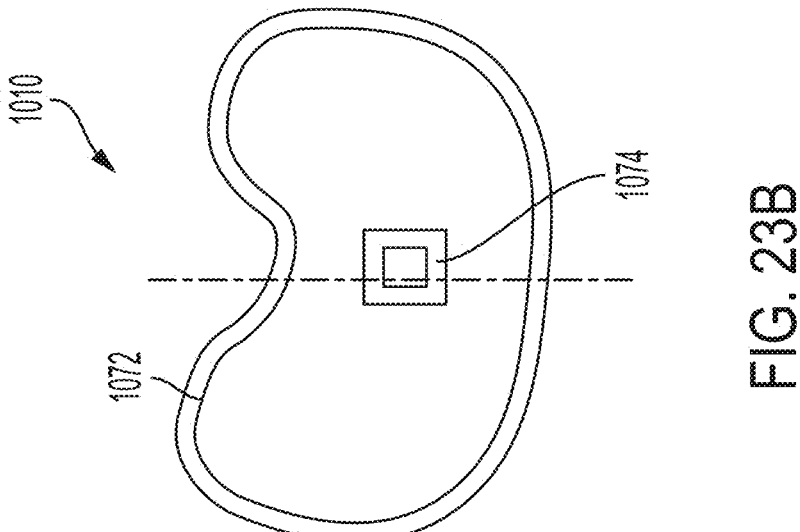
FIG. 23B is a top view of an insert of the tibial implant of FIG. 22A.
Figure 23A:
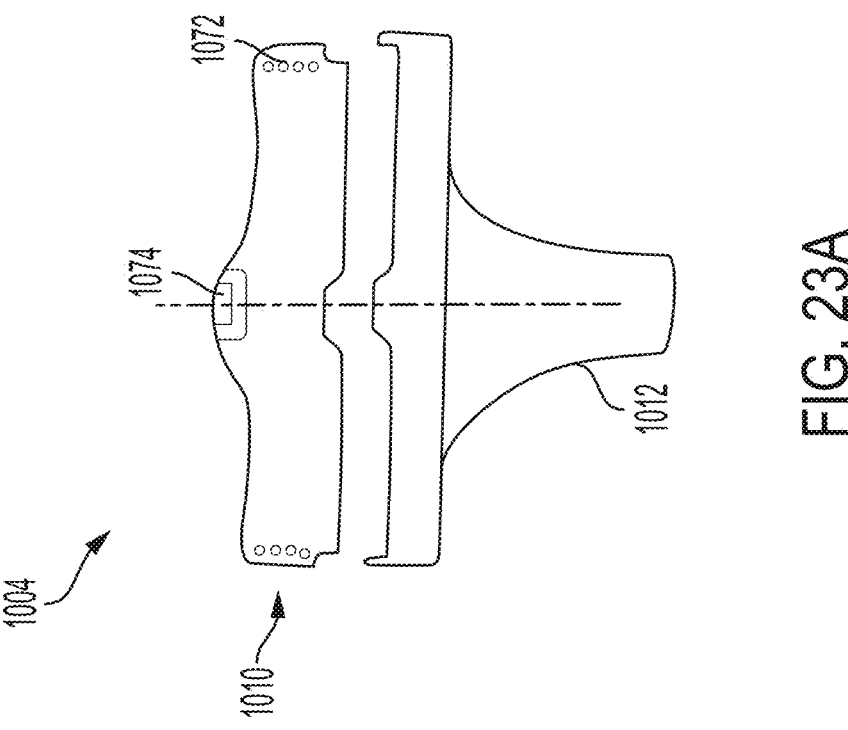
FIG. 23A is a front view of a tibial implant according to another embodiment of the present disclosure.

FIG. 23A is a front view of a tibial implant 1004 according to an embodiment of the present disclosure. Tibial implant 1004 is similar to tibial implant 204, and therefore like elements are referred to with similar numerals within the 1000-series of numbers. For example, tibial implant 1004 includes a tibial stem 1012 and a tibial insert 1010. However, tibial insert 1010 includes a charging coil 1072 located around a periphery of the tibial insert 1010 as shown in FIG. 23B. A spectroscopy sensor 1074 in tibial insert 1010 serves as an infection detection sensor for tibial implant 1004. Spectroscopy sensor 1074 is configured to identify the onset of biofilm on tibial implant (or a corresponding femoral implant) to provide early detection of implant related infection.

Figure 24B:
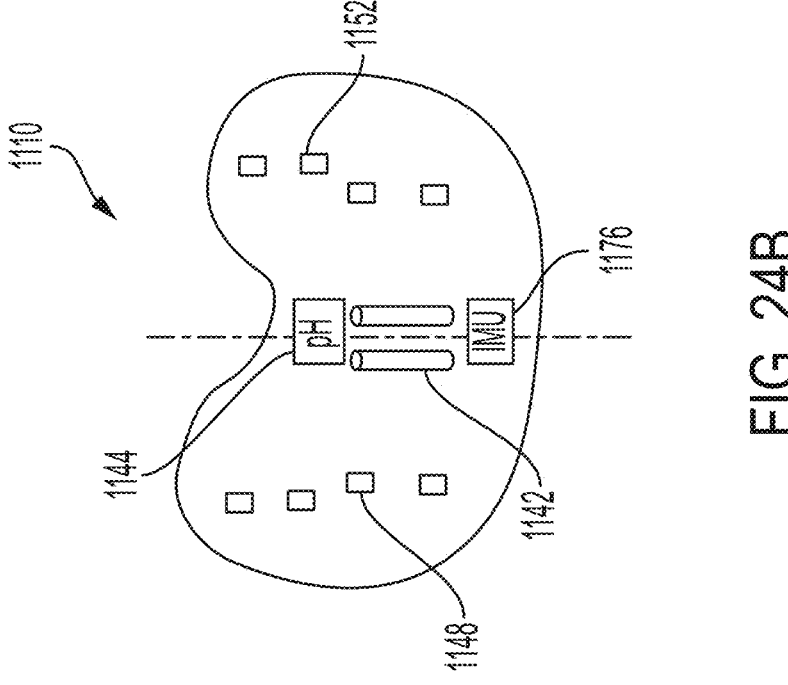
FIG. 24B is a top view of an insert of the tibial implant of FIG. 24A.
Figure 24A:
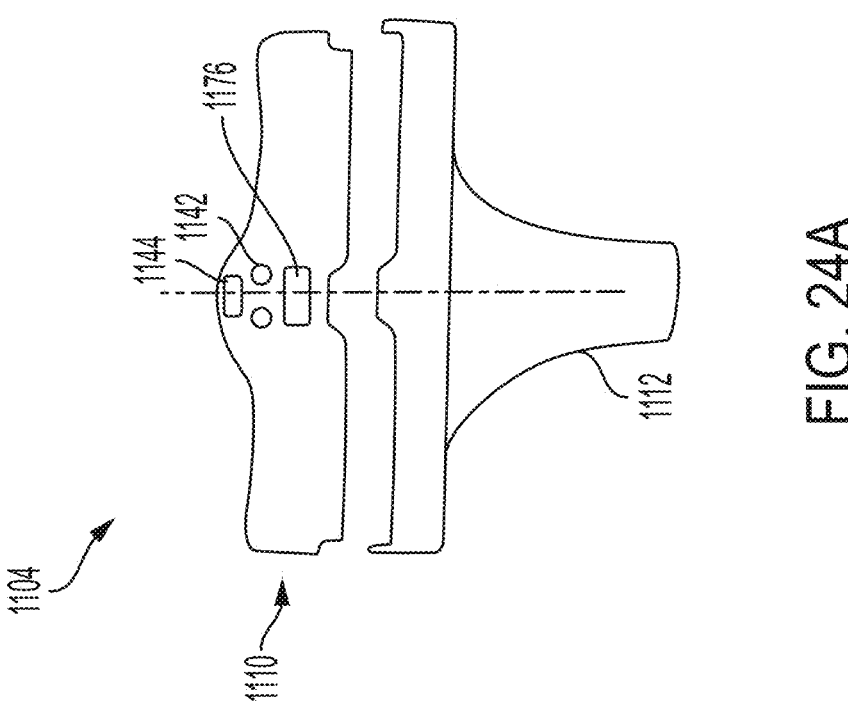
FIG. 24A is a front view of a tibial implant according to another embodiment of the present disclosure.

FIG. 24A is a front view of a tibial implant 1104 according to an embodiment of the present disclosure. Tibial implant 1104 is similar to tibial implant 204, and therefore like elements are referred to with similar numerals within the 1100-series of numbers. For example, tibial implant 1104 includes a tibial stem 1112 and a tibial insert 1110. However, tibial insert 1110 includes an IMU 1176 and five Hall sensor assemblies for each of the medial and lateral marker readers. The arrangement of the Hall sensor assemblies differ from tibial insert 210. Sensor data from IMU 1176 provides additional knee implant joint movement data as more fully explained above. For example, IMU 1176 can detect or confirm knee joint position during continuous loading positions of a patient such as standing. IMU data can reveal, or support measurements related to gait characteristics, stride, speed, etc., of a patient. pH sensor 1144 of tibial insert 1110 is located adjacent to a proximal face of the tibial insert at a central location as shown in FIG. 24B. All sensors of tibial implant 1104 are powered by batteries located in tibial insert 1110.

Figure 25B:
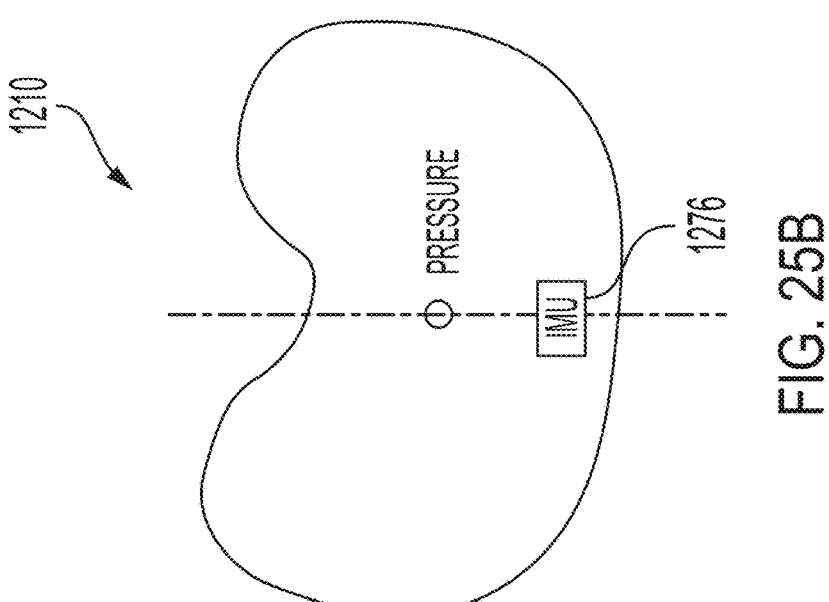
FIG. 25B is a top view of an insert of the tibial implant of FIG. 25A.
Figure 25A:
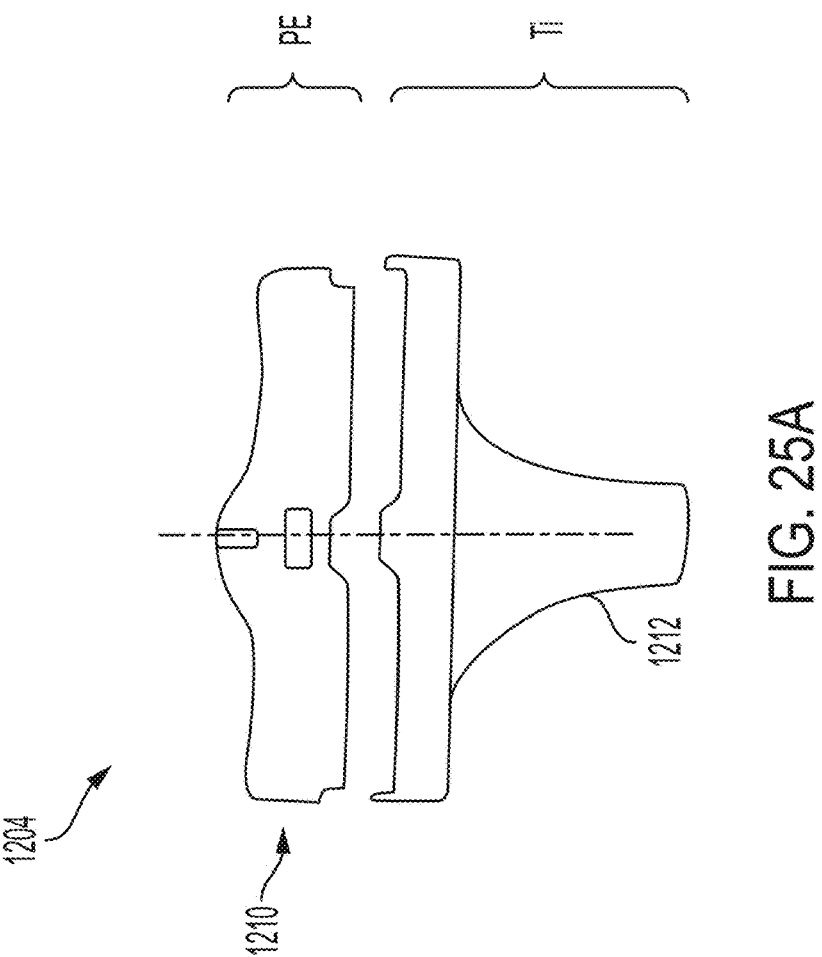
FIG. 25A is a front view of a tibial implant according to another embodiment of the present disclosure.

A tibial implant 1204 according to another embodiment of the present disclosure is shown in FIGS. 25A and 25B. Tibial implant 1204 is similar to tibial implant 204, and therefore like elements are referred to with similar numerals within the 1200-series of numbers. For example, tibial implant 1204 includes a tibial stem 1212 and a tibial insert 1210. However, tibial insert 1210 includes an IMU 1276 and a pressure sensor. Tibial insert 1210 is made of polyethylene and tibial stem 1212 is made of titanium in this embodiment.

Figure 26:
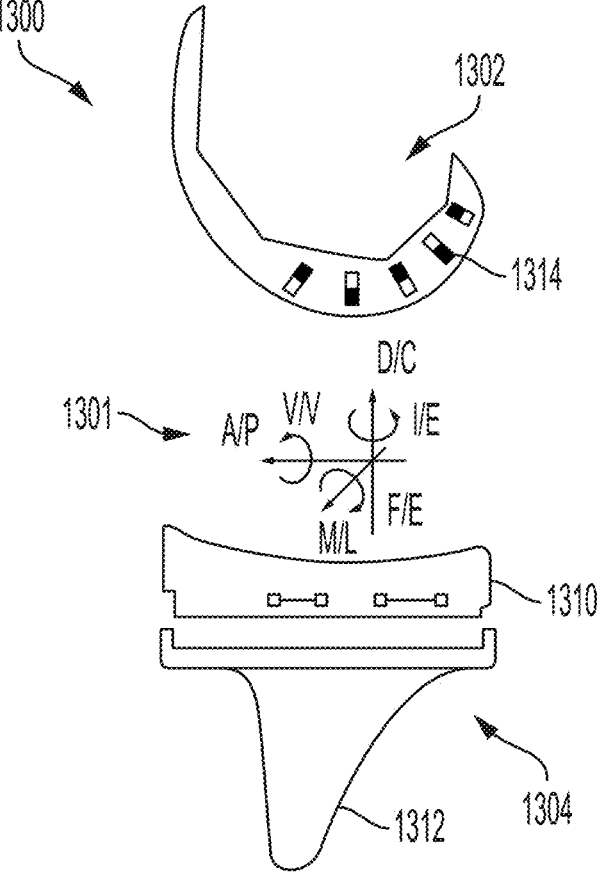
FIG. 26 is a side view of a knee joint implant according to another embodiment of the present disclosure.

FIG. 26 is a side view of a knee joint implant 1300 according to another embodiment of the present disclosure.

Figure 27:
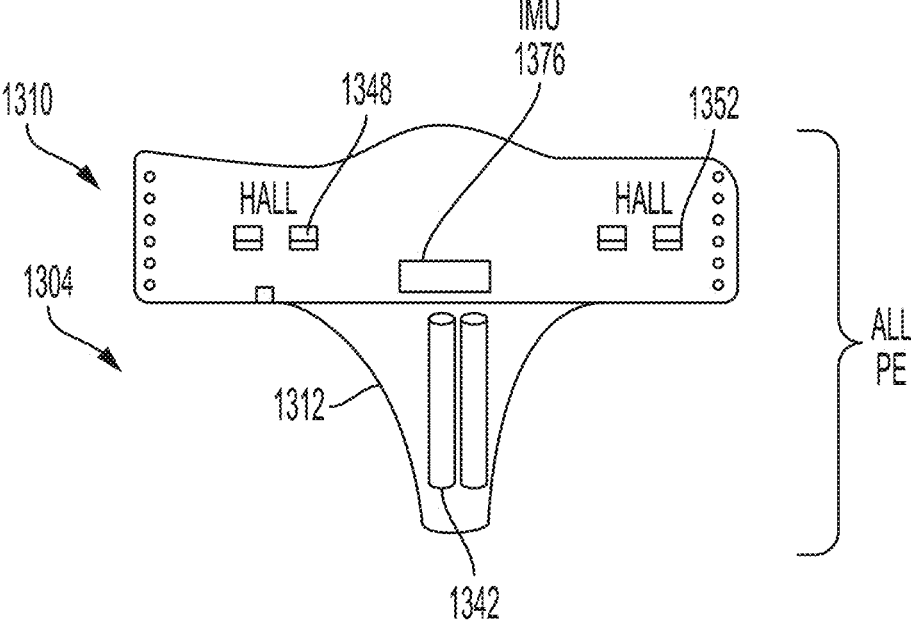
FIG. 27 is a front view of a tibial implant of the knee joint implant of FIG. 26.

Knee joint implant 1300 is similar to knee joint implant 200, and therefore like elements are referred to with similar numerals within the 1300-series of numbers. For example, knee joint implant 1300 includes a femoral implant 1302, a tibial implant 1304 with a tibial stem 1312 and a tibial insert 1310. However, battery 1342 of knee joint implant 1300 are located in tibial stem 1312 as best shown in FIG. 27. Locating batteries 1342 in tibial stem provides room for additional sensors in tibial insert 1310. The tibial stem and tibial insert 1310 can be made of polyethylene in this embodiment. Various knee joint implant motion data 1301 collected by magnetic markers and marker readers is shown in FIG. 26. Motion data 1301 can include internal-external rotation, medial-lateral rotation, varus-valgus rotation, etc.

Figure 28:
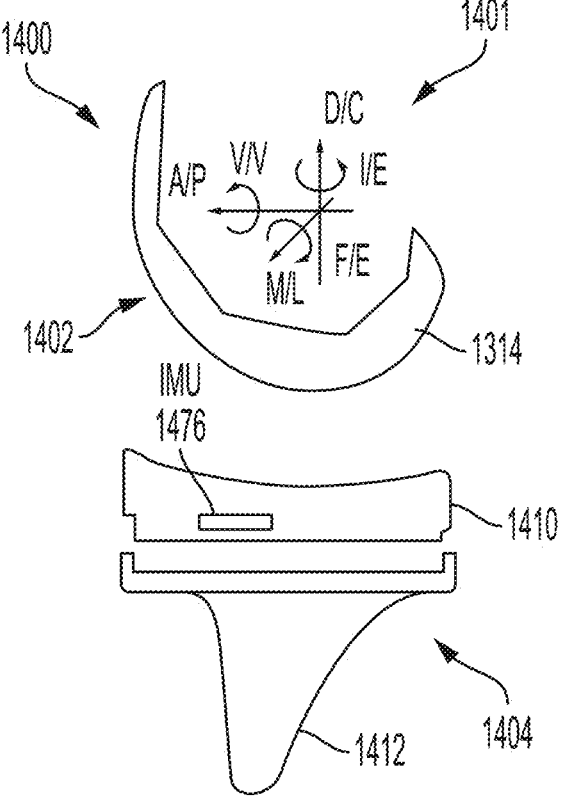
FIG. 28 is a schematic side view of a knee joint implant illustrating various measurements according to another embodiment of the present disclosure.

A knee joint implant 1400 according to another embodiment of the present disclosure is shown in FIG. 28. Knee joint implant 1400 is similar to knee joint implant 200, and therefore like elements are referred to with similar numerals within the 1400-series of numbers. For example, knee joint implant 1400 includes a femoral implant 1402, a tibial implant 1404 with a tibial stem 1412 and a tibial insert 1410. However, tibial insert 1410 includes an IMU 1476. Sensor data from IMU 1476 provides additional knee implant joint motion data 1401. Motion data 1401 can include internal-external rotation, medial-lateral rotation, varus-valgus rotation, etc. for reviewing knee joint implant 1400 performance. For example, internal-external rotation measurements exceeding a predetermined threshold can indicate knee joint implant lift-off (instability), medial-lateral rotation measurements exceeding predetermined thresholds can indicate knee joint implant stiffness. Combining these measurements with inputs from the various other sensors of tibial insert 1410 will provide a detailed assessment of knee joint implant 400 performance.

Figure 29:
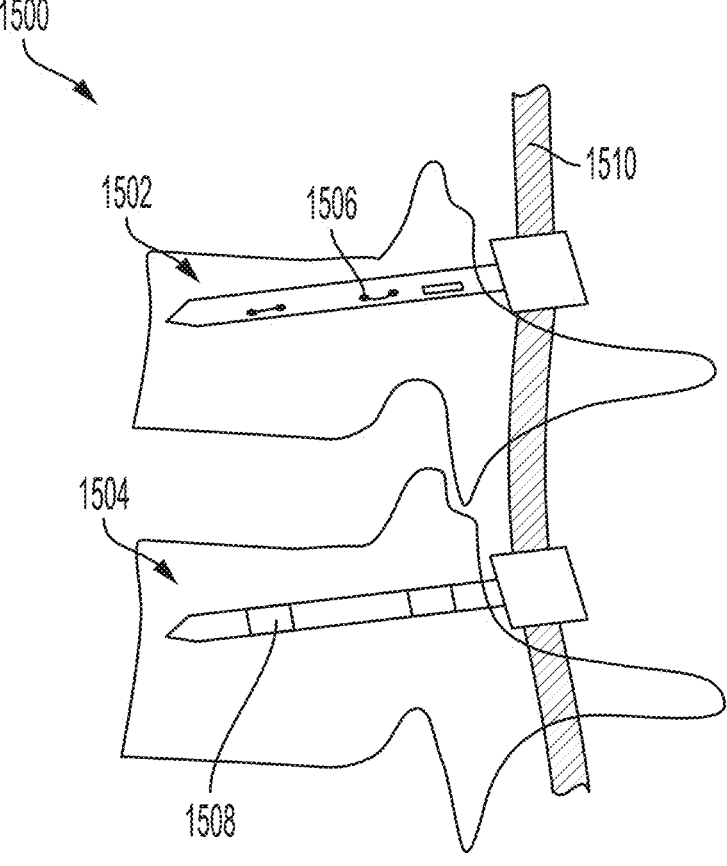
FIG. 29 is a schematic side view of a spinal implant assembly according to another embodiment of the present disclosure.

Referring now to FIG. 29, a spinal implant assembly 1500 is shown according to an embodiment of the present disclosure. Spinal implant assembly 1500 includes a spinal implant 1510 such as a plate, rod, etc., secured to first and second vertebrae by a first fastener 1502 and a second fastener 1504, respectively. The first and second fasteners can be screws as shown in FIG. 29. First fastener 1502 includes magnetic flux density detectors such as Hall sensor assemblies 1506 located along a body of the fastener 1502. Second fastener 1504 includes magnetic markers 1508 located along a body of the fastener. Any movement of second fastener 1504 with respect to the first fastener is detected and measured by Hall sensor assemblies 1506. Thus, the first and second fasteners function as an absolute or incremental encoder to detect spinal mobility of a patient during daily activity. As described with reference to the knee joint implants disclosed above, various other sensors such as temperature, pressure, pH, load, etc., can be included in fast fastener 1502 to provide additional measurements related to spinal implant assembly 1500 performance during a patient's recovery and rehabilitation. Ideally, there should be little to no movement between the first and second vertebrae for successful for spinal fusion. Therefore, any movement detected between the first and second fastener may indicate a compromised spinal implant assembly.

Figure 30:
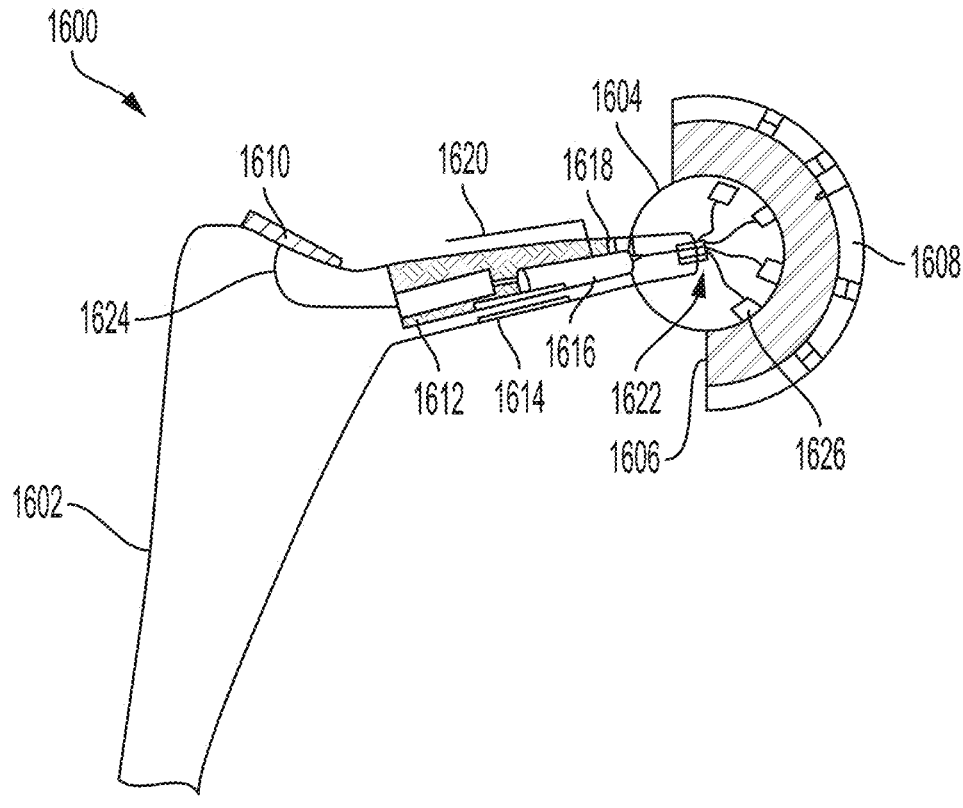
FIG. 30 is side view of a hip implant according to another embodiment of the present disclosure.
Figure 31C:
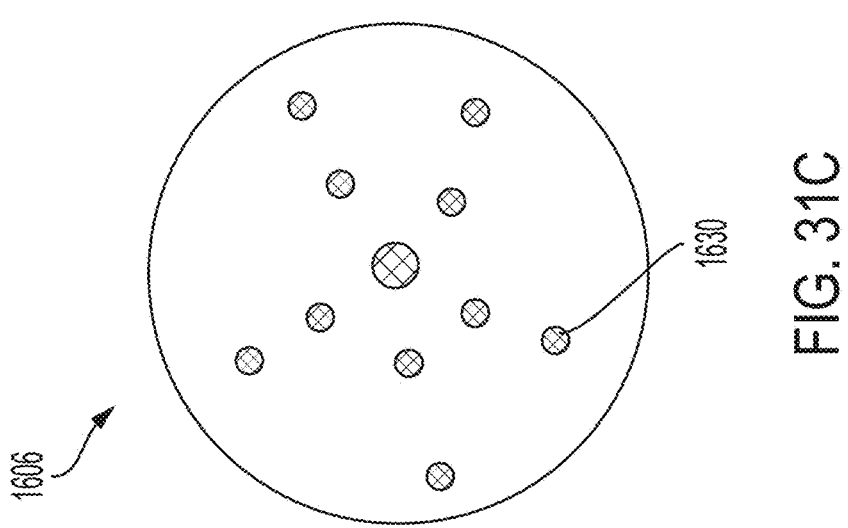
FIG. 31C is a top view of the sensor assembly and the insert of FIG. 31B.
Figure 31B:
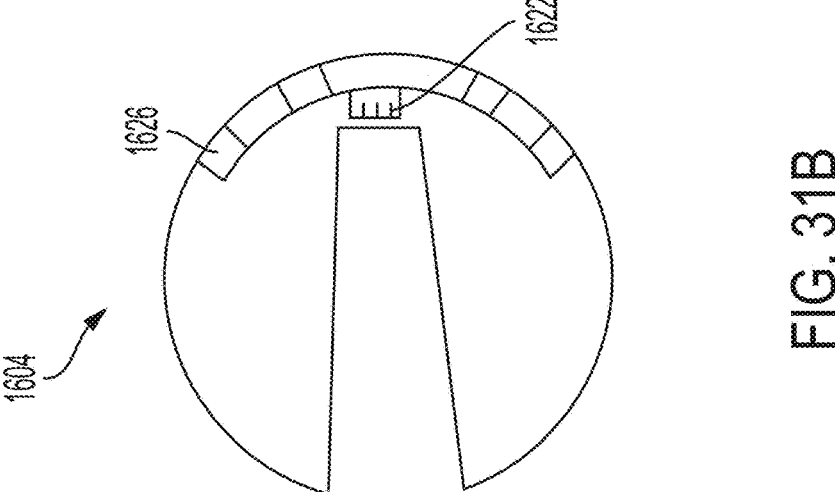
FIG. 31B is a side view of the sensor assembly and an insert of the hip implant of FIG. 31A.
Figure 31A:
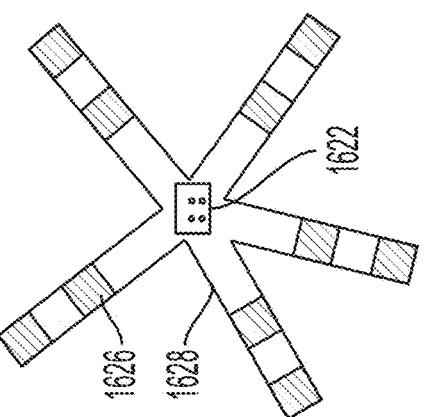
FIG. 31A is a schematic view of a sensor assembly of the hip implant of FIG. 30.

FIG. 30 is side view of a hip implant 1600 according to an embodiment of the present disclosure. Hip implant 1600 includes a stem 1602, a femoral head 1604, an insert 1606 and an acetabular component 1608. Magnetic flux density sensors such as Hall sensor assemblies 1626 are located on a flex connect 1628 and placed around femoral head 1604 as shown in FIGS. 31A and 31B. A connector 1622 on flex connect 1628 allows for convenient connection of femoral head 1604 with stem 1602. Magnetic markers 1630 are located on insert 1606 as best shown in FIG. 31C. Any motion of insert 1606 is detected by Hall sensor assemblies 1626 by measuring the change in magnetic flux density. Thus, Hall sensor assemblies 1626 and markers 1630 function as an absolute or incremental encoder to detect hip movement of a patient during daily activity.

Hip implant 1600 includes a charging coil 1610 located on stem 1602 as shown in FIG. 30. Charging coil 1610 charges a battery 1612 via a connector 1624 to power the various sensors located in hip implant 1600. A load sensor 1614 such a strain gauge detects forces between stem 1602 and acetabular component 1608 to monitor and transmit hip loads during patient rehabilitation and recovery. Various electronic components 1616, including sensors described with reference to knee joint implants, are located in stem 1602. A pH sensor 1618 located on stem can measure alkalinity and provide early detection notice of implant related infection. Data from these sensors is transmitted to an external source via an antenna 1620 as described with reference to the knee joint implants disclosed above.

Figure 32:
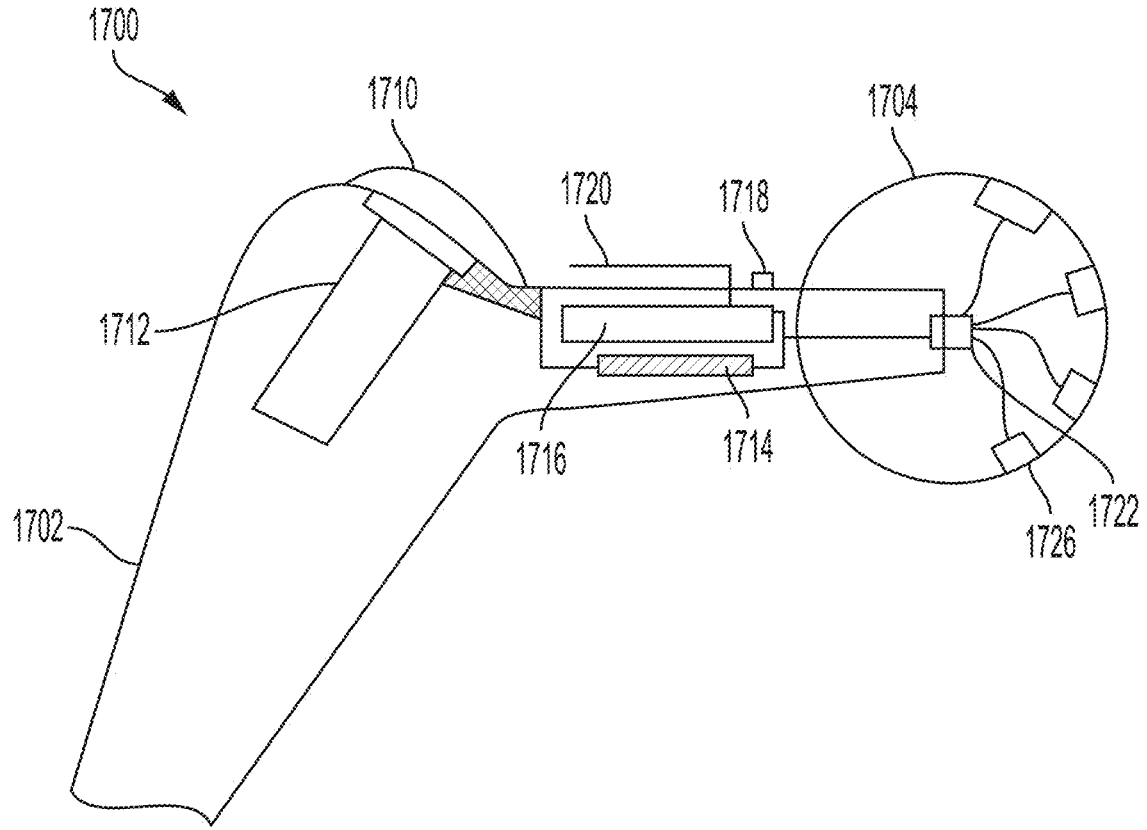
FIG. 32 is a side view of a hip implant according to another embodiment of the present disclosure.
Figure 33:
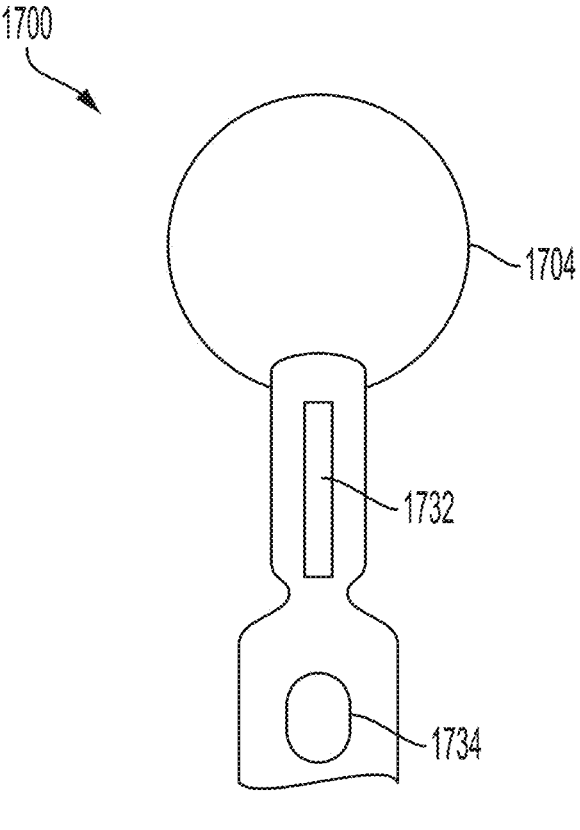
FIG. 33 is a partial top view of the hip implant of FIG. 32.

FIG. 32 is a side view of a hip implant 1700 according to another embodiment of the present disclosure. Hip implant 1700 is similar to hip implant 1600, and therefore like elements are referred to with similar numerals within the 1700-series of numbers. For example, hip implant 1700 includes a stem 1702, a femoral head 1704 and an acetabular component (not shown). However, battery 1712 of hip implant 1700 is located away from electric components 1716 as best shown in FIG. 32. Battery 1712 can be conveniently inserted into hip implant 1700 via a slot 1734 as shown in FIG. 33. Similarly, electric components 1716 can be inserted into hip implant 1700 via a slot 1732. This allows for convenient replacements and upgrades to the battery and electric components without disturbing hip implant 1700.

Figure 34:
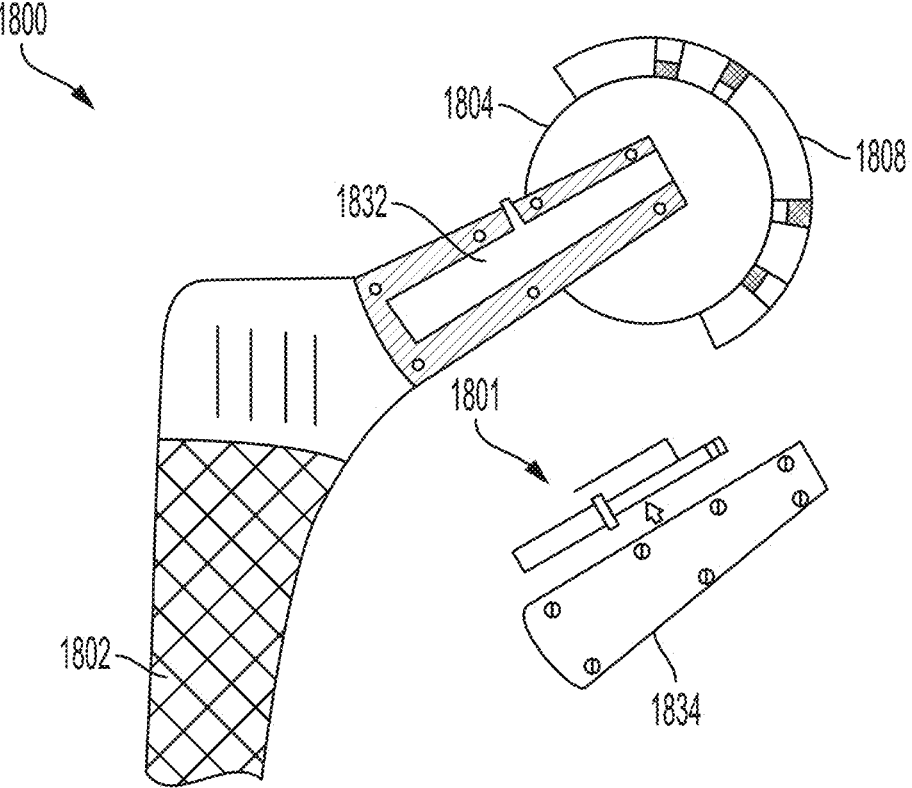
FIG. 34 is a side view of a hip implant according to another embodiment of the present disclosure.

FIG. 34 is a side view of a hip implant 1800 according to another embodiment of the present disclosure. Hip implant 1800 is similar to hip implant 1600, and therefore like elements are referred to with similar numerals within the 1800-series of numbers. For example, hip implant 1800 includes a stem 1802, a femoral head 1804 and an acetabular component (not shown). However, slot 1832 of hip implant 1800 is configured to receive all electronic components structured as a modular electronic assembly 1801 or a sensor assembly. A slot cover 1834 ensures that electronic assembly 1801 is secured and sealed in slot 1832. Thus, hip implant 1800 can be easily provided with replacement or upgrades to the electric components without disturbing hip implant 1800.

Figure 35:
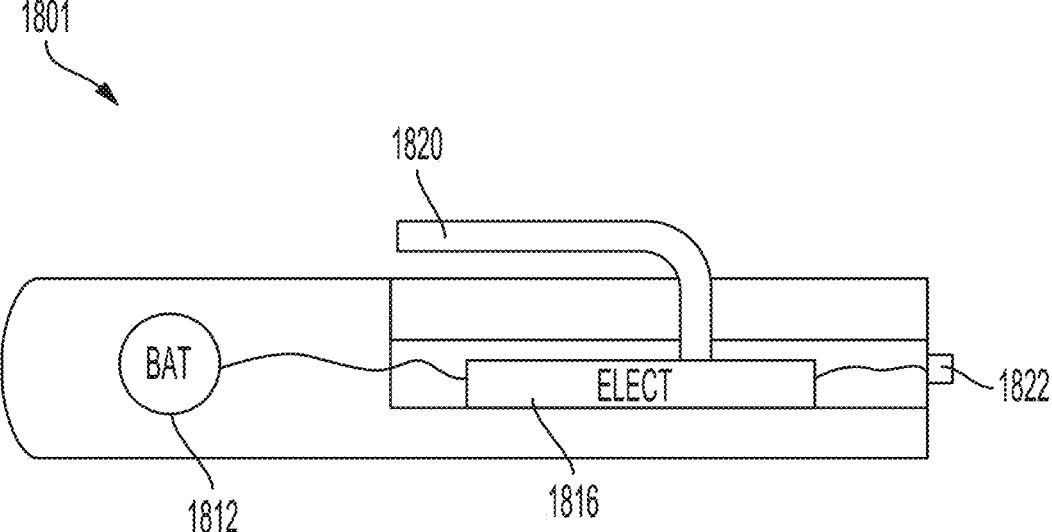
FIG. 35 is a side view of an electronic assembly of the hip implant of FIG. 34 according to another embodiment of the present disclosure.
Figure 36:
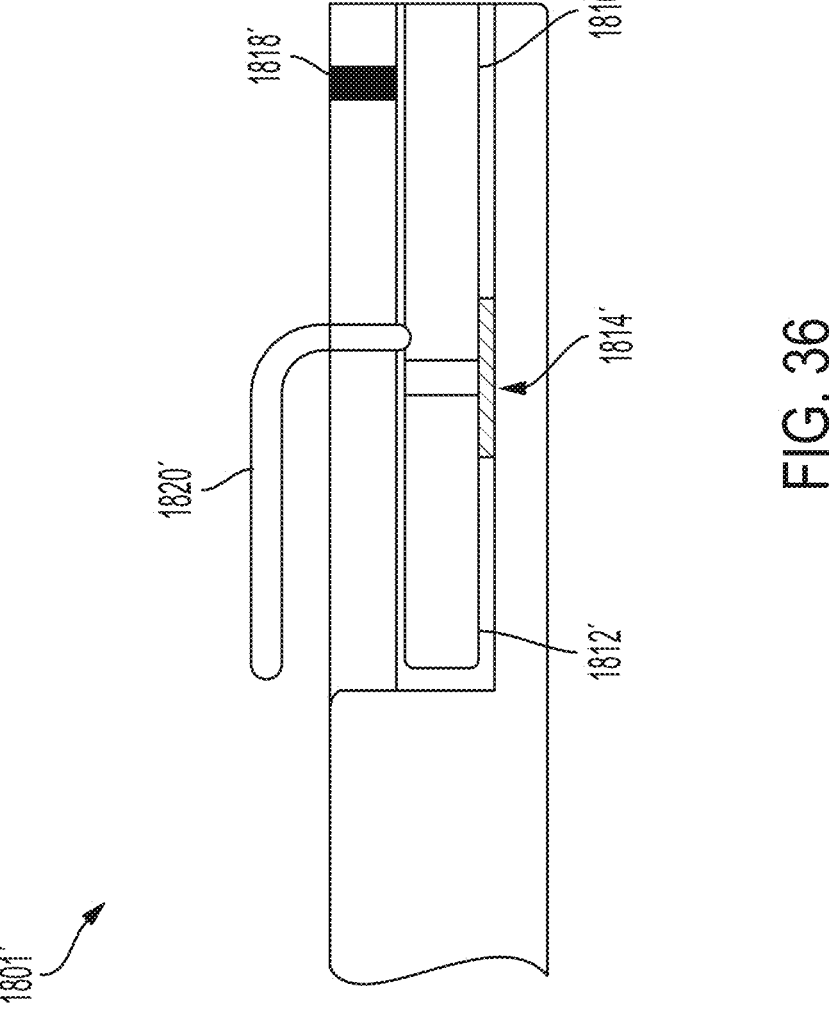
FIG. 36 is a side view of an electronic assembly of the hip implant of FIG. 34 according to another embodiment of the present disclosure.

A first embodiment of a modular electronic assembly 1801 is shown in FIG. 35. Electronic assembly includes a connector 1822 to connect to femoral head 1804, various electronic components 1816, a battery 1812 and an antenna 1820. Another embodiment of a modular electronic assembly 1801' is shown in FIG. 36. Electronic assembly 1801' includes various electronic components 1816', a battery 1812', a load sensor such as a strain gauge 1814' and an antenna 1820'. Electronic assembly 1801' includes a pH sensor 1818' to provide early detection of implant related infection.

Figure 37:
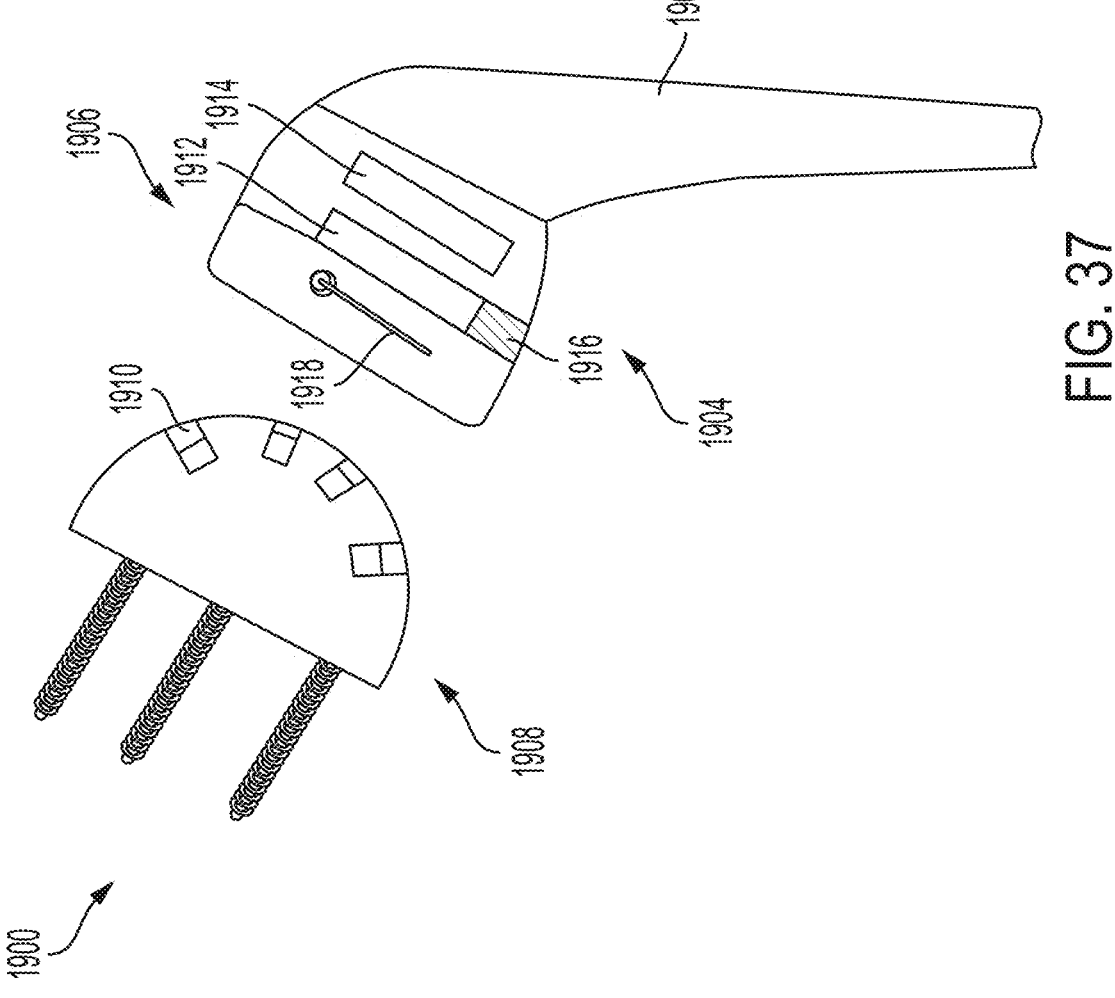
FIG. 37 is a side view of a shoulder implant according to another embodiment of the present disclosure.
Figure 39:
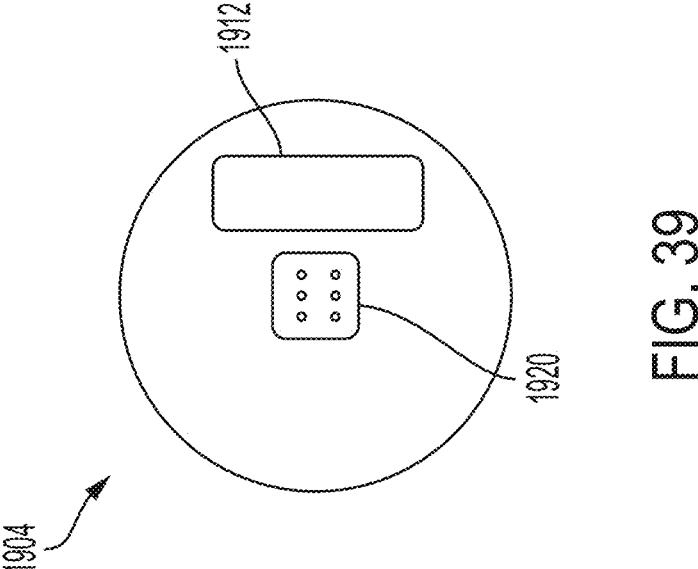
FIG. 39 is a top view of a cup of the shoulder implant of FIG. 37.
Figure 38:
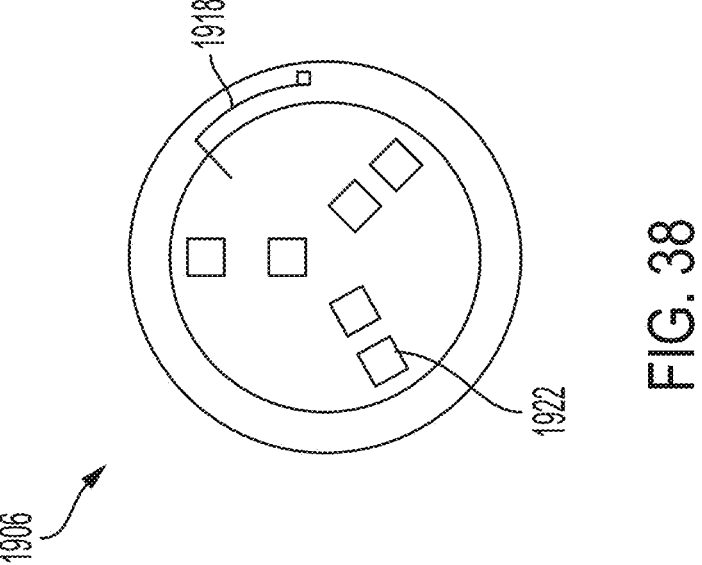
FIG. 38 is top view of an insert of the shoulder implant of FIG. 37.

FIG. 37 is a side view of a reverse shoulder implant 1900 according to an embodiment of the present disclosure. Shoulder implant 1900 includes a stem 1902, a cup 1904, an insert 1906 and a glenoid sphere 1908. Magnetic flux density sensors such as Hall sensor assemblies 1922 are located on insert 1906 as shown in FIG. 38. A connector 1920 on cup 1904 as shown in FIG. 39 allows for attachment of the cup to insert 1906. Magnetic markers 1910 are located on glenoid sphere 1908 as best shown in FIG. 37. Any motion of glenoid sphere 1908 is detected by Hall sensor assemblies 1922 by measuring the change in magnetic flux density. Thus, Hall sensor assemblies 1922 and markers 1910 function as an absolute or incremental encoder to detect shoulder movement of a patient during daily activity.

Shoulder implant 1900 includes a battery 1914 and an electronic assembly 1912 located within cup 1904. A pH sensor 1916 is located on cup 1904 to measure alkalinity and provide early detection notice of implant related infection. An antenna 1918 located on insert 1906 is provided to transmit sensor data to an external source to monitor and transmit shoulder implant 1900 performance during patient rehabilitation and recovery. Various electronic components of electronic assembly 1912, including sensors described with reference to knee joint implants, are located in cup 1904.

Figure 41:
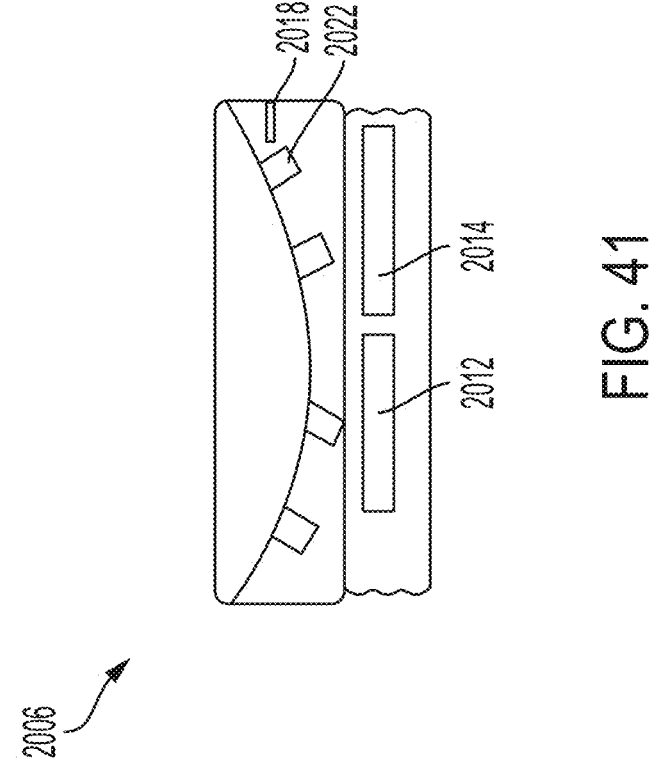
FIG. 41 is a side view of an insert of the shoulder implant of FIG. 40.
Figure 40:
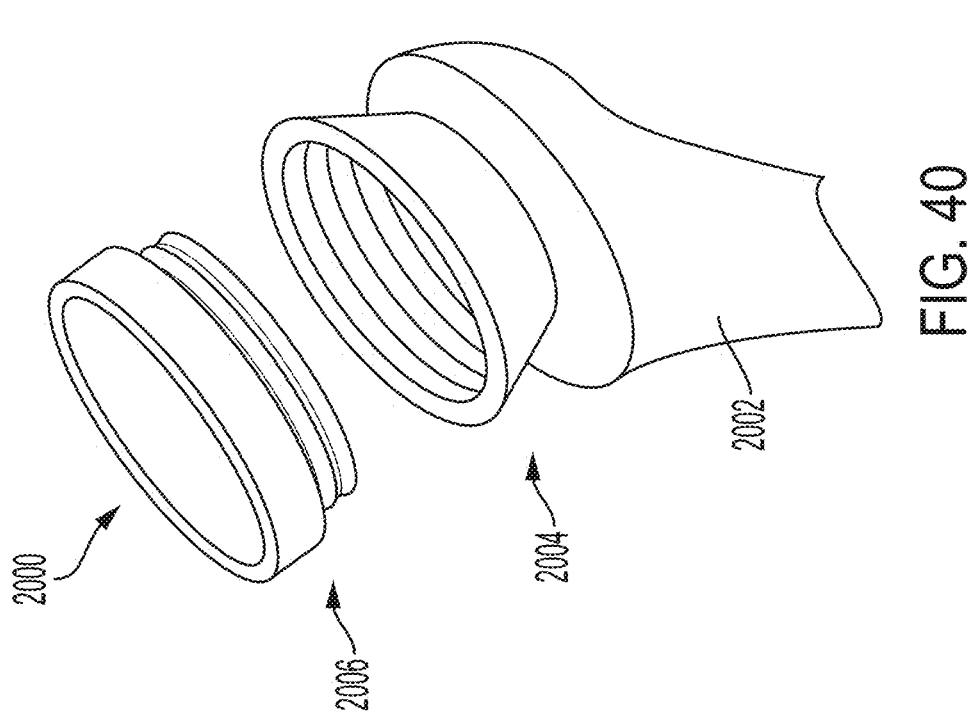
FIG. 40 is side view of a shoulder implant according to another embodiment of the present disclosure.

FIG. 40 is a side view of a reverse shoulder implant 2000 according to another embodiment of the present disclosure. Shoulder implant 2000 is similar to shoulder implant 1900, and therefore like elements are referred to with similar numerals within the 2000-series of numbers. For example, shoulder implant 2000 includes a stem 2002, a cup 2004 and an insert 2006. However, electronic assembly 2012, battery 2014 and pH sensor 2018 are located in insert 2006 as shown in FIG. 41. Thus, only a single component—i.e., the cup, of shoulder implant 2000 can be replaced or upgraded to make changes to sensor collection and transmission of the shoulder implant performance data.

Figure 42:
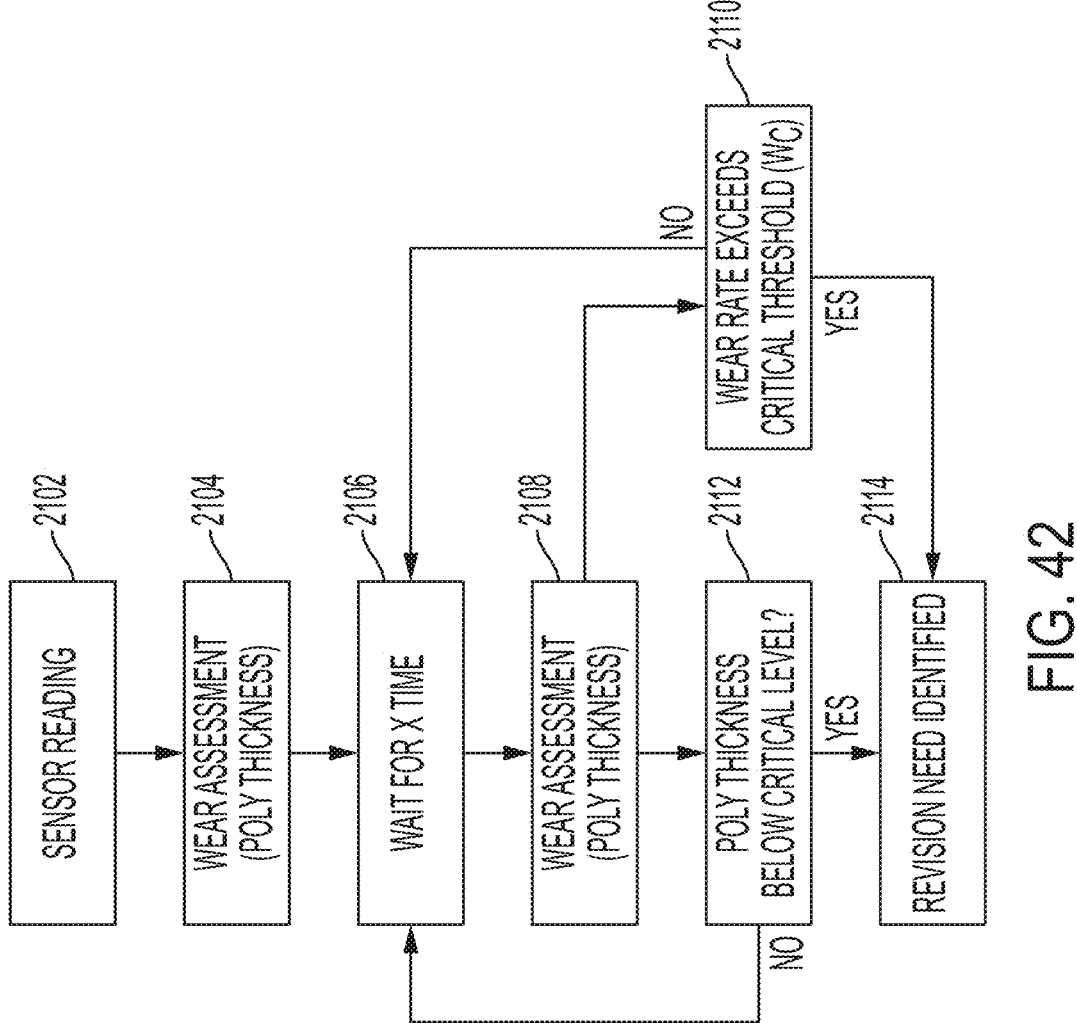
FIG. 42 is a flowchart showing steps to determine implant wear according to another embodiment of the present disclosure.
Figure 42:

FIG. 42 is a flowchart showing steps of a method 2100 to determine implant wear according to an embodiment of the present disclosure. While method 2100 is described with reference to a knee joint implant below, method 2100 can be applied to any implant with sensors described in the present disclosure, including all of the implants disclosed above. In a first step 2102, the initial thickness of the knee joint implant (such as thickness of the tibial insert) is recorded. This can be obtained by measuring the tibial insert prior to implantation, or measured based on the magnetic flux density generated by the magnetic markers as measured by the Hall sensor assemblies. Once the knee joint implant is implanted, periodic measurements of tibial insert thickness are determined in a step 2104 by evaluating the magnetic flux density. As the polyethylene housing of tibial insert degrades over time, the distance between the markers and Hall sensor assemblies are reduced as measured in a step 2106. This results in increased magnetic flux density values, which are used to estimate tibial insert wear in a step 2108.

Figures 43, 44:
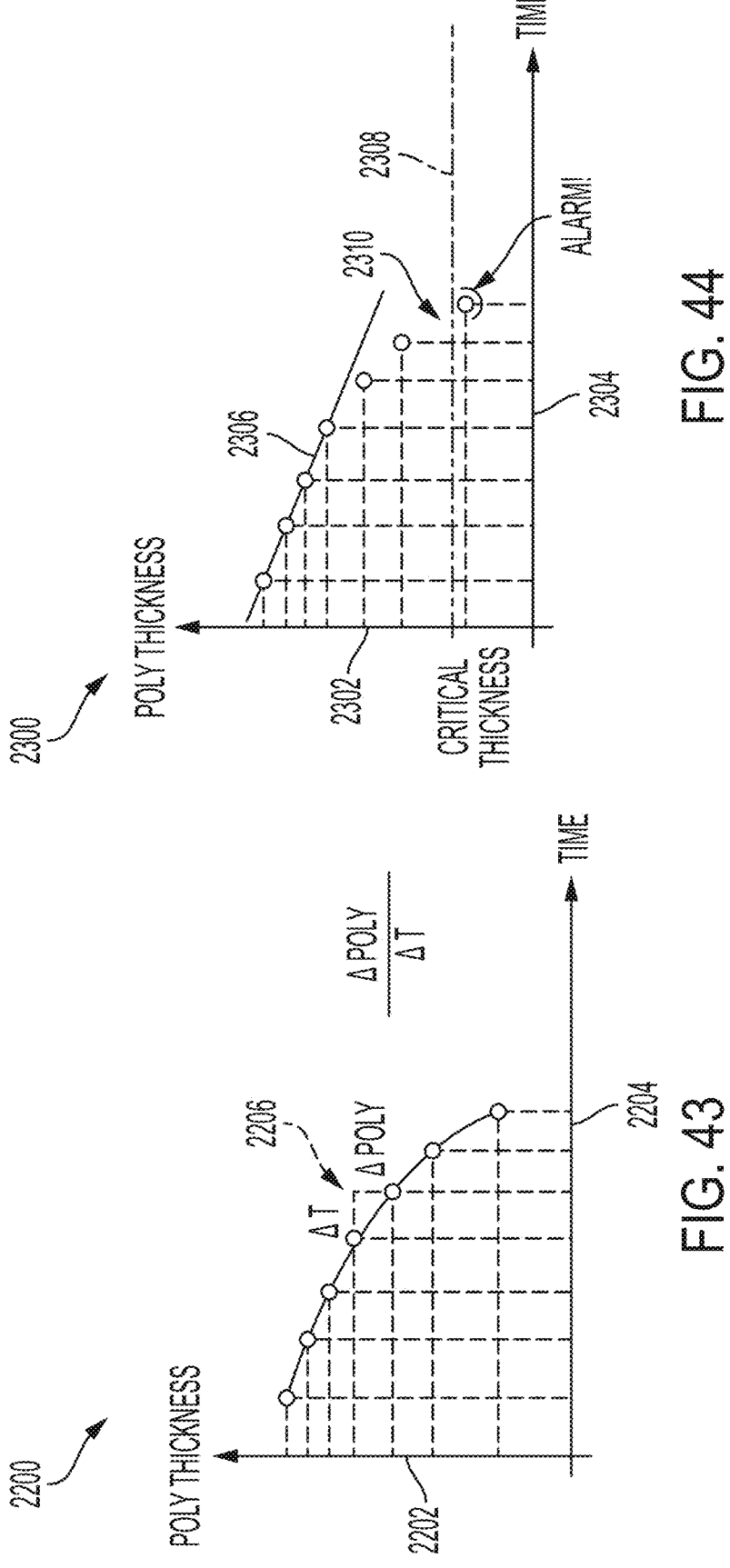
FIG. 43 is a first graph showing implant thickness over time.
FIG. 44 is a second graph showing implant thickness over time.

The decision to replace the tibial insert can be based on a rate of wear threshold 2206 as shown in graph 2200 of FIG. 43 in a step 2110, or a critical thickness value 2308 as shown in graph 2300 of FIG. 44 in a step 2112. Graph 2200 plots tibial insert thickness 2202 over time 2204. A change in slope 2206 denotes the rate of wear of tibial insert. When slope 2206 exceeds the predetermined rate of wear threshold, notification to replace the tibial insert is triggered in a step 2114. Graph 2300 plots tibial insert thickness 2302 over time 2304. When the tibial insert thickness is less than a predetermined critical thickness value 2308, a notification 2310 is triggered to replace the tibial insert in step 2114.

Figure 45:
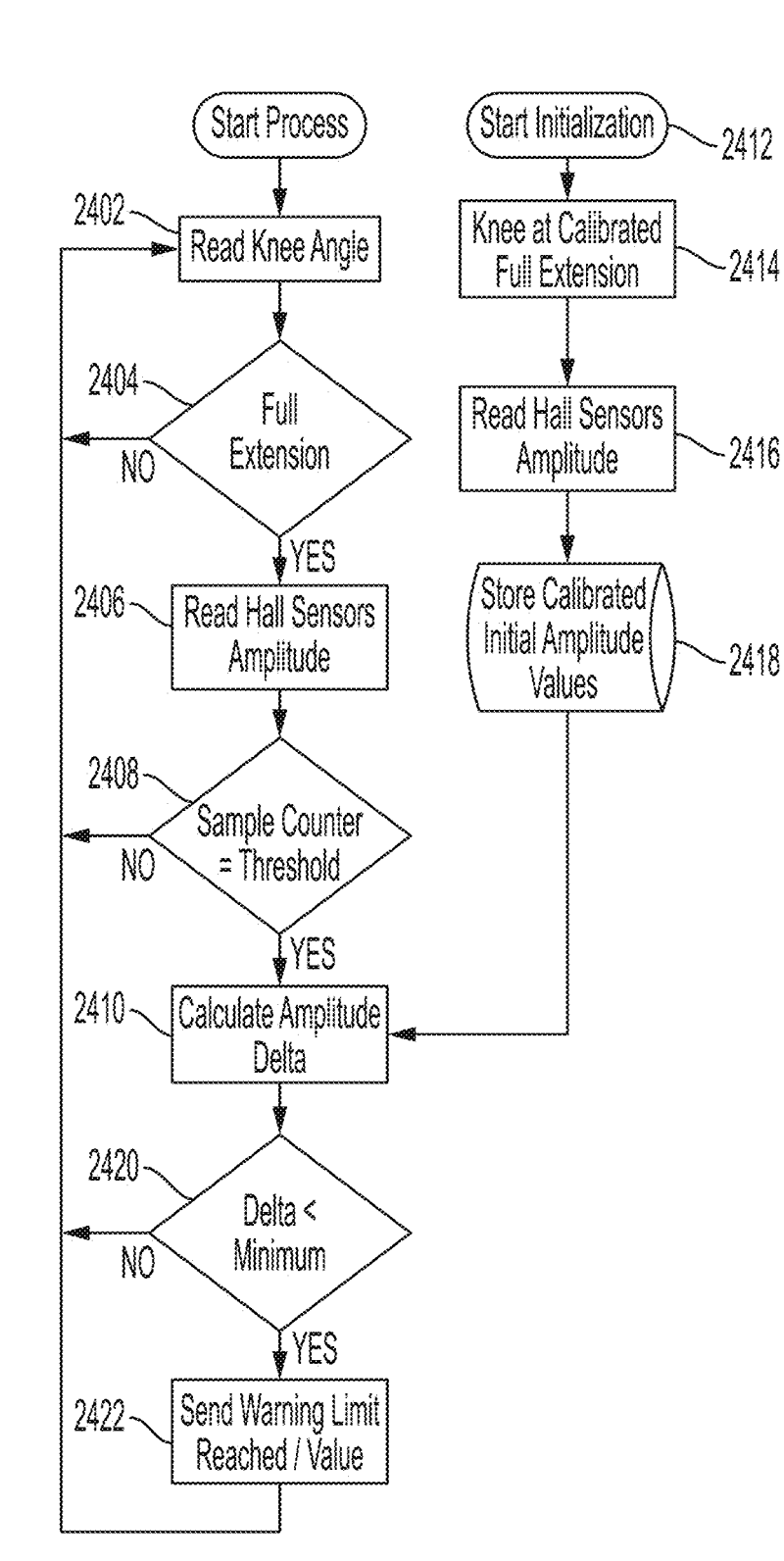
FIG. 45 is a flowchart showing steps to determine implant wear according to another embodiment of the present disclosure.

FIG. 45 is a flowchart showing steps of a method 2400 to determine implant wear according to another embodiment of the present disclosure. While method 2400 is described with reference to a knee joint implant below, method 2400 can be applied to any implant with sensors described in the present disclosure, including all of the implants disclosed above. In a first step 2402, a knee angle of a patient with the knee joint implant is measured. The knee is then placed in full extension in a step 2404. Hall sensor amplitudes are measured in a step 2408. This process is repeated over time to track the Hall sensor amplitude. These values are then compared with initial Hall sensor amplitude values obtained when the knee implant joint template was implanted (obtained by performing steps 2412 to 2418). As the Hall sensor amplitudes are directly related to a distance between the markers and the marker readers—i.e., a tibial insert thickness, a difference between the initial Hall sensor amplitudes and current Hall sensor amplitudes from step 2408 represent wear of the tibial insert in a step 2420. When a predetermined minimum implant thickness is reached in a step 2420, a notification to replace the tibial insert is triggered in a step 2422.

Figure 46:
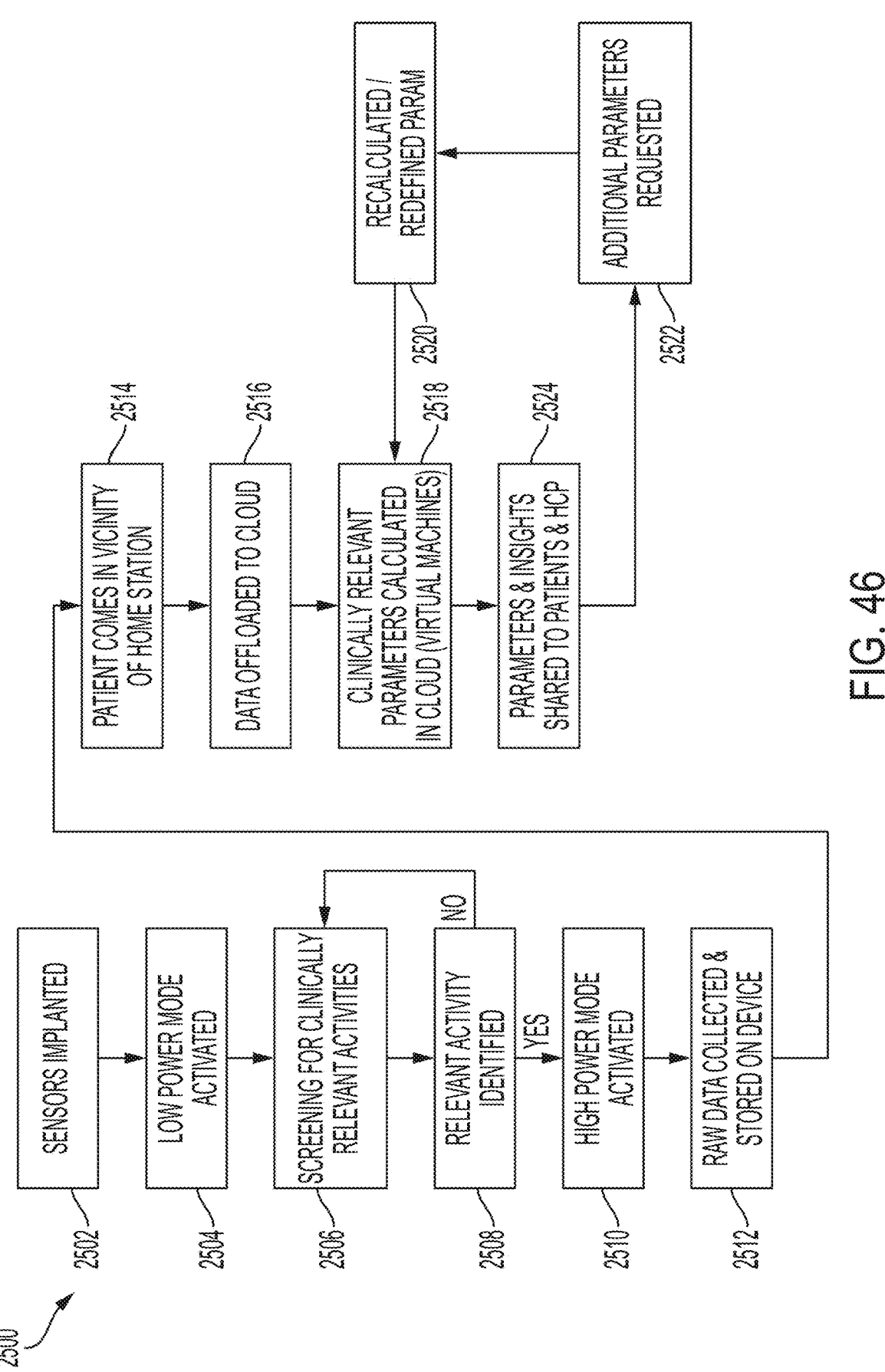
FIG. 46 is a flowchart showing for implant data collection according to another embodiment of the present disclosure.

FIG. 46 is a flowchart showing steps of a method 2500 for implant data collection according to an embodiment of the present disclosure. While method 2500 is described with reference to a knee joint implant below, method 2500 can be applied to any implant with sensors described in the present disclosure, including all of the implants disclosed above. In a first step 2502, a patient is implanted with a knee joint implant. The knee joint implant is in a low-power mode (to conserve battery power) until relevant activity is detected (steps 2504 and 2506). Once the relevant activity is identified by the sensor(s) of the knee joint implant (step 2508), the implant shifts to a high-power mode. Relevant activity to trigger the high-power mode can be patient-specific, and may include knee flexion speed, gait, exposure to sudden impact loads, temperature thresholds, alkalinity levels, etc. Upon identifying the relevant activity and switching over to the high-power mode, various sensors in the knee joint implant record and store sensor measurements on the device (step 2512). This data can be transferred from the patient to a home station when the patient is in the vicinity of the home station or a smart device (step 2514). The data is then transferred from the home station or the smart device to the cloud to be reviewed and analyzed by the software or virtual machines and/or by experts (steps 2518, 2520). Relevant information for patient rehabilitation and recovery uncovered from the sensor data is sent back to the patient (steps 2523, 2522) via a client portal. Thus, method 2500 preserves and extends battery life of the knee joint implant by shifting the implant from low-power to high-power mode when required, and shifting the implant back to the low-power mode to conserve energy during other periods.

In some examples, the relevant patient information may be that the knee joint and knee joint implant are in a healthy state, or alternatively that the knee joint is in an infected state. If the knee joint is determined to not be in a healthy state, the clinician can then take steps to review the condition more closely and prepare a plan for treatment if necessary. After review, the clinician can input the state of the joint as determined by the clinician so that the confirmed diagnosis is then associated with the data provided by the joint implant. The diagnosis data combined with corresponding sensor data is then stored in a cloud and henceforth considered in the software's future determinations of the state of a joint and joint implant. In some examples, the software is adapted to adjust and further refine its parameters and/or thresholds used in determining the state of an implant upon receipt of the diagnosis data.

Figure 47A:
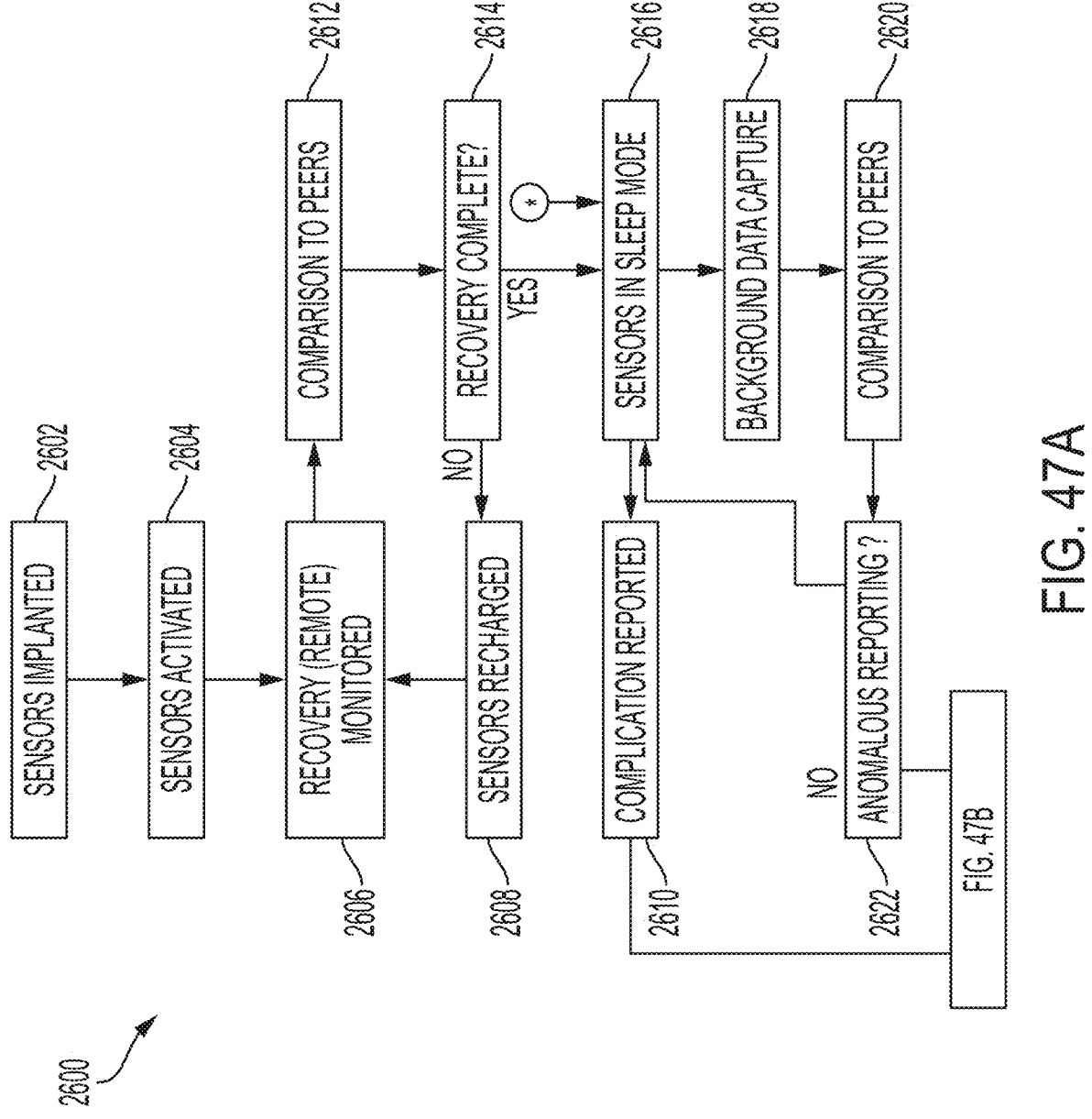
FIGS. 47A and 47B is a flowchart showing steps for patient monitoring according to another embodiment of the present disclosure.
Figure 47B:
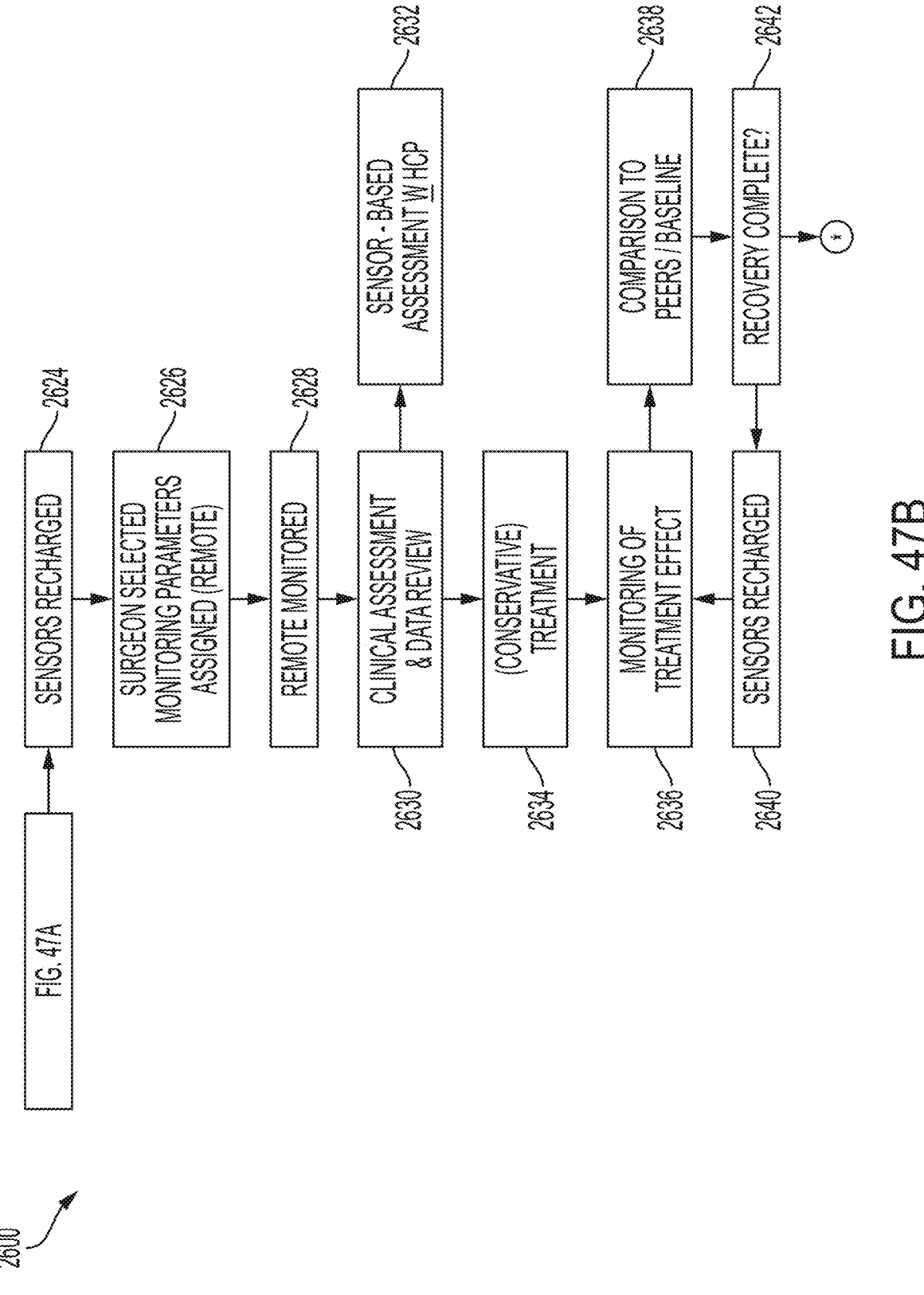

FIGS. 47A and 47B shows steps of a method 2600 for patient monitoring according to an embodiment of the present disclosure. While method 2600 is described with reference to a knee joint implant below, method 2600 can be applied to any implant with sensors described in the present disclosure, including all of the implants disclosed above. After installing the knee joint implant, various sensors within the sensor are activated (steps 2624, 2626) to track and monitor patient rehabilitation and recovery (step 2628). When the tracked data indicates that the desired recovery parameters are achieved, some of the sensors in the knee joint implant are deactivated or turned to a "sleep mode" (step 2616). For example, the recovery target can be a desired range of motion of the knee joint. Once a patient exhibits the desired knee flexion-extension range, some of the sensors on the knee joint implant can be turned off. Alternatively, peer data can be used to identify recovery thresholds (step 2612). If the recovery threshold or milestones are not achieved, the knee joint implant continues to charge and use all sensors (step 2608). Some sensors in the knee joint implant will be periodically used even after achieving the recovery milestones to monitor for early identification of improper implant performance (step 2610, 2618, 2620). For example, after turning off the magnetic readers upon achieving the desired flexion-extension range of motion, the pH or temperature sensors can be used to periodically measure alkalinity and temperature to identify infection or implant failure. Upon identification of an anomalous condition, the knee joint implant can be configured to fully recharge and turn on the previously turned off sensors to provide additional implant performance measurements (step 2624). A surgeon can customize the sensor readings and frequency based on the observed condition (steps 2626 and 2628). Additional rehabilitation steps for patient recovery can be provided to the patient at this point. The impact of the new rehabilitation steps can be monitored and compared with peers to observe patient recovery (steps 2636-2642).

Figure 48:
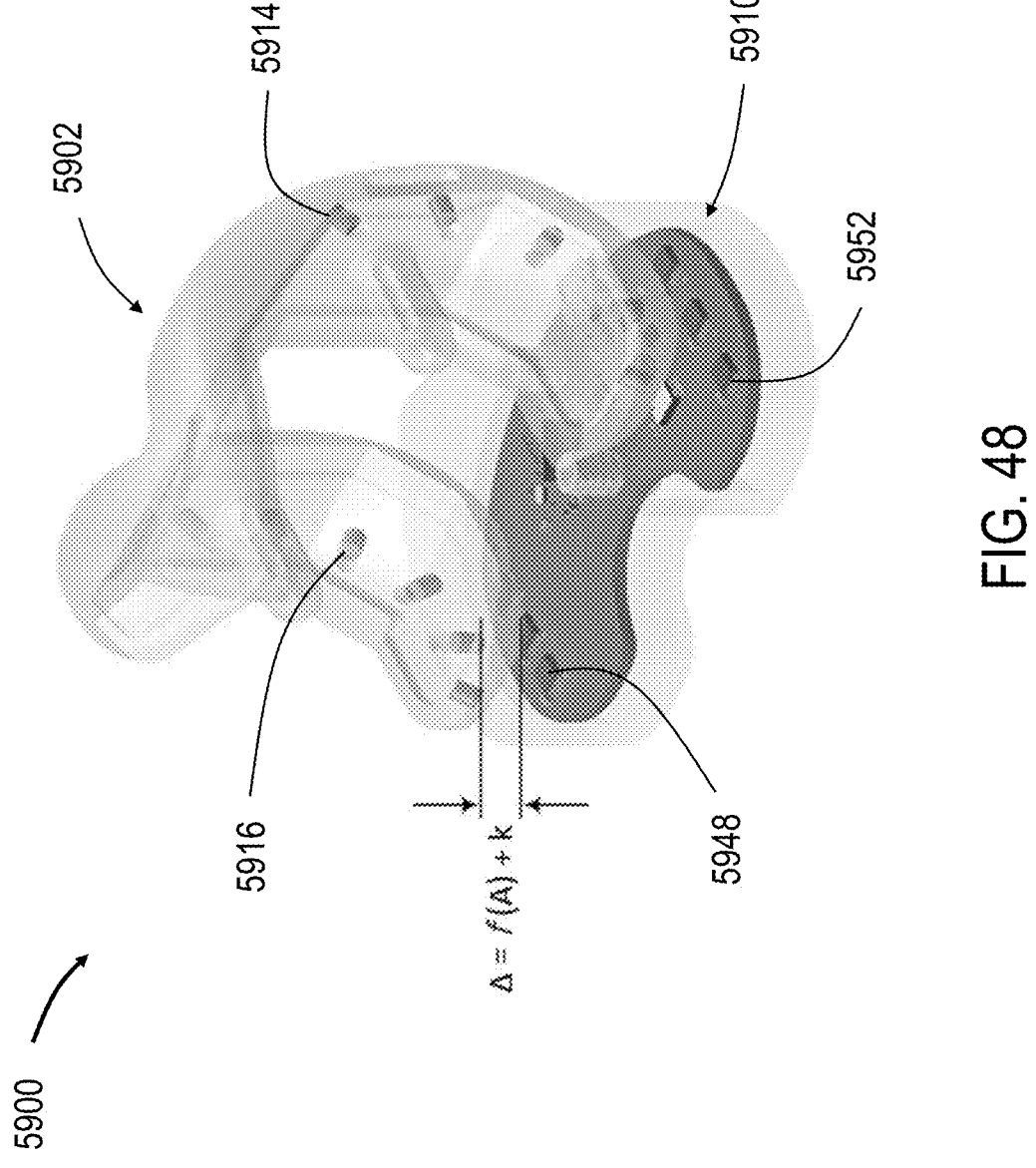
FIG. 48 is an isometric view of a knee joint implant according to another embodiment of the present disclosure.
Figure 49:
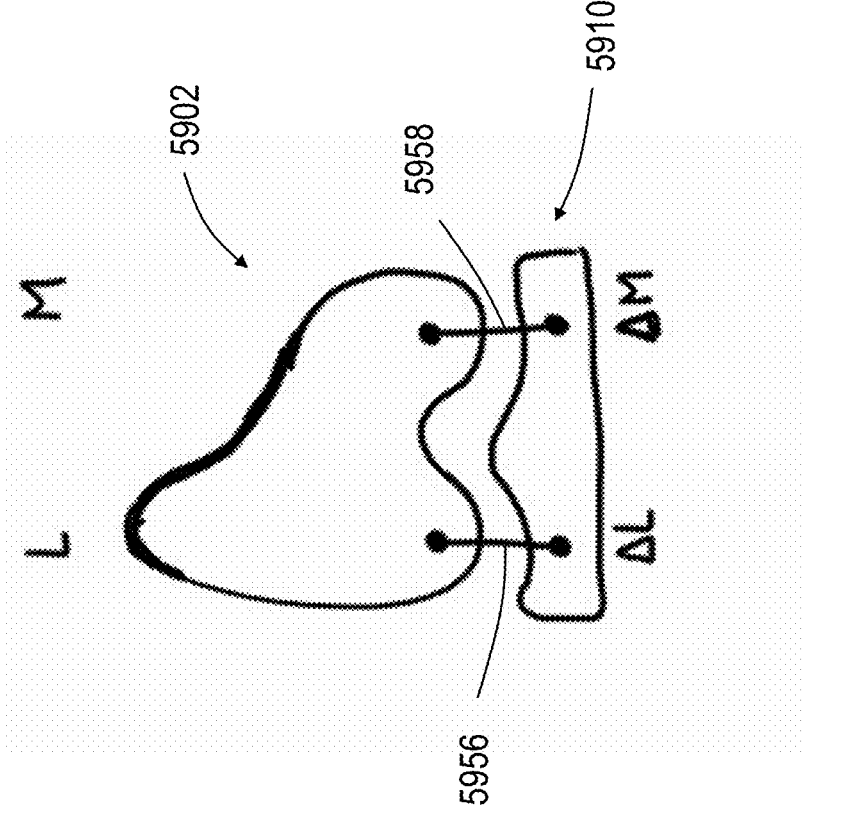
FIG. 49 is a front view the knee joint implant of FIG. 48.

FIGS. 48 and 49 show a knee joint implant 5900 according to another embodiment of the present disclosure. Knee joint implant 5900 is similar to knee joint implant 200, and therefore like elements are referred to with similar numerals within the 5900-series of numbers. For example, knee joint implant 5900 includes a femoral implant 5902 with a plurality of medial magnetic markers 5914 and lateral magnetic markers 5916, a tibial implant (not shown) and a tibial insert 5910 with medial marker readers 5952 and lateral marker readers 5948. Knee joint implant 5900 can be used to accurately measure and determine gaps between femoral implant 5902 and the tibial implant or tibial insert 5910. These measurements can be performed intra-operatively during a knee procedure such as a TKA using the magnetic markers and marker readers of knee joint implant 5900. Amplitude of the magnetic flux read by the lateral and medial markers from the respective markers can be used to precisely calculate medial and lateral gaps between the femoral implant and tibial implant using the formula below.

$$\Delta = f(A) + k$$

"$\Delta$" represents the gap between the femoral and tibial implant, "A" is the amplitude of the magnetic flux reading and "k" is a constant dependent on the knee joint implant and marker/reader arrangement. Amplitude "A" can be derived from the magnetic flux readings and may not directly correlate to the amplitude of a single marker/reader. Intra-operative gap measurements allow a surgeon to accurately position and align the femoral and tibial implants.

A medial gap 5956 and a lateral gap 5958 can be individually calculated using the formula disclose above as best shown in FIG. 49. Thus, a surgeon can utilize knee joint implant 5900 to accurately determine medial and lateral joint gaps intra-operatively and ensure accurate positioning and alignment of the implant components. Additionally, a surgeon can determine contact points or surfaces between the knee joint implant components to ensure proper placement of same.

Referring back to FIG. 45, method 2400 in addition to showing a method to determine implant wear as more fully explained above, shows a method for intra-operative measurement and adjustment of knee joint implant gap according to another embodiment of the present disclosure. While method 2400 is described with reference to a knee joint implant below, method 2400 can be applied to any implant with sensors described in the present disclosure, including all of the implants disclosed above. In a first step 2402, a knee angle of a patient with the knee joint implant is measured. The knee is then placed in full extension in a step 2404. Hall sensor amplitudes are measured in a step 2408. This process is repeated over time to track the Hall sensor amplitude. These values are then compared with calibrated Hall sensor amplitude values obtained for known—i.e., measured, knee joint gaps. As the Hall sensor amplitudes are related (nonlinear relationship) to a distance between the markers and the marker readers—i.e., gap, a difference between the initial Hall sensor amplitudes and current Hall sensor amplitudes from step 2408 represents difference between the measure gap and the desired target gap. The correlation between two variables is not easily quantified as it is a nonlinear relationship; therefore, the gap between them can only be determined by employing the use of an algorithm or neural network. When the desired target gap on the medial and lateral sides are reached in a step 2420, the surgeon is notified that the desired knee joint implant gaps have been achieved in step 2422.

Figure 50:
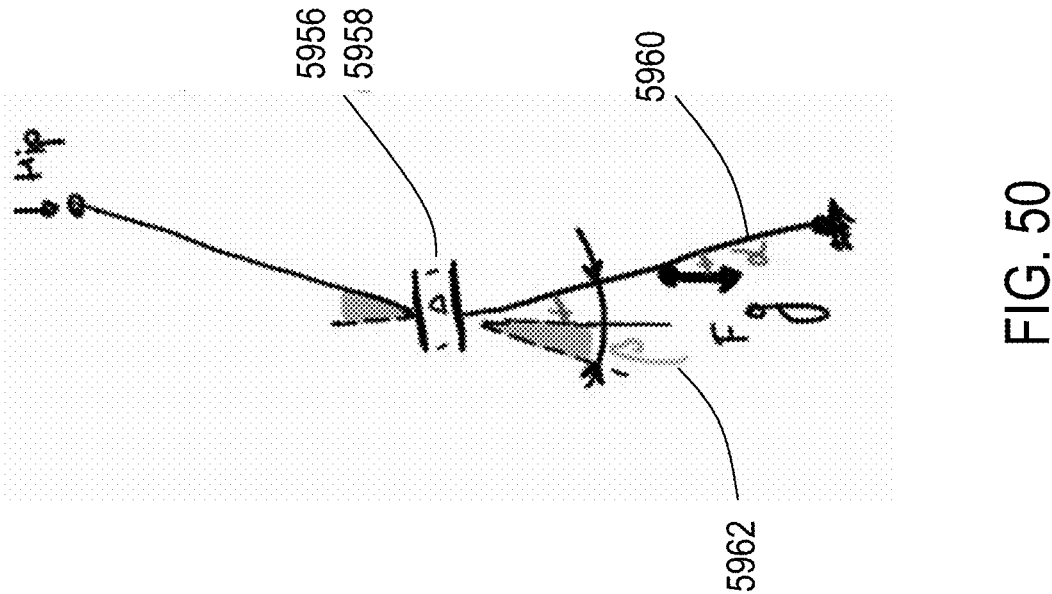
FIG. 50 is a schematic drawing of a method for gap measurement of the knee joint implant of FIG. 48.

Once the desired knee joint implant gaps are achieved, the surgeon can then apply varus-valgus movement to test for gaps in the medial and lateral sides as best shown in FIG. 50. "a" 5960 can be obtained from an IMU on knee joint implant 5900, "$\Delta$" represent the gap distances can be determined by the markers and marker readers as described above, and "f" 5962 is an assumed constant dependent on knee joint implant 5900.

Implant lift-off (medial/latera) can be calculated during the varus-valgus movement test using the formula below:

$$\Delta_{ML\text{-}lift\ off} + V - V_{(femoral)} + V - V_{(tibial)} = HKA$$

V-V (femoral) is assumed to be a constant and "HKA" represent the hip-knee-angle. If the patient takes a standing pose and the alpha, measured by the embedded IMU in implant component 5910 (tibial insert), deviates from the initial implant reading that was taken during surgery, this indicates that the implant has shifted from its original implanted position, potentially resulting in implant migration or implant loosening.

Figures 51, 52:
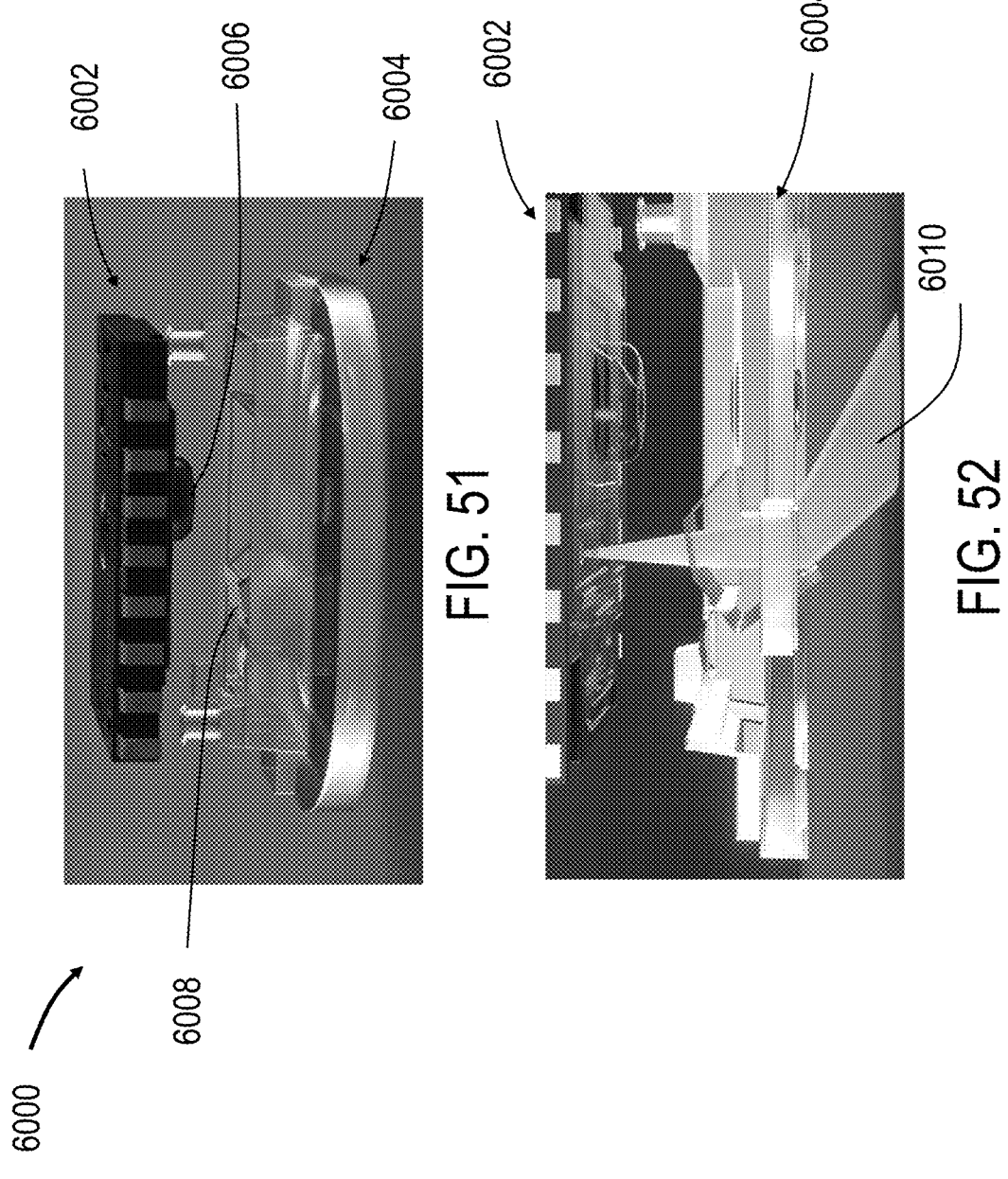
FIG. 51 is a front view of a joint implant according to another embodiment of the present disclosure.
FIG. 52 is a front view of the joint implant of FIG. 51.

FIGS. 51 and 52 show a joint implant 6000 according to another embodiment of the present disclosure. Joint implant 6000 can be a knee joint implant, shoulder implant, spinal implant, hip implant, etc. Joint implant 6000 includes a first component 6002 and a second component 6004. A pattern 6008 on the second component may encode both the position based on the size and shape of the pattern and a reference point to determine a gap between the first and second components. A light source on the first component is provided at a shallow angle by means of a prism as best shown in FIG. 52. This light reflects 6010 the pattern on the second component and projects onto a retina IC 6006 of the first component. The image size is compared to a predefined value based on the position (e.g., a table with expected size as a function of position). If the size of the detected pattern is bigger than the predefined boundary, the first component is closer to the sensor (and thus the second component). The difference in detected pattern size versus the desired pattern size is directly proportionally to the difference between the actual gap versus the target gap between the first and second components. For example, if the pattern read is smaller than the predefined reference, the first component is further away from the sensor proportional to the difference in size between the read pattern and stored pattern.

Figures 53, 54:
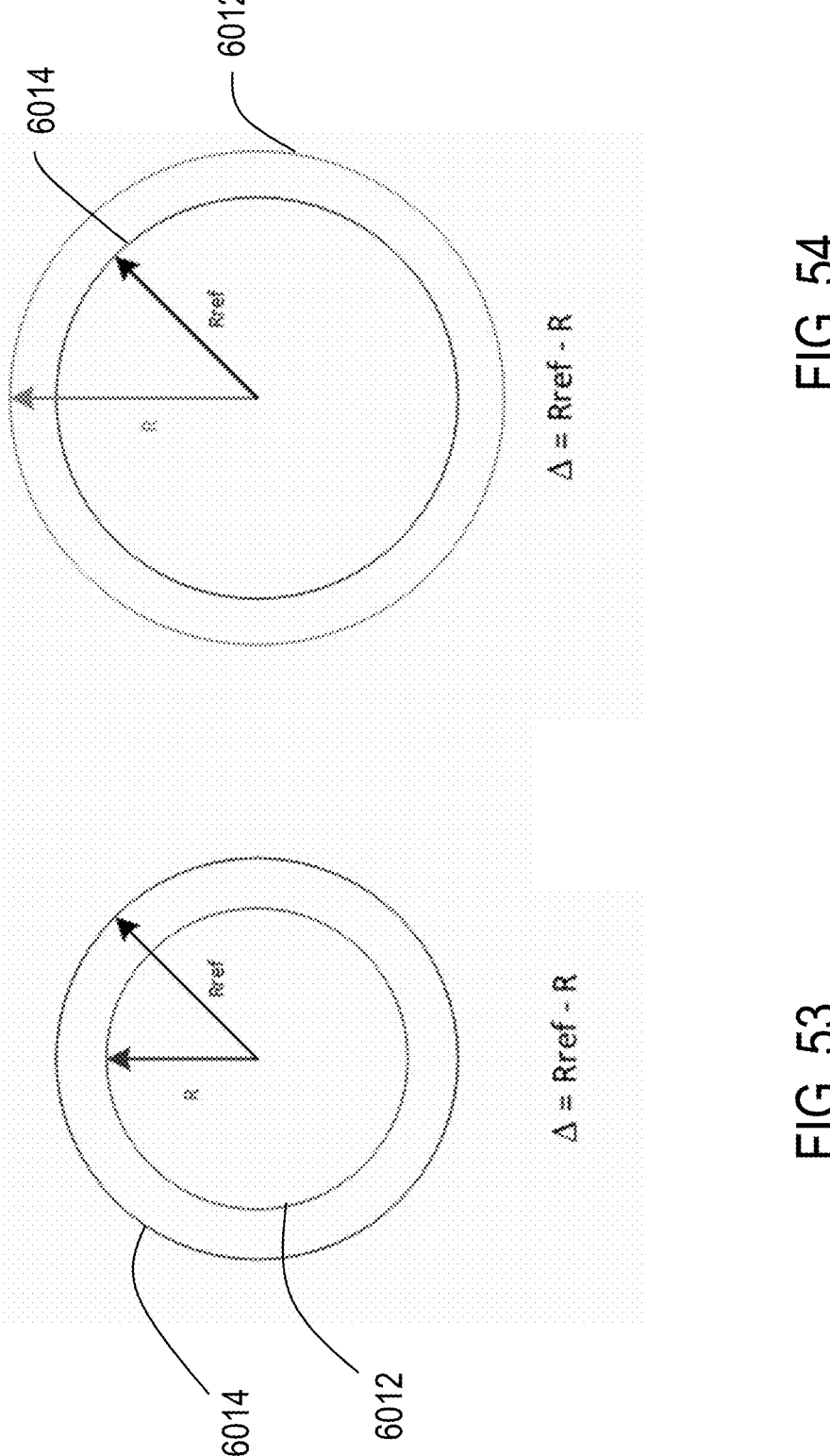
FIG. 53 is schematic drawing of a first gap measurement of the joint implant of FIG. 51.
FIG. 54 is a schematic drawing of a second gap measurement of the joint implant of FIG. 51.

FIGS. 53 and 54 show a circular pattern 6008 being used in joint implant 6000 to intra-operatively determine gaps between the first and second components. When a radius of the detected pattern 6012 is less than the target radius 6014 as shown in FIG. 91, the gap between the first and second components is above the target gap. Similarly, when a radius of the detected pattern 6012 is greater than the radius of the target radius 6014, the gap between the first and second is below the target gap. Thus, a surgeon can intra-operatively and in real time determine the desired gap between the first and second components of joint implant 6000. While a circle is used in this embodiment, other any other shapes such as squares, bar codes, etc. can be used in other embodiments of the present disclosure.

Figures 55, 56:
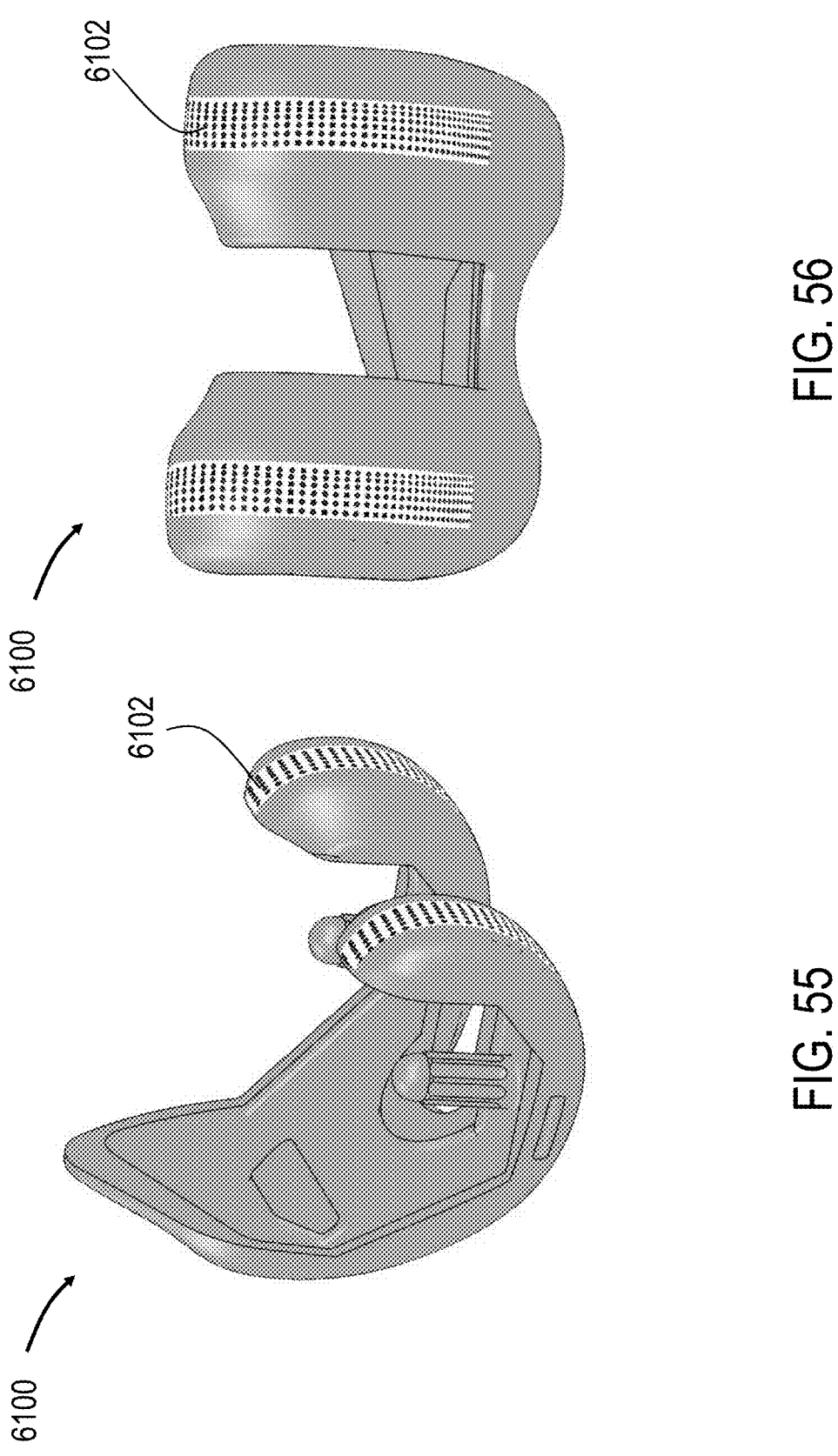
FIG. 55 is a side view of a femoral implant according to an embodiment of the present disclosure.
FIG. 56 is a bottom view of the femoral implant of FIG. 55.

FIGS. 55 and 56 show a femoral implant 6100 of knee joint implant according to another embodiment of the present disclosure. A pattern 6102 can be imprinted to a surface of femoral implant 6100 by etching or other suitable techniques. An LED placed in an external device, such as a TKA gauge assembly can be used to reflect light of pattern 6102. The reflected light from the surface of the femoral implant is read on a reading device to determine the relative distance between a tibial trial or implant and the femoral implant by comparing the detected pattern to target pattern. Thus, a surgeon can intra-operatively adjust the joint gap in real time for proper positioning of the joint implants.

While a knee joint implant, hip implant, shoulder implant and a spinal implant are disclosed above, all or any of the aspects of the present disclosure can be used with any other implant such as an intramedullary nail, a bone plate, a bone screw, an external fixation device, an interference screw, etc. Although, the present disclosure generally refers to implants, the systems and method disclosed above can be used with trials to provide real time information related to trial performance. While sensors disclosed above are generally located in the tibial implant (tibial insert) of the knee joint implant, the sensors can be located within the femoral implant in other embodiments. Sensor shape, size and configuration can be customized based on the type of implant and patient-specific needs.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the paragraphs below.

The invention claimed is:

1. A method for detecting joint implant gap, the method comprising the steps of:
   providing a first implant to a first bone of a joint, the first implant including at least one magnetic marker;
   providing a second implant to a second bone of the joint, the second implant configured to contact the first implant, the second implant including at least one magnetic sensor to detect a magnetic flux density of the magnetic marker;
   measuring an amplitude of the magnetic flux density using the magnetic sensor, and
   determining a gap between the first implant and the second implant from the measured amplitude of the magnetic flux density.

2. The method of claim 1, wherein the steps of measuring the amplitude of the magnetic flux density and determining the gap between the first implant and the second implant is performed intra-operatively.

3. The method of claim 2, wherein the step of determining the gap between the first implant and the second implant is performed by comparing the measured amplitude of the magnetic flux density to a predetermined value.

4. The method of claim 3, wherein the predetermined value is stored in a database.

5. The method of claim 4, wherein the database includes a library of magnetic flux density amplitude and corresponding gap distances.

6. The method claim 5, further comprising a step of initiating a warning when the measured amplitude of magnetic flux density does not match the predetermined value.

7. The method of claim 1, wherein the joint implant is any of a knee joint implant, shoulder implant, hip implant and spine implant.

8. The method of claim 1, wherein the joint implant is a knee joint implant, the first implant is a femoral implant and the second implant is a tibial implant.

9. The method of claim 8, further comprising a step of performing a varus-valgus movement to determine femoral and tibial implant lift off.

10. The method of claim 1, wherein the first implant includes a medial magnetic marker and a lateral magnetic marker and the second implant includes a medial magnetic sensor and a lateral magnetic sensor.

11. The method of claim 10, wherein the step of measuring the amplitude comprises measuring an amplitude of a medial magnetic flux density of the medial magnetic marker by the medial magnetic sensor and an amplitude of a lateral magnetic flux density of the lateral magnetic marker by the lateral magnetic sensor.

12. The method of claim 11, wherein the step of determining the gap comprises determining a medial gap between a medial portion of the first implant and the second implant from the measured amplitude of the medial magnetic flux density and determining a lateral medial gap between a lateral portion of the first implant and the second implant from the measured amplitude of the lateral magnetic flux density.

13. The method of claim 1, wherein the steps of measuring the amplitude of the magnetic flux density and determining the gap between the first implant and the second implant is performed post-operatively.

14. A method for detecting joint implant gap, the method comprising the steps of:
   coupling a first implant to a first bone of a joint, the first implant including a light source;

coupling a second implant to a second bone of the joint, the second implant configured to contact the first implant, the second implant including a pattern;

transmitting light from the light source through the pattern;

reading the light passing through the pattern from a reader disposed on the first implant; and determining a gap between the first implant and the second implant from the light passing through the pattern.

15. The method of claim 14, wherein the steps of transmitting the light, reading the light passing through the pattern and determining the gap between the first implant and the second implant is performed intra-operatively.

16. The method of claim 15, wherein the step of determining the gap between the first implant and the second implant is performed by comparing a formed pattern generated by the light passing through the pattern to a predetermined pattern.

17. The method of claim 15, wherein the predetermined pattern is stored in a database.

18. The method of claim 17, wherein the database includes a library of predetermined patterns and corresponding gap distances.

19. The method claim 18, further comprising a step of initiating a warning when the formed pattern does not match the predetermined pattern.

20. A method for detecting joint implant gap, the method comprising the steps of:

measuring an amplitude of a magnetic flux density using a magnetic sensor associated with a second implant on a second bone of a joint, the magnetic sensor detecting a magnetic flux density of a magnetic marker associated with a first implant on a first bone of the joint, and determining a gap between the first implant and the second implant from the measured amplitude of the magnetic flux density.

21. The method of claim 20, wherein a position of the first implant with respect to the second implant is determined by the gap between the first implant and the second implant.

* * * * *